(12) United States Patent
Martin et al.

(10) Patent No.: US 11,357,486 B2
(45) Date of Patent: Jun. 14, 2022

(54) CLOSURE SYSTEM AND USES THEREOF

(75) Inventors: Christopher Martin, Oughterard (IE); Damien Ryan, Galway (IE); Peter Grant, Galway (IE); Michael Dunning, Galway (IE); Gerard Brett, Claregalway (IE); Kevin Walsh, Bama (IE); Desmond John Regan, Loughrea (IE)

(73) Assignee: VIVASURE MEDICAL LIMITED, Galway (IE)

( * ) Notice: Subject to any disclaimer, the term of this patent is extended or adjusted under 35 U.S.C. 154(b) by 543 days.

(21) Appl. No.: 12/982,852

(22) Filed: Dec. 30, 2010

(65) Prior Publication Data

US 2011/0224728 A1 Sep. 15, 2011

Related U.S. Application Data

(60) Provisional application No. 61/299,974, filed on Jan. 30, 2010, provisional application No. 61/291,132, filed on Dec. 30, 2009.

(51) Int. Cl.
*A61B 17/00* (2006.01)
*A61B 17/04* (2006.01)
*A61B 17/02* (2006.01)

(52) U.S. Cl.
CPC ...... *A61B 17/0057* (2013.01); *A61B 17/0401* (2013.01); *A61B 17/0218* (2013.01); *A61B 17/0469* (2013.01); *A61B 17/0485* (2013.01); *A61B 2017/00597* (2013.01); *A61B 2017/00619* (2013.01); *A61B 2017/00623* (2013.01); *A61B 2017/00659* (2013.01); *A61B 2017/00663* (2013.01); *A61B 2017/0404* (2013.01); *A61B 2017/0409* (2013.01); *A61B 2017/0411* (2013.01); *A61B 2017/0414* (2013.01); *A61B 2017/0417* (2013.01); *A61B 2017/0464* (2013.01)

(58) Field of Classification Search
CPC ............ A61B 17/0057; A61B 17/0401; A61B 2017/0464; A61B 2017/00663; A61B 2017/00615
USPC .......................................... 606/213–216, 232
See application file for complete search history.

(56) References Cited

U.S. PATENT DOCUMENTS

| | | | |
|---|---|---|---|
| 321,721 | A | 7/1885 | Hassan |
| 2,001,638 | A | 5/1935 | Gustaf |
| 2,560,162 | A | 7/1951 | Ferguson |
| 2,778,254 | A | 1/1957 | Carapellotti |
| 3,874,388 | A | 4/1975 | King et al. |
| 4,299,230 | A | 11/1981 | Kubota |

(Continued)

FOREIGN PATENT DOCUMENTS

| | | |
|---|---|---|
| CN | 105073064 A | 11/2015 |
| DE | 19711288 B4 | 11/2004 |

(Continued)

OTHER PUBLICATIONS

International Search Report for PCT/IB2010/003461 dated Oct. 11, 2011, published on Dec. 1, 2011.

(Continued)

*Primary Examiner* — Shaun L David
(74) *Attorney, Agent, or Firm* — Choate, Hall & Stewart LLP; William R. Haulbrook; Peter A. Flynn

(57) ABSTRACT

The present invention relates generally to a closure system for use in surgical procedures.

17 Claims, 79 Drawing Sheets

(56) References Cited

U.S. PATENT DOCUMENTS

| | | |
|---|---|---|
| 4,583,540 A | 4/1986 | Malmin |
| 4,650,472 A | 3/1987 | Bates |
| 4,705,040 A | 11/1987 | Mueller et al. |
| 4,744,364 A | 5/1988 | Kensey |
| 4,852,568 A | 8/1989 | Kensey |
| 4,890,612 A | 1/1990 | Kensey |
| 4,896,668 A | 1/1990 | Popoff et al. |
| 5,021,059 A | 6/1991 | Kensey et al. |
| 5,037,433 A | 8/1991 | Wilk et al. |
| 5,053,046 A | 10/1991 | Janese |
| 5,085,661 A | 2/1992 | Moss |
| 5,127,412 A | 7/1992 | Cosmetto et al. |
| 5,171,258 A | 12/1992 | Bales et al. |
| 5,192,301 A | 3/1993 | Kamiya et al. |
| 5,269,804 A | 12/1993 | Bales et al. |
| 5,282,827 A | 2/1994 | Kensey et al. |
| 5,320,461 A | 6/1994 | Stanesic |
| 5,330,488 A | 7/1994 | Goldrath |
| 5,336,231 A | 8/1994 | Adair |
| 5,342,393 A | 8/1994 | Stack |
| 5,350,399 A | 9/1994 | Erlebacher et al. |
| 5,366,480 A * | 11/1994 | Corriveau .......... A61B 17/0401 606/232 |
| 5,391,182 A | 2/1995 | Chin |
| 5,431,639 A | 7/1995 | Shaw |
| 5,462,560 A | 10/1995 | Stevens |
| 5,470,337 A | 11/1995 | Moss |
| 5,501,691 A | 3/1996 | Goldrath |
| 5,501,700 A | 3/1996 | Hirata |
| 5,507,755 A | 4/1996 | Gresl et al. |
| 5,527,322 A | 6/1996 | Klein et al. |
| 5,531,759 A | 7/1996 | Kensey et al. |
| 5,545,178 A * | 8/1996 | Kensey et al. ................ 606/213 |
| 5,549,633 A | 8/1996 | Evans et al. |
| 5,593,422 A | 1/1997 | Muijs Van de Moer et al. |
| 5,601,557 A | 2/1997 | Hayhurst |
| 5,601,571 A | 2/1997 | Moss |
| 5,620,461 A | 4/1997 | Muijs Van De Moer et al. |
| 5,653,716 A | 8/1997 | Malo et al. |
| 5,662,681 A | 9/1997 | Nash et al. |
| 5,665,096 A | 9/1997 | Yoon |
| 5,676,689 A | 10/1997 | Kensey et al. |
| 5,690,674 A | 11/1997 | Diaz |
| 5,700,273 A | 12/1997 | Buelna et al. |
| 5,700,277 A | 12/1997 | Nash et al. |
| 5,707,393 A | 1/1998 | Kensey et al. |
| 5,722,981 A | 3/1998 | Stevens |
| 5,755,727 A | 5/1998 | Kontos |
| 5,782,861 A | 7/1998 | Cragg et al. |
| 5,797,939 A | 8/1998 | Yoon |
| 5,814,065 A | 9/1998 | Diaz |
| 5,817,074 A | 10/1998 | Racz |
| 5,827,281 A | 10/1998 | Levin |
| 5,860,990 A | 1/1999 | Nobles et al. |
| 5,861,003 A | 1/1999 | Latson et al. |
| 5,868,762 A | 2/1999 | Cragg et al. |
| 5,916,236 A | 6/1999 | Muijs Van de Moer et al. |
| 5,935,147 A | 8/1999 | Kensey et al. |
| 5,941,899 A | 8/1999 | Granger et al. |
| 5,954,732 A | 9/1999 | Hart et al. |
| 5,997,515 A | 12/1999 | de la Torre et al. |
| 6,007,563 A | 12/1999 | Nash et al. |
| 6,033,427 A | 3/2000 | Lee |
| 6,056,768 A | 5/2000 | Cates et al. |
| 6,080,183 A | 6/2000 | Tsugita et al. |
| 6,126,675 A | 10/2000 | Shchervinsky et al. |
| 6,136,010 A | 10/2000 | Modesitt et al. |
| 6,179,863 B1 | 1/2001 | Kensey et al. |
| 6,190,400 B1 | 2/2001 | Van De Moer et al. |
| 6,200,328 B1 | 3/2001 | Cragg et al. |
| 6,206,895 B1 | 3/2001 | Levinson |
| 6,241,768 B1 | 6/2001 | Agarwal et al. |
| 6,245,080 B1 | 6/2001 | Levinson |
| 6,296,658 B1 | 10/2001 | Gershony et al. |
| 6,319,263 B1 | 11/2001 | Levinson |
| 6,350,274 B1 | 2/2002 | Li |
| 6,375,671 B1 | 4/2002 | Kobayashi et al. |
| 6,383,208 B1 | 5/2002 | Sancoff et al. |
| 6,395,015 B1 | 5/2002 | Borst et al. |
| 6,398,796 B2 | 6/2002 | Levinson |
| 6,425,911 B1 * | 7/2002 | Akerfeldt et al. ............ 606/213 |
| 6,461,364 B1 | 10/2002 | Ginn et al. |
| 6,485,481 B1 | 11/2002 | Pfeiffer |
| 6,500,184 B1 | 12/2002 | Chan et al. |
| 6,508,828 B1 * | 1/2003 | Akerfeldt .......... A61B 17/0057 606/215 |
| 6,596,012 B2 | 7/2003 | Akerfeldt et al. |
| 6,596,014 B2 | 7/2003 | Levinson et al. |
| 6,596,915 B1 | 7/2003 | Satyapal et al. |
| 6,638,286 B1 | 10/2003 | Burbank et al. |
| 6,669,707 B1 | 12/2003 | Swanstrom et al. |
| 6,702,835 B2 | 3/2004 | Ginn |
| 6,730,112 B2 | 5/2004 | Levinson |
| 6,764,500 B1 | 7/2004 | Muijs Van De Moer et al. |
| 6,770,070 B1 | 8/2004 | Balbierz |
| 6,779,701 B2 | 8/2004 | Bailly et al. |
| 6,786,915 B2 | 9/2004 | Akerfeldt et al. |
| 6,860,895 B1 | 3/2005 | Akerfeldt et al. |
| 6,890,342 B2 | 5/2005 | Zhu et al. |
| 6,932,824 B1 | 8/2005 | Roop et al. |
| 6,939,363 B2 | 9/2005 | Akerfeldt |
| 6,942,674 B2 | 9/2005 | Belef et al. |
| 6,949,107 B2 | 9/2005 | McGuckin, Jr. et al. |
| 6,949,114 B2 | 9/2005 | Milo et al. |
| 6,964,668 B2 | 11/2005 | Modesitt et al. |
| 6,969,397 B2 | 11/2005 | Ginn |
| 6,984,219 B2 | 1/2006 | Ashby et al. |
| 6,989,022 B2 | 1/2006 | Nowakowski |
| 6,997,940 B2 | 2/2006 | Bonutti |
| 7,001,398 B2 | 2/2006 | Carley et al. |
| 7,001,400 B1 | 2/2006 | Modesitt et al. |
| 7,008,440 B2 | 3/2006 | Sing et al. |
| 7,008,441 B2 | 3/2006 | Zucker |
| 7,008,442 B2 | 3/2006 | Brightbill |
| 7,094,248 B2 | 8/2006 | Bachinski et al. |
| 7,169,168 B2 | 1/2007 | Muijs Van De Moer et al. |
| 7,326,221 B2 | 2/2008 | Sakamoto et al. |
| 7,462,188 B2 | 12/2008 | McIntosh |
| 7,534,248 B2 | 5/2009 | Mikkaichi et al. |
| 7,569,063 B2 | 8/2009 | Bailly et al. |
| 7,662,161 B2 | 2/2010 | Briganti et al. |
| 7,678,133 B2 | 3/2010 | Modesitt |
| 7,753,935 B2 | 7/2010 | Brett et al. |
| 7,846,180 B2 | 12/2010 | Cerier |
| 7,918,868 B2 | 4/2011 | Marshall et al. |
| 7,998,169 B2 | 8/2011 | Modesitt |
| 8,002,791 B2 | 8/2011 | Modesitt |
| 8,002,792 B2 | 8/2011 | Modesitt |
| 8,002,793 B2 | 8/2011 | Modesitt |
| 8,012,168 B2 | 9/2011 | Modesitt |
| 8,083,767 B2 | 12/2011 | Modesitt |
| 8,137,380 B2 | 3/2012 | Green et al. |
| 8,177,795 B2 | 5/2012 | Niese et al. |
| 8,241,325 B2 | 8/2012 | Modesitt |
| 8,267,942 B2 | 9/2012 | Szabo et al. |
| 8,361,092 B1 | 1/2013 | Asfora |
| 8,529,431 B2 | 9/2013 | Baker et al. |
| 8,597,324 B2 | 12/2013 | Briganti et al. |
| 8,652,166 B2 | 2/2014 | Åkerfeldt |
| 8,821,507 B2 | 9/2014 | Axelson, Jr. et al. |
| 8,906,050 B2 | 12/2014 | Brett et al. |
| 9,060,751 B2 | 6/2015 | Martin et al. |
| 9,610,070 B2 | 4/2017 | Martin |
| 9,850,013 B2 | 12/2017 | Grant et al. |
| 10,206,668 B2 | 2/2019 | McGoldrick et al. |
| 10,433,826 B2 | 10/2019 | Grant et al. |
| 2001/0044631 A1 | 11/2001 | Akin et al. |
| 2002/0019648 A1 * | 2/2002 | Akerfeldt .......... A61B 17/0057 606/213 |
| 2002/0019649 A1 | 2/2002 | Sikora et al. |
| 2002/0107506 A1 | 8/2002 | McGuckin et al. |
| 2002/0169377 A1 | 11/2002 | Khairkhahan et al. |
| 2002/0177864 A1 | 11/2002 | Camrud |

(56) References Cited

U.S. PATENT DOCUMENTS

| | | | |
|---|---|---|---|
| 2002/0198562 A1* | 12/2002 | Akerfeldt | A61B 17/0057 606/213 |
| 2003/0050665 A1 | 3/2003 | Ginn | |
| 2003/0060846 A1 | 3/2003 | Egnelov et al. | |
| 2003/0078598 A1 | 4/2003 | Ginn et al. | |
| 2003/0093093 A1 | 5/2003 | Modesitt et al. | |
| 2003/0120305 A1 | 6/2003 | Jud et al. | |
| 2003/0144695 A1 | 7/2003 | McGuckin et al. | |
| 2003/0216756 A1 | 11/2003 | Klein et al. | |
| 2004/0082906 A1 | 4/2004 | Tallarida et al. | |
| 2004/0092964 A1 | 5/2004 | Modesitt et al. | |
| 2004/0092969 A1 | 5/2004 | Kumar | |
| 2004/0093025 A1* | 5/2004 | Egnelov | 606/214 |
| 2004/0098044 A1 | 5/2004 | Van de Moer et al. | |
| 2004/0133238 A1* | 7/2004 | Cerier | A61B 17/0401 606/232 |
| 2004/0176798 A1 | 9/2004 | Epstein et al. | |
| 2004/0243122 A1 | 12/2004 | Auth et al. | |
| 2005/0021055 A1 | 1/2005 | Toubia et al. | |
| 2005/0021059 A1 | 1/2005 | Cole et al. | |
| 2005/0033326 A1 | 2/2005 | Briganti et al. | |
| 2005/0070957 A1 | 3/2005 | Das | |
| 2005/0143817 A1 | 6/2005 | Hunter et al. | |
| 2005/0149065 A1 | 7/2005 | Modesitt | |
| 2005/0181008 A1 | 8/2005 | Hunter et al. | |
| 2005/0209613 A1 | 9/2005 | Roop et al. | |
| 2005/0251201 A1 | 11/2005 | Roue et al. | |
| 2005/0267520 A1 | 12/2005 | Modesitt | |
| 2005/0273135 A1 | 12/2005 | Chanduszko et al. | |
| 2005/0288706 A1 | 12/2005 | Widomski et al. | |
| 2006/0100665 A1 | 5/2006 | Von Oepen et al. | |
| 2006/0106418 A1 | 5/2006 | Seibold et al. | |
| 2006/0142784 A1 | 6/2006 | Kontos | |
| 2006/0142797 A1 | 6/2006 | Egnelov | |
| 2006/0265008 A1 | 11/2006 | Maruyama et al. | |
| 2006/0287673 A1 | 12/2006 | Brett et al. | |
| 2007/0112385 A1 | 5/2007 | Conlon | |
| 2007/0135826 A1 | 6/2007 | Zaver et al. | |
| 2007/0179509 A1 | 8/2007 | Nagata et al. | |
| 2007/0179527 A1 | 8/2007 | Eskuri et al. | |
| 2007/0197858 A1 | 8/2007 | Goldfarb et al. | |
| 2007/0255313 A1 | 11/2007 | Modesitt | |
| 2007/0282351 A1 | 12/2007 | Harada et al. | |
| 2007/0282373 A1 | 12/2007 | Ashby et al. | |
| 2008/0228204 A1 | 9/2008 | Hamilton et al. | |
| 2008/0243148 A1 | 10/2008 | Mikkaichi et al. | |
| 2008/0312646 A9 | 12/2008 | Auth et al. | |
| 2009/0012521 A1 | 1/2009 | Axelson, Jr. et al. | |
| 2009/0018574 A1* | 1/2009 | Martin | 606/213 |
| 2009/0048559 A1 | 2/2009 | Grathwohl | |
| 2009/0088723 A1 | 4/2009 | Khosravi et al. | |
| 2009/0112257 A1* | 4/2009 | Preinitz et al. | 606/215 |
| 2009/0143815 A1 | 6/2009 | Eidenschink et al. | |
| 2009/0143821 A1 | 6/2009 | Stupak | |
| 2009/0312786 A1 | 12/2009 | Trask et al. | |
| 2010/0022823 A1 | 1/2010 | Goldfarb et al. | |
| 2010/0094425 A1 | 4/2010 | Bentley et al. | |
| 2010/0114159 A1* | 5/2010 | Roorda | A61B 17/0057 606/215 |
| 2010/0125296 A1 | 5/2010 | Modesitt | |
| 2010/0152772 A1 | 6/2010 | Brett et al. | |
| 2010/0222796 A1 | 9/2010 | Brett et al. | |
| 2010/0228184 A1 | 9/2010 | Mavani et al. | |
| 2011/0077667 A1 | 3/2011 | Singhatat et al. | |
| 2011/0082495 A1 | 4/2011 | Ruiz | |
| 2011/0087270 A1 | 4/2011 | Penner et al. | |
| 2011/0224728 A1 | 9/2011 | Martin et al. | |
| 2012/0059399 A1 | 3/2012 | Hoke et al. | |
| 2012/0089166 A1 | 4/2012 | Modesitt | |
| 2012/0165957 A1 | 6/2012 | Everland et al. | |
| 2012/0226308 A1 | 9/2012 | Martin et al. | |
| 2012/0296275 A1 | 11/2012 | Martin et al. | |
| 2013/0116799 A1 | 5/2013 | Derwin et al. | |
| 2013/0218201 A1 | 8/2013 | Obermiller et al. | |
| 2013/0274795 A1 | 10/2013 | Grant et al. | |
| 2014/0018846 A1 | 1/2014 | Grant et al. | |
| 2014/0018847 A1 | 1/2014 | Grant et al. | |
| 2014/0058439 A1 | 2/2014 | White | |
| 2014/0180314 A1 | 6/2014 | Asfora | |
| 2014/0200597 A1 | 7/2014 | Klein et al. | |
| 2014/0277113 A1 | 9/2014 | Stanley et al. | |
| 2014/0345109 A1 | 11/2014 | Grant et al. | |
| 2015/0045818 A1 | 2/2015 | Kim et al. | |
| 2016/0051239 A1 | 2/2016 | Martin et al. | |
| 2017/0181736 A1 | 6/2017 | McGoldrick et al. | |
| 2017/0281142 A1 | 10/2017 | Martin et al. | |
| 2019/0021710 A1 | 1/2019 | McGoldrick et al. | |

FOREIGN PATENT DOCUMENTS

| | | |
|---|---|---|
| DE | 102010048908 A1 | 4/2012 |
| EP | 0551198 A1 | 7/1993 |
| EP | 0761250 A1 | 3/1997 |
| EP | 0894475 A1 | 2/1999 |
| EP | 2260770 A2 | 12/2010 |
| EP | 2 777 543 A1 | 9/2014 |
| WO | WO-1994/008513 A1 | 4/1994 |
| WO | WO-2000/033744 A1 | 6/2000 |
| WO | WO-2002/102236 A2 | 12/2002 |
| WO | WO-2004/012601 A2 | 2/2004 |
| WO | WO-2004/012603 A2 | 2/2004 |
| WO | WO-2004/012627 A1 | 2/2004 |
| WO | WO-2006/117766 A2 | 11/2006 |
| WO | WO-2007011353 A2 | 1/2007 |
| WO | WO-2008042229 A2 | 4/2008 |
| WO | WO-2008152617 A2 | 12/2008 |
| WO | WO-2009/070651 A1 | 6/2009 |
| WO | WO-2009/149455 A1 | 12/2009 |
| WO | WO-2010027693 A2 | 3/2010 |
| WO | WO-2010123821 A1 | 10/2010 |
| WO | WO-2011080588 A2 | 7/2011 |
| WO | WO-2012/090069 A2 | 7/2012 |
| WO | WO-2012/156819 A2 | 11/2012 |
| WO | WO-2013/128292 A2 | 9/2013 |
| WO | WO-2013/188351 A2 | 12/2013 |
| WO | WO-2014/140325 A1 | 9/2014 |
| WO | WO-2014/141209 A1 | 9/2014 |
| WO | WO-2014/149642 A2 | 9/2014 |
| WO | WO-2017/102941 A1 | 6/2017 |

OTHER PUBLICATIONS

Written Opinion of the ISA for PCT/IB2010/003461 dated Oct. 11, 2011, published on Dec. 1, 2011.
International Preliminary Report on Patentability for PCT/IB2010/003461 dated Jul. 12, 2012, published on Dec. 1, 2011.
International Search Report for PCT/IB2011/003295 dated Jun. 29, 2012.
International Search Report for PCT/IB2013/000839, dated Jan. 14, 2014, published as WO 2013/128292 (6 pages).
International Search Report, PCT/IB2014/059848, 5 pages, dated Jul. 7, 2014.
Written Opinion for PCT/IB2011/003295, dated Jun. 29, 2012.
Written Opinion for PCT/IB2013/000839, dated Jan. 14, 2014, published as WO 2013/128292 (11 pages).
Written Opinion of the International Searching Authority in PCT/IE2006/000043, dated Oct. 29, 2007.
Written Opinion, PCT/IB2014/059848, 8 pages (dated Jul. 7, 2014).
U.S. Appl. No. 62/092,212, filed Dec. 15, 2014, McGoldrick et al.
U.S. Appl. No. 62/092,240, filed Dec. 15, 2014, Grant et al.
U.S. Appl. No. 62/092,235, filed Dec. 15, 2014, Grant et al.
Grant et al., Hales' 1733 Haemastaticks, Anesthesiology, 112:1:65 (2010).
Hales, Stephen, Statical Essays, vol. 2 (1773).

* cited by examiner

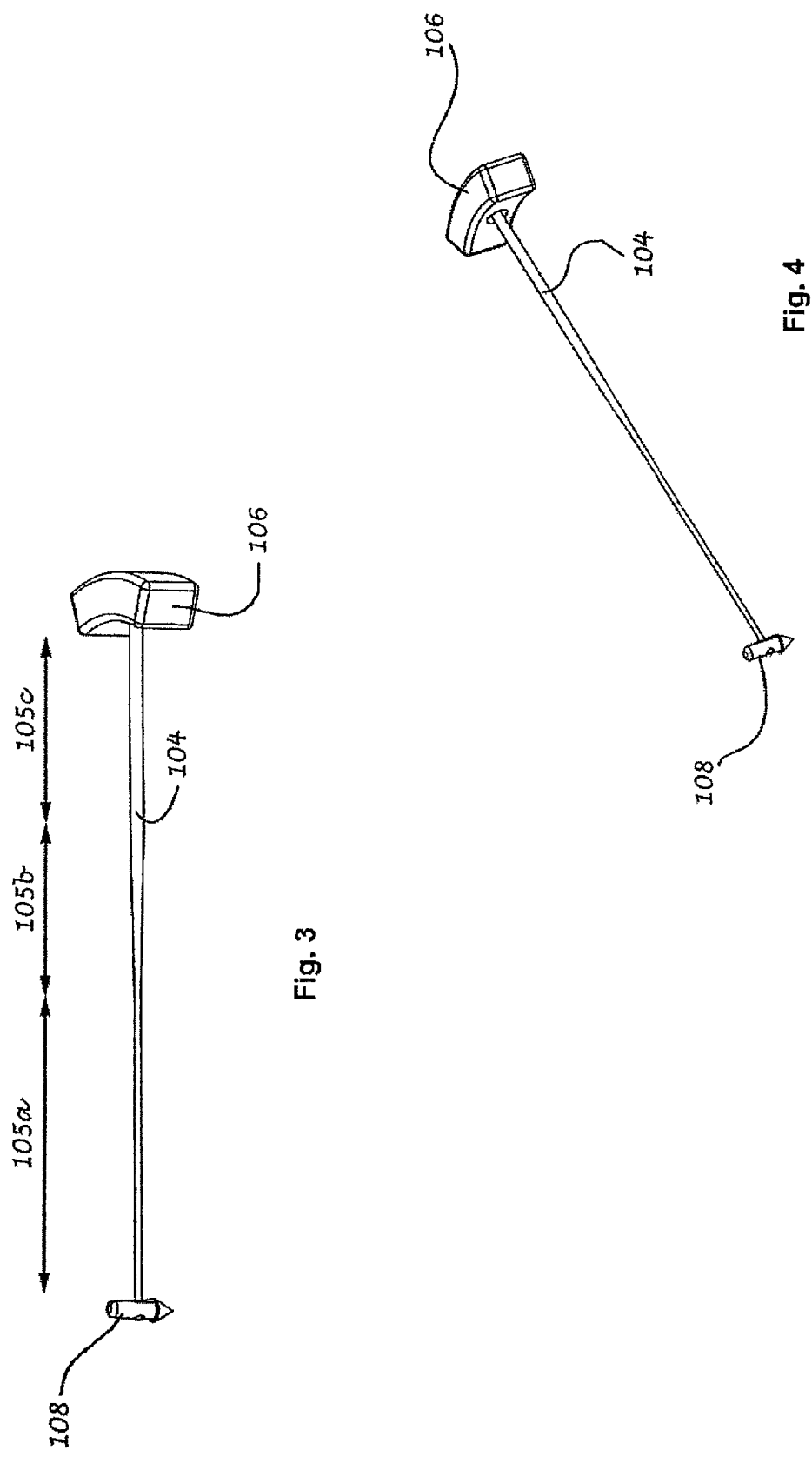

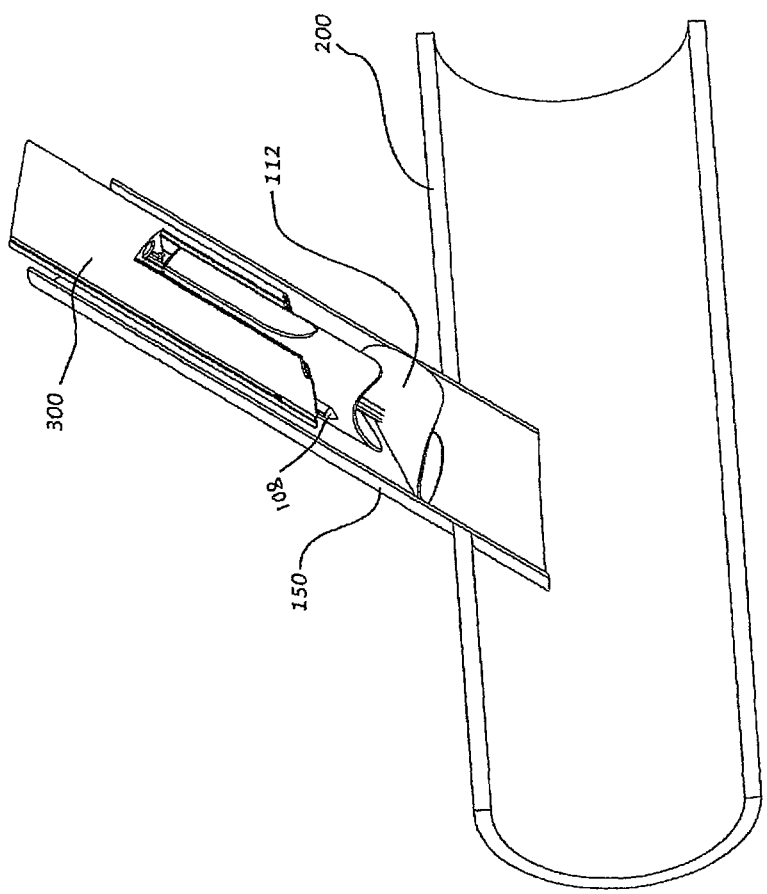

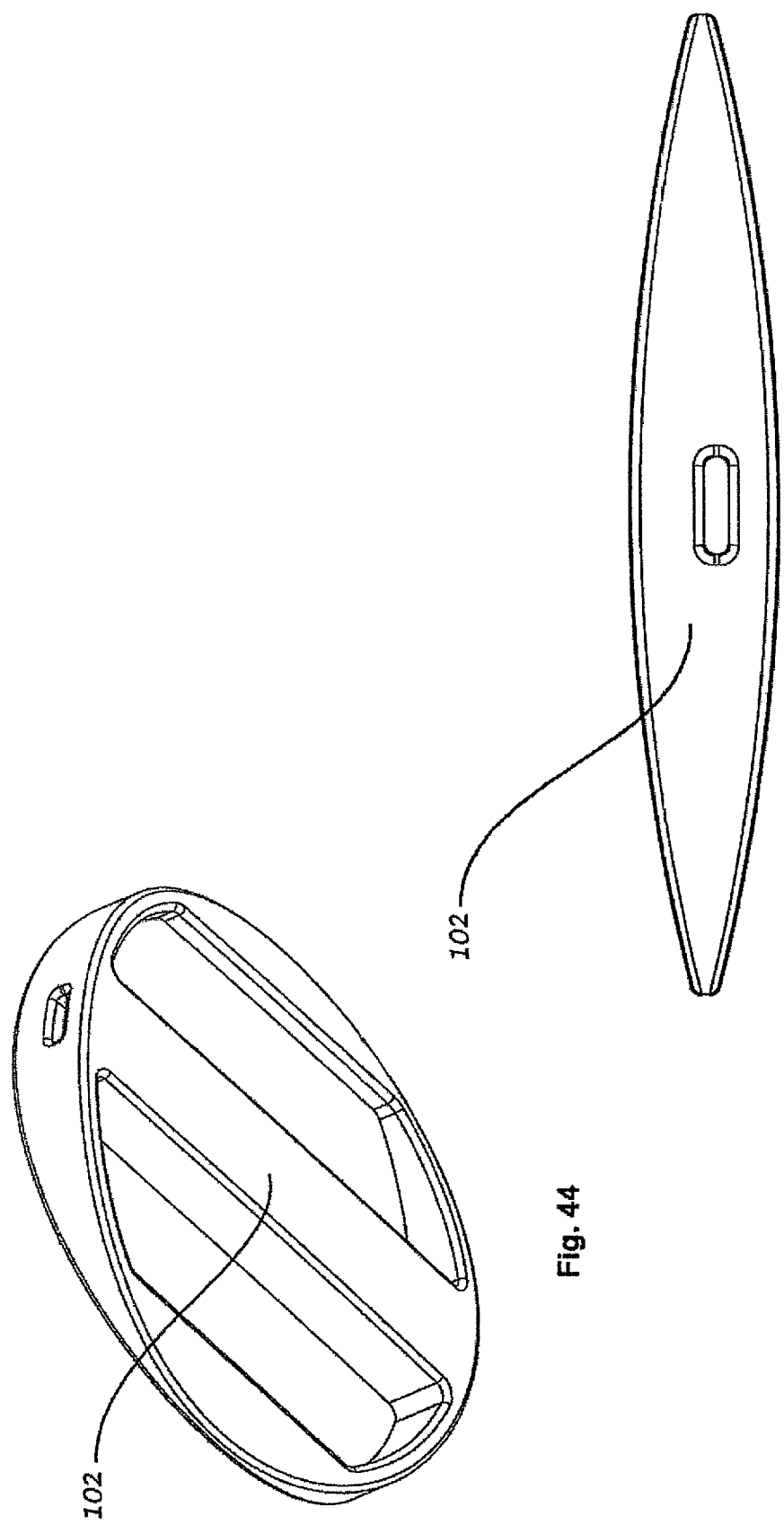

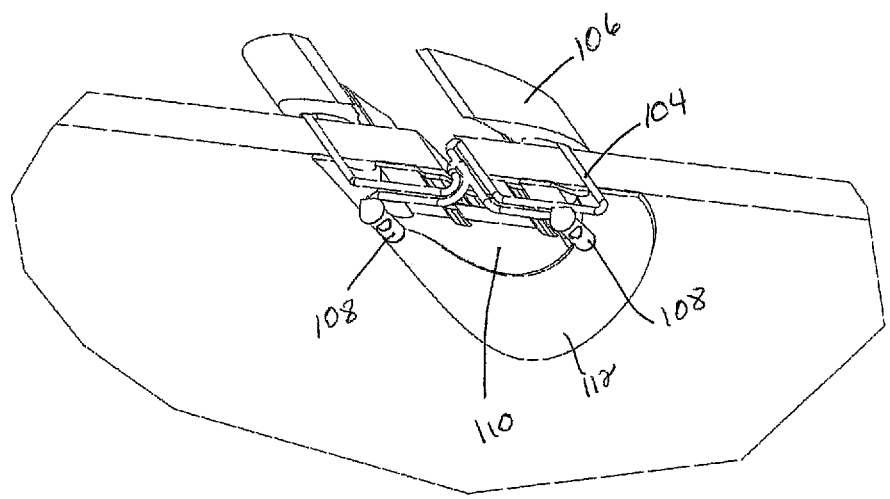
FIG. 72
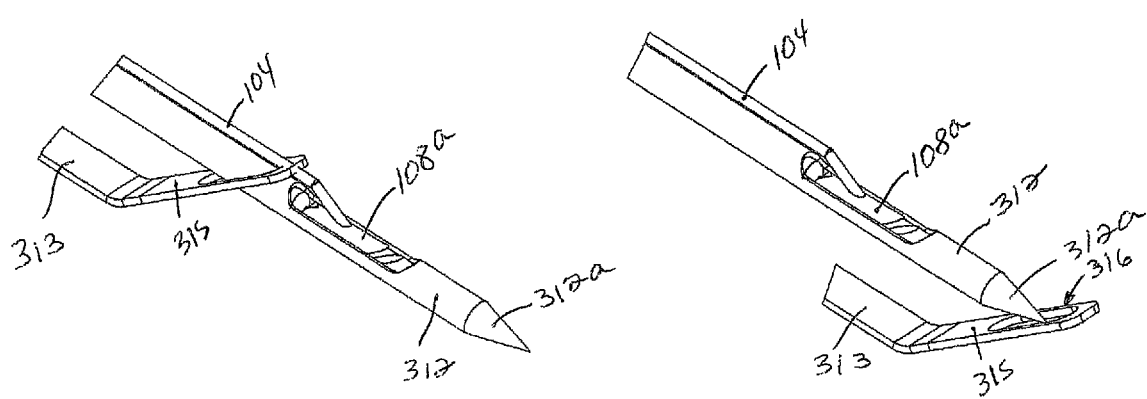
FIG. 74  FIG. 73

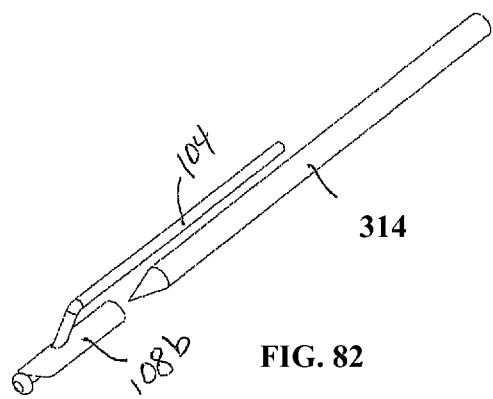
FIG. 82
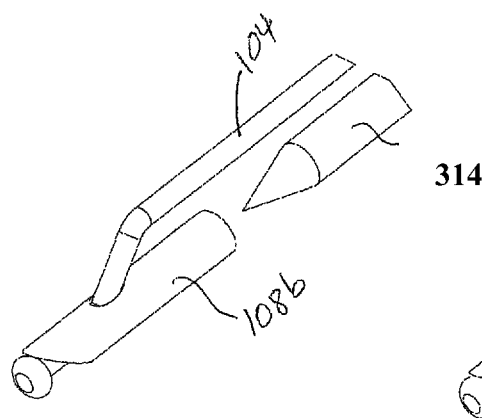
FIG. 83
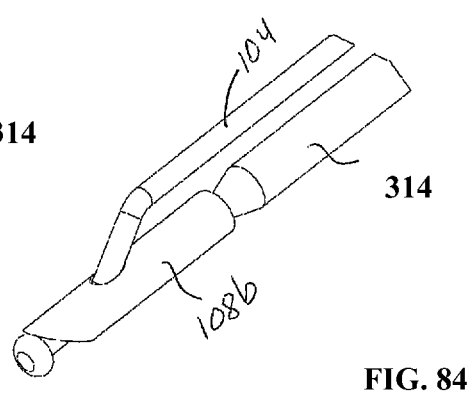
FIG. 84
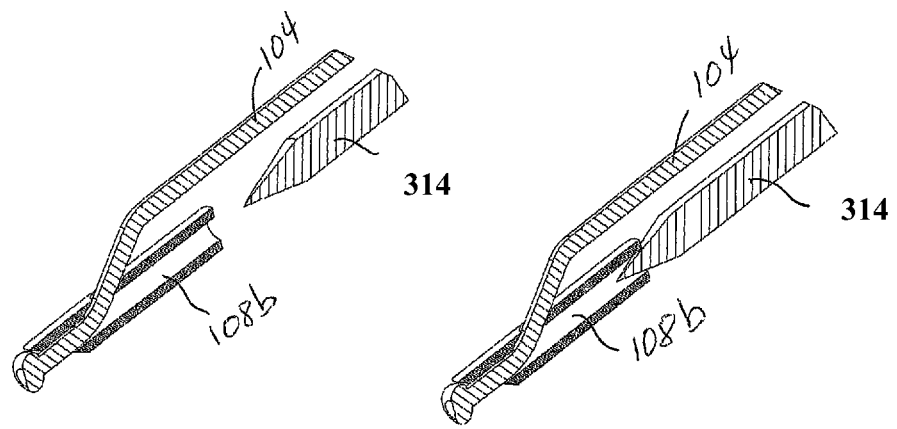
FIG. 85
FIG. 86

316

CLOSURE SYSTEM AND USES THEREOF

CROSS-REFERENCE TO RELATED APPLICATIONS

The present application claims priority to U.S. provisional patent application Ser. Nos. 61/291,132, filed Dec. 30, 2009, and 61/299,974, filed Jan. 30, 2010, the entirety of each of which is hereby incorporated herein by reference.

TECHNICAL FIELD OF THE INVENTION

The present invention relates generally to a closure system for use in surgical procedures.

BACKGROUND

Minimally invasive procedures are continually increasing in number and variation in part because such techniques offer an immediate advantage over more traditional, yet highly invasive surgeries. Endoscopic surgery, for example, uses one or more scopes inserted through small incisions for diagnosing and treating disease. In particular, endovascular surgery gives access to many regions of the body, such as the heart, through major blood vessels. Typically, the technique involves introducing a surgical instrument percutaneously into a blood vessel, such as, for example, the femoral artery. The currently emerging percutaneous endovascular procedures include aortic valve replacement, mitral valve repair, abdominal and thoracic aneurysm repair and tricuspid valve replacement. Other procedures requiring access to the femoral artery include coronary, carotid and cerebral angiographic procedures.

A key feature of these minimally invasive surgical procedures is the forming of a temporary pathway, usually an incision, to the surgical site. For example, in the emerging percutaneous endovascular procedures, an access site (e.g. incision) ranging from approximately 10 to 30 French units is formed as a temporary pathway to access the surgical site. Various instruments, such as procedural sheaths, guidewires and catheters, are then inserted through the access site, as well as specialized medical instruments, such as, balloon catheters and stents.

Currently, incision or access sites are routinely closed via cut-down surgical repair. This method is very invasive and fraught with complications. Accordingly, the rapid development of percutaneous endovascular surgery, of which interventional radiology and cardiology are a major component, has led to the need for instrumentation to minimize the risk of complications associated with closing the access site after a procedure.

SUMMARY OF THE INVENTION

The present invention provides a minimally invasive surgical closure system. In some embodiments, a provided closure system includes a method and apparatus for deployment of the closure system. Details of the closure system, and uses thereof, are described herein, infra.

BRIEF DESCRIPTION OF THE DRAWINGS

Certain features of a provided closure system are described in detailed herein below with reference to the figures, wherein:

FIG. 3 illustrates a tapered suture assembly having a distal needle tip and a proximal bolster, in accordance with embodiments of the present invention;

FIG. 4 shows an alternative view of the suture assembly depicted in FIG. 3;

FIG. 15 is an isometric side view of the intra-arterial foot of FIGS. 9-14 illustrating the flexible wing component folded within a delivery sheath;

FIG. 44 is illustrates an isometric view of yet another embodiment of the intra-arterial foot, in accordance with embodiments of the present invention;

FIG. 45 is an end view of the intra-arterial foot of FIG. 44;

FIG. 72 is a partial cross-sectional view of a closure device positioned on an arteriotomy, in accordance with embodiments of the present invention;

FIG. 73 is an isometric view of a needle driver, with a needle/suture subassembly attached thereto, advancing through an opening of a capture ribbon component, in accordance with embodiments of the present invention;

FIG. 74 is an isometric view of the needle driver of FIG. 73 advanced through the opening of the capture ribbon component;

FIG. 82 is an isometric view of the needle/suture subassembly of FIG. 81;

FIGS. 83 and 84 are enlarged views of FIGS. 82 and 79, respectively;

FIGS. 85 and 86 are enlarged views of FIGS. 81 and 80, respectively;

DETAILED DESCRIPTION OF CERTAIN EMBODIMENTS

Figure 1:
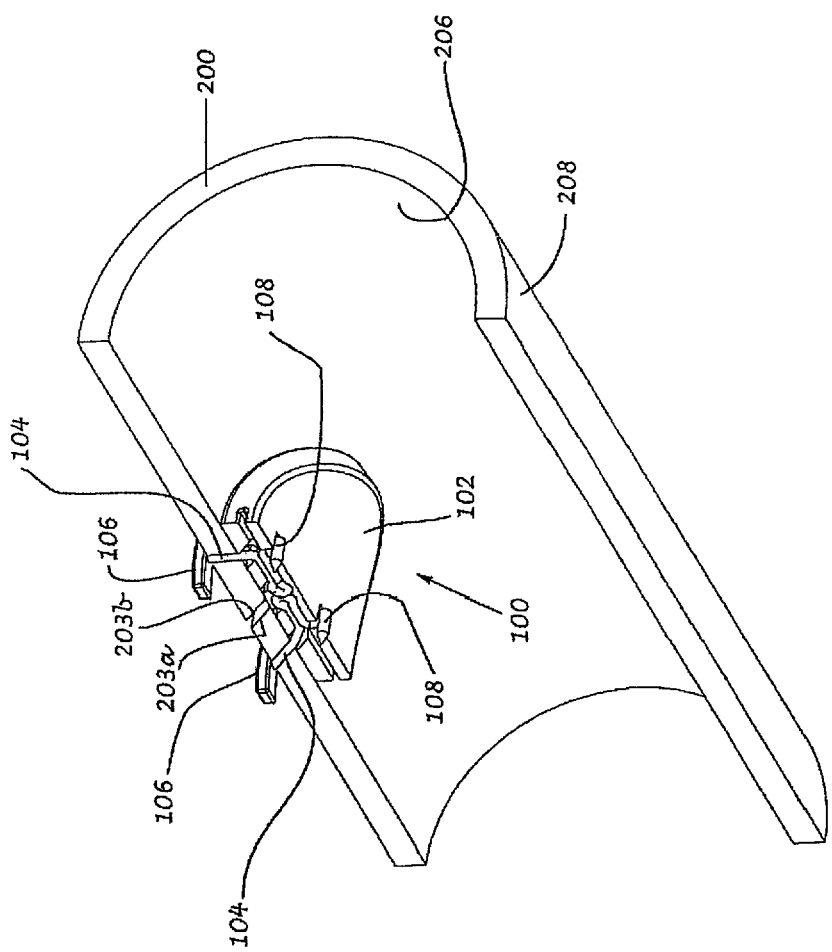
FIG. 1 is a cross-sectional perspective view of an artery having an arterial closure device positioned on a closed arteriotomy, in accordance with embodiments of the present invention.

1. General Description of Certain Embodiments of the Invention

As described herein, the present invention provides a surgical closure system (also referred to herein as a "device"). As such, a provided device is useful for closing a perforation (i.e., a hole, puncture, tear, rip, or cut, etc.) in any hollow vessel associated with a mammalian surgical procedure. One of ordinary skill in the art will appreciate that provided device is useful for closing a perforation in any lumen of a mammal, including the gastrointestinal tract (e.g., the stomach, intestines, colon, etc.), heart, peritoneal cavity, esophagus, vagina, trachea, bronchi, or a blood vessel.

Although certain figures and embodiments relate to use of a provided device for closure of a perforation associated with vascular surgery, one of ordinary skill in the art will appreciate that components of a provided device are not size dependent (i.e., are scalable) and are therefore useful for closure of any perforation in a lumen of a mammal.

In some embodiments, the present invention is directed to a closure system and method of percutaneous closure of an arteriotomy following an endovascular/intra-arterial procedures.

One of ordinary skill in the art will recognize that many mammalian lumina are comprised of one or more friable tissues. Thus, a common difficulty associated with surgical closure of a perforation in such lumina is that suture material typically causes tears in the friable tissue. Such tearing of the luminal tissue impedes healing and causes scarring. Indeed, such tearing of the friable tissues of the internal lumina of blood vessels can lead to scarring, dislodgment of tissue particles, blockage, or even eventual death of the patient. In view of the fragile nature of luminal tissues, an aspect of the present invention is to provide a device that affords dispersal of tension in suture material across the surface of a luminal tissue thereby allowing for closure of a perforation with minimum damage to the tissue.

With regards to the arterial wall morphology, the fibrous adventitial layer of an artery (i.e., the outer layer) is relatively tough, whilst the intimal and endothelial layers are friable. Because of the morphology of the arterial wall, an arteriotomy will normally be circumferential in nature and perpendicular to the longitudinal axis of the artery. In accordance with the present disclosure, a provided intra-arterial-foot prevents trauma and/or damage to the friable inner layer of the arterial wall by minimizing the amount of direct contact the sutures have with the inner layer. In addition, the intra-arterial foot distributes the tension in the sutures across the luminal surface. This closure configuration, i.e. controlling the alignment of the wound edges, and the absence of any transluminal impediments, ensures that the wound will heal expeditiously with minimal granulation tissue or scaring.

In certain embodiments, the present invention provides a closure system and method of percutaneous closure of arteriotomies following endovascular/intra-arterial procedures. In some embodiments, a closure device includes an intra-arterial foot positioned against a luminal surface of an arteriotomy; at least one suture positioned within the intra-arterial foot for securing the intra-arterial foot into position, the at least one suture having a proximal end and a distal end; at least one extra-arterial bolster attached to the proximal end of the at least one suture, the at least one extra-arterial bolster secured on an adventitial surface of the arteriotomy; and at least one needle attached to the distal end of the at least one suture, the at least one needle anchored on a posterior portion of the intra-arterial foot such that a tensile force is applied to the suture, the suture securing the intra-arterial foot into position. In some embodiments, the suture is doubled up within the intra-arterial foot. The at least one needle delivers the at least one suture through an arterial wall to a posterior side of the intra-arterial foot. In some embodiments, the intra-arterial foot, the suture, the bolster and the needle are all bio-absorbable.

In some embodiments, a closure device is comprising: a foot positionable against a luminal surface of an arteriotomy, the foot having an internal channel; a suture positionable within the foot for securing the foot against the luminal surface; and a bolster attached to a proximal end of the suture, the bolster positionable on an adventitial surface of the arteriotomy, the suture is fitted within the internal channel by a tensile force applied to the suture. In certain embodiments, a provided device further includes a needle on a distal end of the suture. The needle guides the suture through the internal channel and to the posterior side of the foot. Moreover, the bolster tethers the foot against the luminal surface in response to the tensile force. Either some or all of the components of this embodiment of the closure device, namely the foot, the suture and the bolster, is biodegradable.

As described in detail herein below, the closure system of the present disclosure includes two principal subassemblies, namely, a delivery device and a closure device. The delivery device is introduced via a delivery sheath that is already in situ after a given procedure. The delivery device delivers and positions the closure device in the arteriotomy, closing the arteriotomy. The closure device includes an intra-arterial foot component, tethering sutures, needle tips and extra-arterial bolsters. In accordance with the present disclosure, in the final closure dynamic of the closure device, the intra-arterial foot is positioned against a luminal surface juxtaposed to the arteriotomy of a vessel. The sutures reside within an interference fit (e.g. a channel) of the intra-arterial foot, and secure the intra-arterial foot into position (i.e. against the luminal surface of the vessel). The bolsters are positioned on the adventitial or external surface of the artery and the needle tips are positioned on the underside of the intra-arterial foot and, in some embodiments, oblique to the intra-arterial foot surface to provide an anchor for the sutures.

The delivery device includes a foot anchor initially anchored to the intra-arterial foot during the delivery of the intra-arterial foot into the internal lumen of the artery, a wound spreader for spreading the wound edges of the arteriotomy and needle drivers to drive the needle/suture subassembly into a capture and release ribbon component. The capture and release ribbon components are adapted for tensioning the suture securely within the channel in the intra-arterial foot and for releasing the suture after the tensioning, in a manner described in detail herein below.

In one embodiment, the wound spreader component is oriented transverse to the artery and is positioned adjacent to the foot anchor. In particular, the wound spreader includes an elliptical configuration, with the major axis corresponding to an outermost diameter of the intra-arterial foot. In addition the major axis of the elliptical configuration is at least the same as the circumference of the delivery sheath. During delivery of the intra-arterial foot, the wound spreader aids the spreading of the wound edges of the arteriotomy, guiding the arteriotomy to conform to its elliptical configuration. Thus, the wound spreader controls the geometry of the arteriotomy, helping minimize blood loss into the surrounding tissue.

In some embodiments, a provided closure system comprises a foot portion, a wing portion, a suture, one or more bolsters, and a needle/shuttle, and various combinations thereof. In certain embodiments, a provided closure system further comprises a handle and deployment mechanism. Details of components associated with a provided closure system are set forth, infra, and, in certain embodiments, as depicted in the accompanying Figures.

2. Components of a Provided Device a. Foot

As used herein the term "foot", used alone or in combination, for example as "intra-arterial foot," refers to a component of a provided closure system that can act as an anchor for securing other components of the system. For example, a provided foot can secure a suture and support a wing component (described below). In certain embodiments, a provided intra-arterial foot supports wound edges and minimizing the amount of direct contact the sutures have with a luminal surface of an artery. In some embodiments, a provided intra-arterial foot distributes suture tension across a luminal surface of an arteriotomy.

In some embodiments, a provided intra-arterial foot can be a tamponade for controlling bleeding during a delivery of the closure device. The arteriotomy includes a wound having at least two edges. The intra-arterial foot helps maintain the two wound edges in apposition via the suture assembly securing the foot in place with respect to the wound edges. The suture resides, and is substantially retained, within the intra-arterial foot and thus limits suture contact with the tissue in the proximity of the arteriotomy.

In another embodiment, a provided foot includes a channel that locks the suture into place. Alternatively, an interference fit between the suture and the intra-arterial foot locks the suture into place.

In some embodiments, a provided foot includes a first portion having at least one opening for facilitating delivery of a suture; and a flexible second portion associated with the first portion, where the first portion and the second portion create a tamponade effect on a wound (e.g., of an arteriotomy). The first portion is a central core component for providing structural integrity of the foot and the second portion is a flexible wing component. The suture tethers the first and the second component against a luminal surface of a vessel.

In some embodiments, a first portion of the intra-arterial foot includes a diameter that is less than a diameter of the arteriotomy and a second portion includes a diameter that is greater than the diameter of the arteriotomy. In one embodiment, the first and the second portions include an absorbable porous material, where the absorbable porous material may include electrospun polyglycolic acid (PGA), polyglycolic/lactic acid (PGLA), Polyurethane (PUR) and polydioxanone (PDO). In other embodiments, the first and the second portions are radiopaque.

In certain embodiments, the first and the second portions have a circular configuration. In other embodiments, the first and second portions are manufactured as a single component. In some embodiments where the first and the second portions have circular configurations, the first portion includes a uniform thickness and a flat profile. Alternatively, the first portion may include a circular profile and uniform thickness or varying thickness. In some specific embodiment, the first portion includes a circular profile and varying thickness having at least one hollowed out portion.

In a second embodiment of the intra-arterial foot, the foot includes a central core having at least one opening for facilitating delivery of a suture, the central core having a diameter less than a diameter of an arteriotomy; and a flexible wing associated with the central core, the flexible wing positionable on a luminal surface of an arteriotomy and the flexible wing creating a tamponade.

The step of deploying the flexible portion of the foot includes disposing the flexible portion from a substantially folded first position to a deployed second position. In one particular embodiment, the flexible portion of the foot is substantially larger than a diameter of the arteriotomy.

In one embodiment of the present disclosure, the intra-arterial foot functions as a tamponade to control bleeding during the delivery of the closure system. In addition, the intra-arterial foot protects the friable intimal and endothelial layers of the artery from the sutures. In particular, the intra-arterial foot retains the suture substantially within itself, thus limiting suture contact with any tissue in the proximity of the arteriotomy. In accordance with the present disclosure, the intra-arterial foot maintains the alignment of the arteriotomy wound edges and acts as a scaffold to accurately hold (and align) the wound edges into apposition during and after tightening of the sutures. That is, the intra-arterial foot in concert with the suture assembly brings and maintains the two wound edges together in substantial alignment, as opposed to avert (i.e. turned out), invert (i.e. turned in) or overlap of the wound edges as the suture assemblies secure the foot in place. The apposition of the wound edges is advantageous to promote primary intent wound healing (i.e. healing by first intention). As is well known, primary intent healing is full thickness healing which results in minimal scaring or granuloma within the healing wound. However, in accordance with the present disclosure, direct apposition of the wound edges is not necessary for effective closure since apposition may not occur in all instances due to many factors including, for example, the disease state of the vessel.

Intra-arterial foot houses the sutures once tensioned. In particular, the sutures are partially positioned within a slot of the intra-arterial foot in a folded manner such that each one is at least twofold within the intra-arterial foot. Moreover, the tensioned, folded suture occludes the slot of the intra-arterial foot thereby assisting in the prevention of blood loss through the slots. The distal end of each of the sutures is attached to a corresponding needle tip and the proximal end is attached to a corresponding bolster. As such, the needle tip acts as an anchor to allow tensioning of the bolsters. More in particular, the suture and bolster together securely tether the intra-arterial foot to the luminal surface of the artery. The bolster, in particular, distributes a tensile force applied to the suture laterally across the arterial surface and parallel to the wound edges of the arteriotomy, thus ensuring an evenly distributed force along each wound edge of the arteriotomy to effect a secure closure of the arteriotomy as and after the wound edges are brought into apposition at least in part by the force exerted through the bolster. Moreover, the intra-arterial foot distributes the resulting force of the suture tension on the luminal surface of the artery. The distal needle tip is adapted to deliver the suture through the arterial wall to the posterior side of the intra-arterial foot and to anchor the distal end of the suture to the intra-arterial foot. In particular, the distal end of the suture is attached to a central portion of the needle tip thus forming a "T" configuration.

Thus, the closure system of the present disclosure provides an active and secure closure of wound edges of an arteriotomy. Healing of the arteriotomy is expedited because the wound edges are aligned and because the transluminal components are minimized and in some embodiments non-existent. Moreover, all friable tissues are shielded from any tension on the sutures. With regards to the sutures, the suture-based closure accommodates infinitely different anatomies. The closure system exploits arterial wall morphology and uses the adventitial layer for anchoring. In the final closure dynamics, all intra-arterial components are tethered to arterial wall.

b. Wing

In certain embodiments, a provided device includes a flexible wing component. In some embodiments, the wing is substantially circular. In certain embodiments, the wing is elliptical. In certain embodiments, the wing is positionable against a provided foot for use as a wound occluder. In such embodiments, the wing is positionable against a luminal surface and the foot is positionable against the internal surface of the wing.

In one embodiment, the foot includes a flexible wing, the wing movable from a folded first position within a delivery device to a deployed second position within an artery. It will be appreciated that a flexible wing component can be integrally formed with a provided foot or can be a separate component used in conjunction with a provided foot.

In some embodiments, the second portion of the intra-arterial foot forms a seal with a portion of an arteriotomy. In addition, the second portion is adapted for movement between a first position substantially folded about the first component and a second position that is at least partially deployed. Alternatively, the second portion is adapted for movement from a substantially folded first position to a deployed second position. In particular, the second portion is at least partially folded within a delivery sheath and at least partially open when the second portion is advanced through the delivery sheath. In one embodiment, the second portion is elliptical in shape, where the second portion is wider in the latitudinal or transverse direction relative to a longitudinal axis of the artery. In this particular embodiment, the minor diameter of the ellipse is larger than a diameter of the arteriotomy.

In some embodiments, a provided wing includes a plurality of patterned holes or, alternatively, slots and a midsection. In other embodiments, a provided wing includes a plurality of latitudinal parallel slots and a non-porous midsection. In one particular embodiment, a provided wing includes a plurality of longitudinal parallel slots and a midsection. In another particular embodiment, a provided wing includes a plurality of profiled patterned openings and a non-porous midsection. In yet another embodiment, a provided wing includes a plurality of profiled slots and a non-porous midsection. Alternatively, a provided wing may include a plurality of patterned holes and a non-porous border about an edge thereof. A provided wing having a plurality of patterned holes and a solid non-porous midsection is also envisioned.

c. Suture Bolster

As used herein, the term "bolster" refers to a device component attached to a proximal end of a suture. The bolster ultimately is positioned at the outer surface of the vessel for closure. For example, in the case of an arteriotomy, a bolster is positionable at a fibrous adventitial layer of an artery (i.e., the outer layer).

In certain embodiments, an extra-arterial bolster is tethered to an adventitial surface of an arterial wall. In addition, the at least one needle is tethered to the intra-arterial foot and the intra-arterial foot is tethered to the luminal surface of the arterial wall.

In accordance with the present invention, a tensile force is applied to the suture, generating suture tension. In some embodiments, the suture tension effects active closure of the arteriotomy. In particular, the intra-arterial foot secures the suture in response to the tensile force. Moreover, the tension on the suture causes the extra-arterial bolster to securely tether the intra-arterial foot to the luminal surface layer of the artery. In one embodiment, the extra-arterial bolster distributes the suture tension laterally across the arterial surface and parallel to the at least two wound edges of the arteriotomy. In particular, the extra-arterial bolster evenly distributes the tensile force along each of the plurality of wound edges of the arteriotomy to effect a secure closure. In addition, the extra-arterial bolster distributes the suture tension on the adventitial surface of the artery with a resulting force aligning the at least two wound edges. In one particular embodiment, the suture tension on the adventitial surface of the artery results in a force bringing the at least two wound edges into direct apposition. The needle-tip acts as an anchor in response to the suture tension such that tension is applied between the at least one extra-arterial bolster and the intra-arterial foot.

In one particular embodiment, the method includes effecting, by the tensile force, closure of an arteriotomy. The tensile force tethers the at least one suture. In addition, the foot, which may include distinct wing and core components, helps seal and reinforce the arteriotomy in response to the tensile force.

d. Needle and Suture Shuttle

The needle, suture, and shuttle may take on various configuration in various embodiments disclosed herein. Generally, the needle will reference the mechanism piercing and/or penetrating one or more of the vessel wall, the intra-arterial foot, and any ribbons disposed therein. The shuttle generally references the item attached to an end of the suture. In some embodiments, the tip of a needle may be the shuttle, and hence may be attached to the suture. In other embodiments the shuttle may be distinct from the needle and/or housed within, or on the needle and may be separated from the needle after penetrating the intra-arterial foot.

In one particular embodiment, the suture includes a tapered section. In addition, the suture is, inter alia, either a single monofilament or a braided suture. The suture, tapered or not, and the needle form a "T" configuration. In particular, the needle is rotatable to and from a "T" configuration with the suture. More in particular, the needle rotates to form a "T" configuration with the suture when the needle is ejected from a driving member.

The needle includes a body and a proximal spherical tip. The body includes an opening for receiving a portion of the suture therewithin. In one embodiment, the opening includes a conical shape having a first diameter smaller than a second diameter, the smaller diameter securing the suture. In another embodiment, the needle includes a shoulder and the body includes a raised portion tapering from the shoulder to a proximal end of the needle. In this particular embodiment, the raised portion is engageable with a slot within the driving member. Moreover, the raised portion is tapered to reduce the profile of the needle and the suture.

In another embodiment, the needle includes a shoulder and a penetrating tip, where the shoulder is positionable on a distal portion of the driving member. In this embodiment, the suture shelters behind the shoulder.

In yet another embodiment, the needle includes an elliptical profile. In this particular embodiment, the elliptical profile reduces a profile of the needle in a longitudinal axis. In addition, the elliptical profile increases a surface area of the needle for securing the needle to the posterior side of the intra-arterial foot.

The needle includes a body having an opening for receiving a portion of a suture; and a conical distal end attached to the body. A portion of the body and the conical distal end is tapered flat. In some embodiments, the needle includes one of an elliptical profile and a cylindrical profile. Alternatively, the needle includes a flat edge. The conical end includes a shoulder, the shoulder resting in a distal portion of a driving member. The conical end may sometimes include a penetrating tip. In one particular embodiment, the conical end of the needle includes a shoulder and a penetrating tip, the shoulder resting on a distal portion of a driving member. In another embodiment, the conical end includes a raised portion tapering from the conical distal end to a proximal end of the body.

The needle drivers are positioned parallel to the foot anchor and are advanced distally to drive the needle/suture subassembly through an opening of a capture and release ribbon component. The capture and release ribbon component captures the needle/suture subassembly and applies a tensile force to move and secure the suture into the channel of the intra-arterial foot. The "T" configuration of the needle/suture subassembly needle anchors the needle tip to the underside of the intra-arterial foot while the suture is secured within the channel. After the suture is secured within the channel, the ribbon component releases the suture and retracts into the delivery device.

3. Aspects of the Invention Embodied by the Figures

Other aspects, features and advantages of the presently disclosed closure system and methods of percutaneous closure of arteriotomies following endovascular/intra-arterial procedures will become apparent from the following detailed description taken in conjunction with the accompanying drawing, which illustrate, by way of example, the presently disclosed system and method.

Referring now to the drawing figures, wherein like references numerals identify similar, identical or corresponding elements, an embodiment of the presently disclosed closure system is described. The closure system, in accordance with the present disclosure, provides for a minimally invasive, percutaneous mechanical closure of arteriotomies, while substantially reducing the length of time needed to perform the closure.

Figure 2:
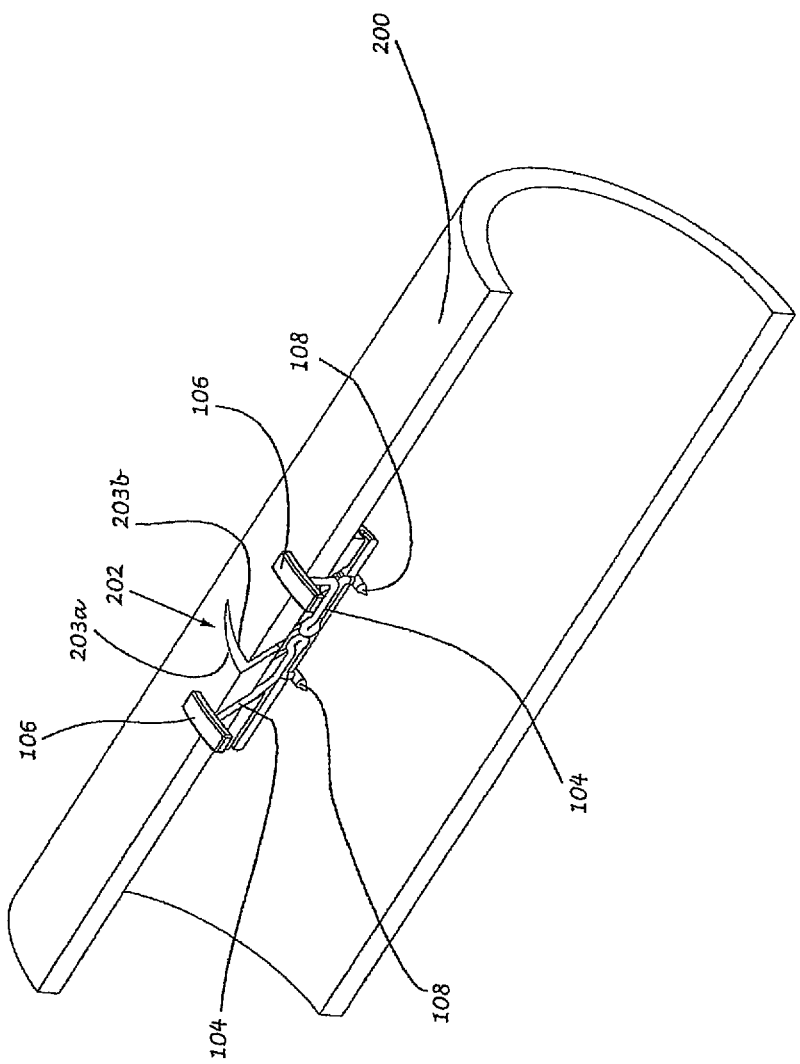
FIG. 2 is a cross-sectional perspective view of the artery and arterial closure device depicted in FIG. 1.

FIGS. 1 and 2 illustrate an exemplary closure device 100 in the final closure position with respect to an arteriotomy 202 of a sectioned artery 200. Closure device 100 includes an intra-arterial foot component 102, tethering sutures 104, extra-arterial bolsters 106 and needle tips 108. Closure device 100 is adapted for active and secure closure of wound edges of an arteriotomy 202, in a manner described in detail herein below.

In some embodiments, the intra-arterial foot is a single-piece foot, as depicted by foot 102. Foot 102 is tethered into position by two independent sutures 104, two extra-arterial bolsters 106, and two needle tips 108. In particular, each suture 104 includes an extra-arterial bolster 106 attached to its proximal end and a needle tip 108 attached to its distal end. During the delivery of closure device 100, the needle tips 108 are inserted through an arterial wall 204 such that sutures 104 penetrate the wall and pass through to the posterior side of the single-piece intra-arterial foot 102. Additionally, needle tips 108 anchor the distal end of sutures 104 to an underside of intra-arterial foot 102, in a manner described in detail herein below. As illustrated by the figures, when the sutures are situated in their final position according to some embodiments of the present invention the two sutures are oriented in a mirrored configuration.

FIGS. 3 and 4 illustrate a suture 104 having a needle tip 108 on a distal end of suture 104 and a bolster 106 on the proximal end of suture 104. Needle tip 108 and bolster 106 are attached to suture 104 using techniques well known in the art, such as, for example, bonding, using a glue/adhesive, heat staking, tying off the suture behind the particular component, over-molding, or a combination of these processes. Suture 104 is continuous between bolster 106 and needle tip 108. In accordance with embodiments of the present invention, bolster 106 secures the suture to the arterial wall 204 and needle 108 secures the suture to the intra-arterial foot 102, thus securing intra-arterial foot 102 to luminal surface of the arteriotomy site. In particular, applying tension to the suture 104 brings the wound edges 203a and 203b into alignment and tethers the intra-arterial foot 102 to the lumen 206 of artery 200 to effect closure of arteriotomy 202.

Figure 9:
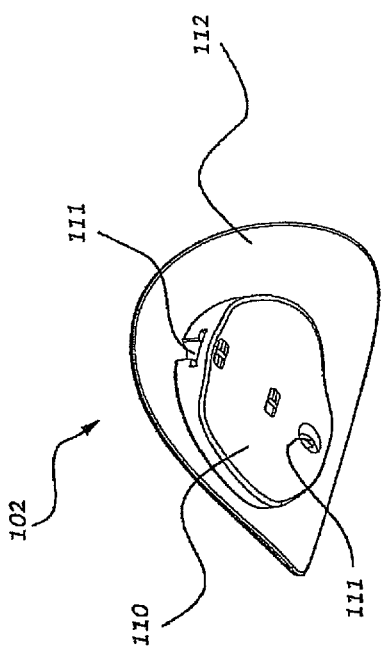
FIG. 9 is an isometric view of an intra-arterial foot and wing, in accordance with embodiments of the present invention.
Figure 10:
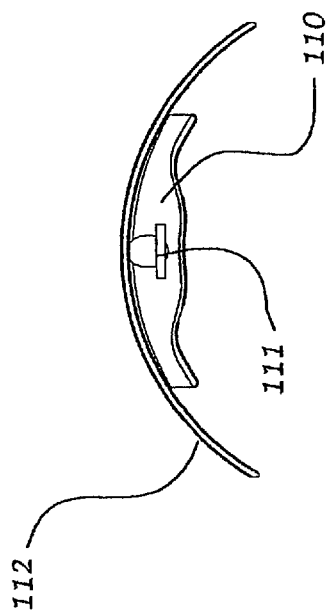
FIG. 10 is an end view of the intra-arterial foot and wing shown in FIG. 9.
Figure 11:
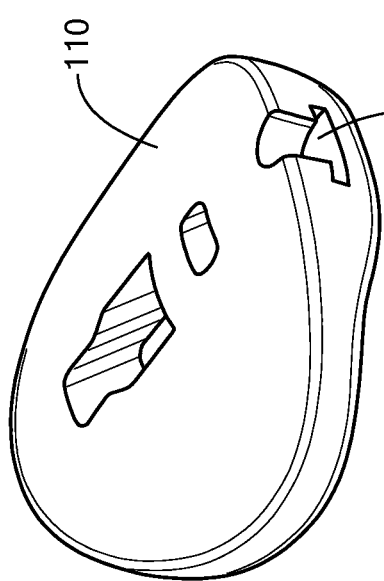
FIG. 11 is an isometric view of a central core component of the intra-arterial foot shown in FIGS. 9 and 10.
Figure 14:
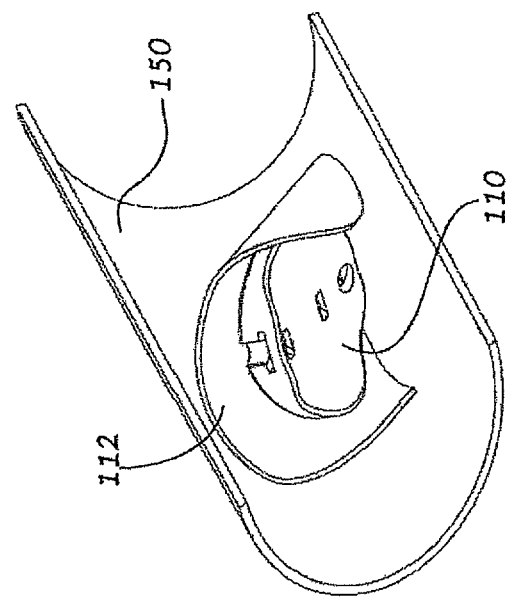
FIG. 14 is an isometric side view of the intra-arterial foot of FIGS. 9 and 10 positioned within a sectioned delivery sheath.
Figure 13:
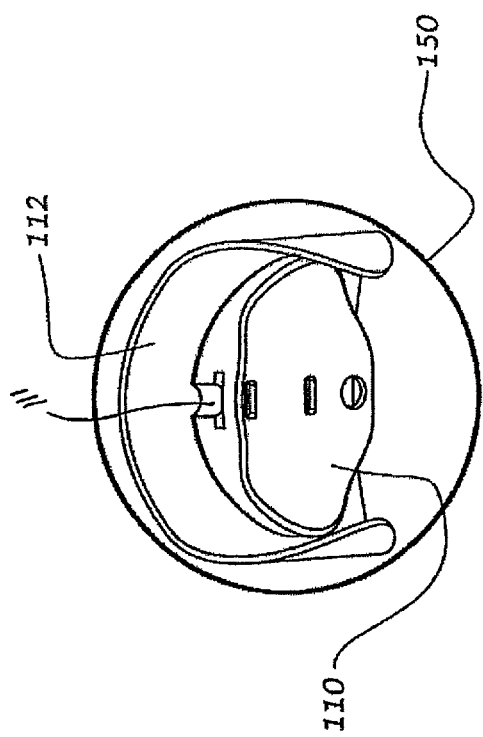
FIG. 13 is an isometric end view of the intra-arterial foot of FIGS. 9 and 10 positioned within a delivery sheath.

In some embodiments, suture 104 includes a regular section 105a, a tapered section 105b and an enlarged section 105c. Section 105b is tapered to increase the interference fit within the intra-arterial foot 102, in a manner described in detail herein below. In some embodiments, suture 104 includes a single monofilament and tapered section 105b may be achieved by means of a bump-extrusion, coating or sleeve. In other embodiments, suture 104 is a braided suture, where tapered section 105b is attained by reducing the strands in the braid or by braiding over a tapered mandrel. One method of anchoring the tensioned sutures within the intra-arterial foot 102 is by forming a channel 111 and by using an interference fit between the suture and cavities (e.g. channel 111) within the intra-arterial foot 102 (FIGS. 9-11). The compression of the interference fit can be increased by means of a tapered suture, as illustrated by FIG. 3. As discussed herein, some embodiments of the present invention incorporate a suture having a uniform thickness.

Suture 104 provides flexibility with respect to differing arterial wall thickness and other variations in anatomy. Additionally, suture 104 infers variability of tensioned length, that is, suture 104 provides flexibility to all sizes of artery 200. By contrast, a purely mechanical application of intra-arterial foot 102 would fit some arteries, but may be excessively loose or tight on other arteries. Moreover, as suture 104 is continuous, it does not require tying or cutting thus eliminating an extra process step. Also, the continuous suture 104 securely anchors the intra-arterial foot 102 to the luminal or internal surface 206 of arteriotomy 202 in a fail-safe manner.

Figure 5:
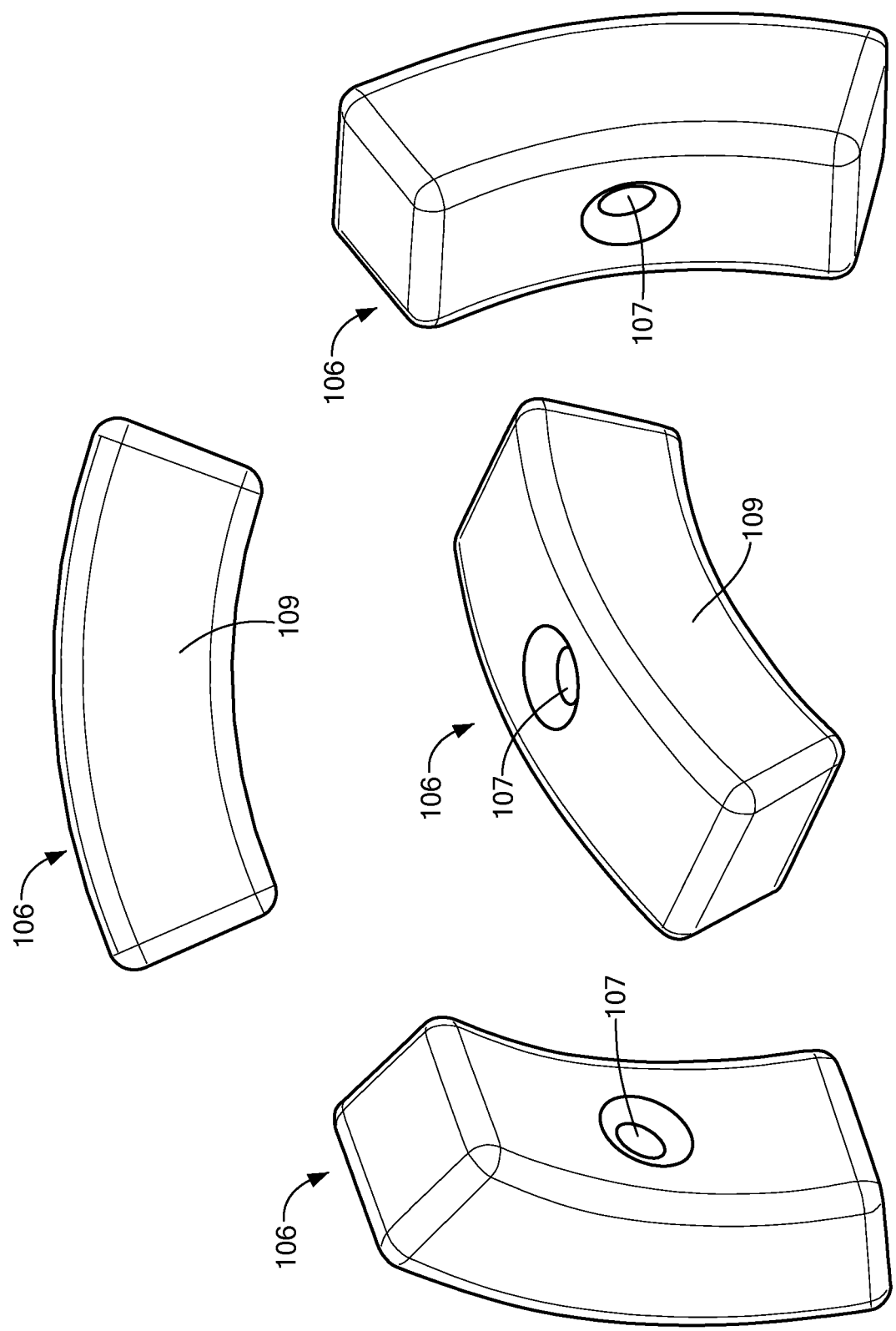
FIG. 5 illustrates views of a bolster component, profiled to match the curvature of an arterial surface, in accordance with embodiments of the present invention.

With reference to FIG. 5, in conjunction with FIGS. 3 and 4, bolster 106 is attached to a proximal end of suture 104. The function of bolster 106 is to securely tether intra-arterial foot 102 to the luminal layer 206 of artery 200. In some embodiments of the present invention, bolster 106 is designed to distribute a tensile force applied on suture 104 over a large surface area and parallel to the wound edges 203a and 203b of the arteriotomy 202. Distributing the pressure resulting from the tension applied to the suture ensures that the adventitial or external surface 208 of artery 200 is not damaged. Furthermore, the tension in the suture actively and securely brings the wound edges 203a and 203b into alignment with the intra-arterial foot to ensure proper alignment of the opposing edges without requiring insertion of any foreign material between the wound edges. As illustrated by the figure, bolster 106 includes an opening 107 for receiving the proximal portion of suture 104 and a profiled, arched section 109 for engaging the exterior surface 208 of artery 200.

Figure 6:
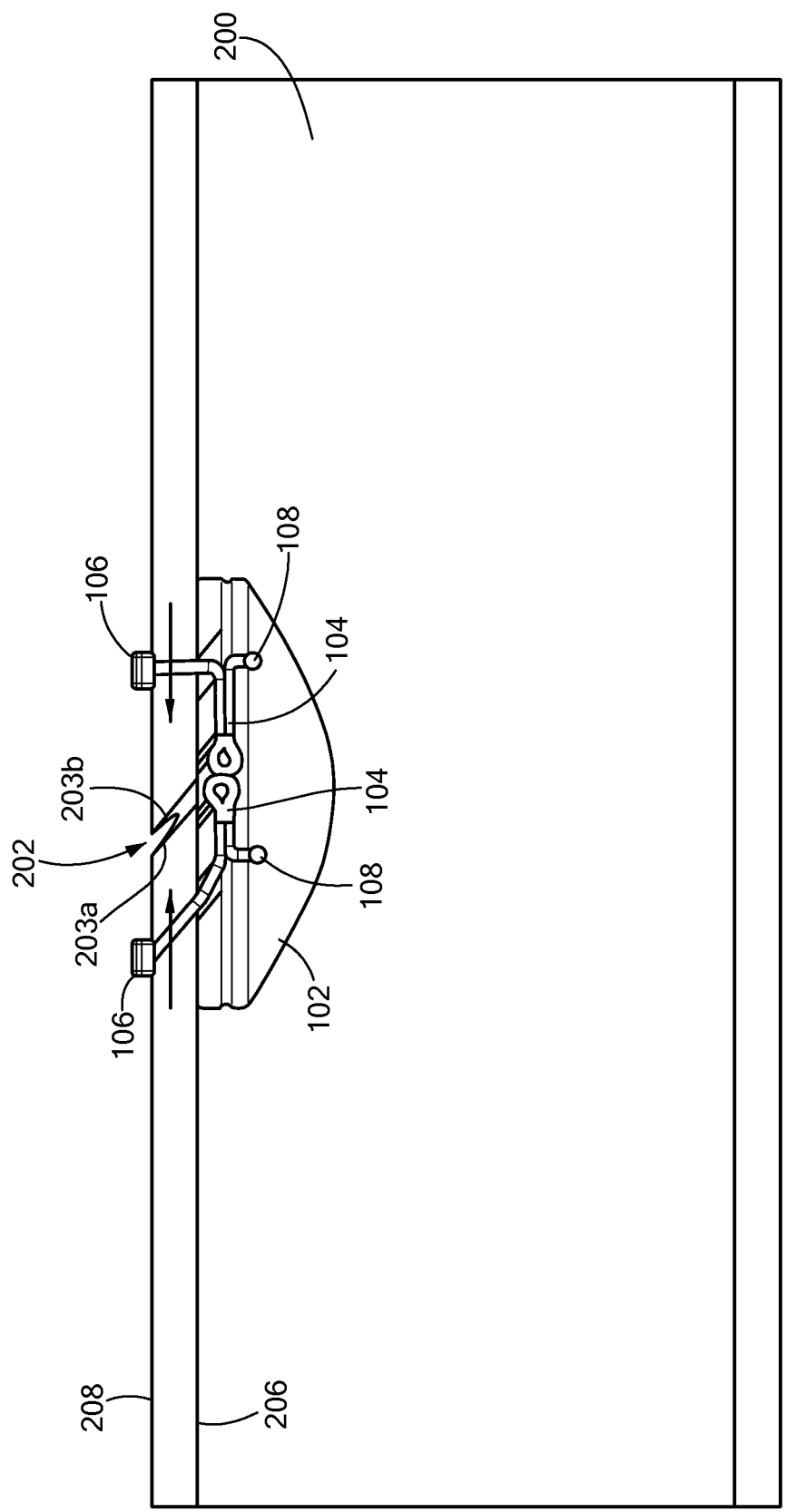
FIG. 6 is a cross-sectional side view of the artery and arterial closure device shown in FIGS. 1 and 2.
Figure 7:
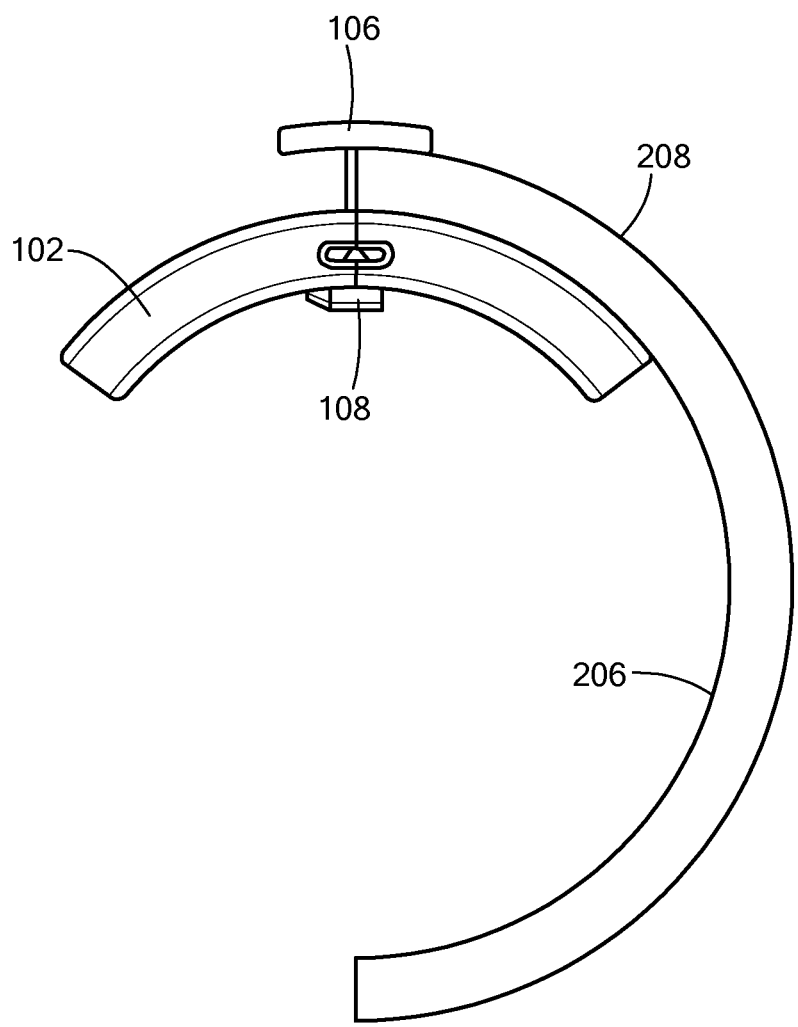
FIG. 7 is an end view of the artery and arterial closure device shown in FIGS. 1, 2, and 6.

With reference to FIGS. 6 and 7, in conjunction with FIGS. 1 and 2, during closure of arteriotomy 202, needle tip 108 drives suture 104 through a channel 111 within intra-arterial foot 102, in a manner described in detailed herein below with reference to FIGS. 64 and 65. Extra-arterial bolsters 106 are positioned on the adventitial surface 208 of artery 200 by applying a tensile force on suture 104, which pulls suture 104 into channel 111 of intra-arterial foot 102 and secures the intra-arterial foot to lumen 206. As illustrated by the figures, suture 104 is doubled up within the channel 111. As such, when tension is applied to the suture 104 to position extra-arterial bolster 106 in place, this tensing movement brings wound edges 203a and 203b into alignment and maintains the alignment as channel 111 in intra-arterial foot 102 locks sutures 104 into place.

With particular reference to FIG. 6, as bolster 106 makes contact with the adventitial surface 208 of the artery 200 and tension is constantly applied to both sutures 104 they actively pull the edges 203a and 203b of arteriotomy 202 into alignment (depicted by the directional arrows), with the intra-arterial foot 102 providing a scaffold to ensure accurate alignment of the wound edges. This securely closes the arteriotomy and provides the optimal closure for primary intent healing of the arteriotomy. It is noted that FIG. 6 illustrates bolster 106 in their final position on the surface of artery 200, where the arteriotomy 202 is effectively closed.

Figure 8:
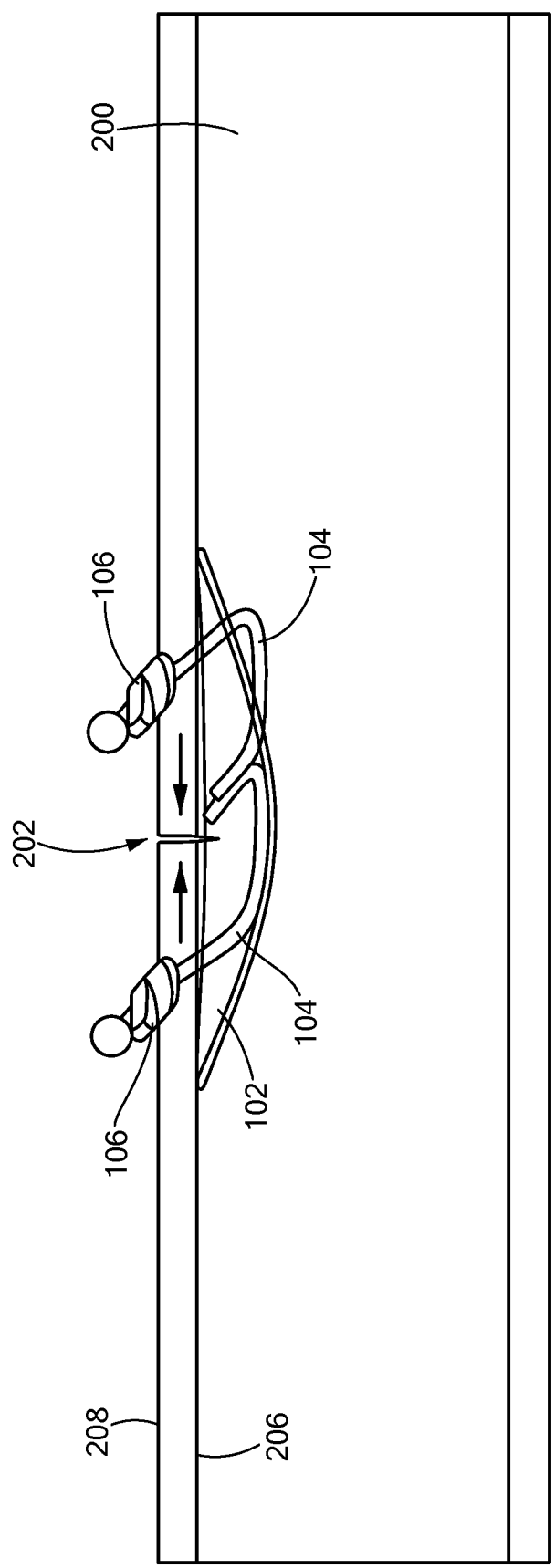
FIG. 8 is a cross-sectional side view illustrating an arterial closure device positioned on a closed arteriotomy, in accordance with embodiments of the present invention.

FIG. 8 describes an alternative configuration with respect to the distribution of the suture tension to affect an active closure of the arteriotomy 202. In this particular embodiment, the basic configuration of closure device 100 is similar to that shown in FIGS. 1 and 2; however, the sutures within intra-arterial-foot 102 include the bolsters attached to the proximal ends, but do not include the needle-tips. As shown by the figures, a bolster is attached to the proximal end of each suture and the distal end of each suture resides within intra-arterial foot 102. An interference fit between suture 104 and intra-arterial-foot 102 secures the sutures to maintain tension on each one of the extra-arterial bolster 106. It is noted that the sutures 104 do not contact the inner lumen surface except for at the point of penetration or transluminal tissue across the arteriotomy in some embodiments, thereby eliminating the risk of damaging the tissue around the incision site due to point loading of a suture directly contacting the tissue. In some embodiments, the folded suture loops may be pulled through an opening at the top of the foot and out of arteriotomy. Although the closure device in the embodiment shown in FIG. 8 does not include a needle tip, embodiments of the present invention include a needle tip that guides the suture into place. In such embodiments, the needle tip is maneuvered through the delivery shaft and removed from the distal end of the suture.

The materials used in the components of the presently disclosed closure system generally include materials that are bioabsorbable. In the following description, any details regarding specific materials are for exemplary purposes only and are not intended to be limiting. Therefore, it is to be understood that the recitation of any material or material property in this disclosure is not to be limited to those precise materials or properties.

Suture 104 may be a standard polyglycolic acid (PGA), polydioxanone (PDO) or a polyglycolic/lactic acid (PGLA) 9010 copolymer. Monofilament and multifilament sutures may be utilized. Alternatively, suture 104 may be composed of many off the shelf absorbable suture. However, it is noted that the material should allow the suture to be flexible.

Bolster 106 may be manufactured from the same absorbable material as suture 104. In one particular embodiment, for example, the material is a blend of 82:18 PLA/PGA or a blend of 15% 5050 DLG 1A and 85% of 8218 LG 13E. In other embodiments, bolster 106 may be a standard PGA, PGLA, Polyurethane (PUR) and polydioxanone (PDO).

With reference to FIGS. 9-12, another embodiment of intra-arterial foot 102 will now be described in detail. In this particular embodiment, intra-arterial foot 102 is a two-piece foot having two functional elements, namely a central core component 110 and a flexible wing 112. In accordance with the present disclosure, flexible wing 112 folds within a delivery sheath for ease of delivery of intra-arterial foot 102 into the lumen of the artery 200.

Figure 12:
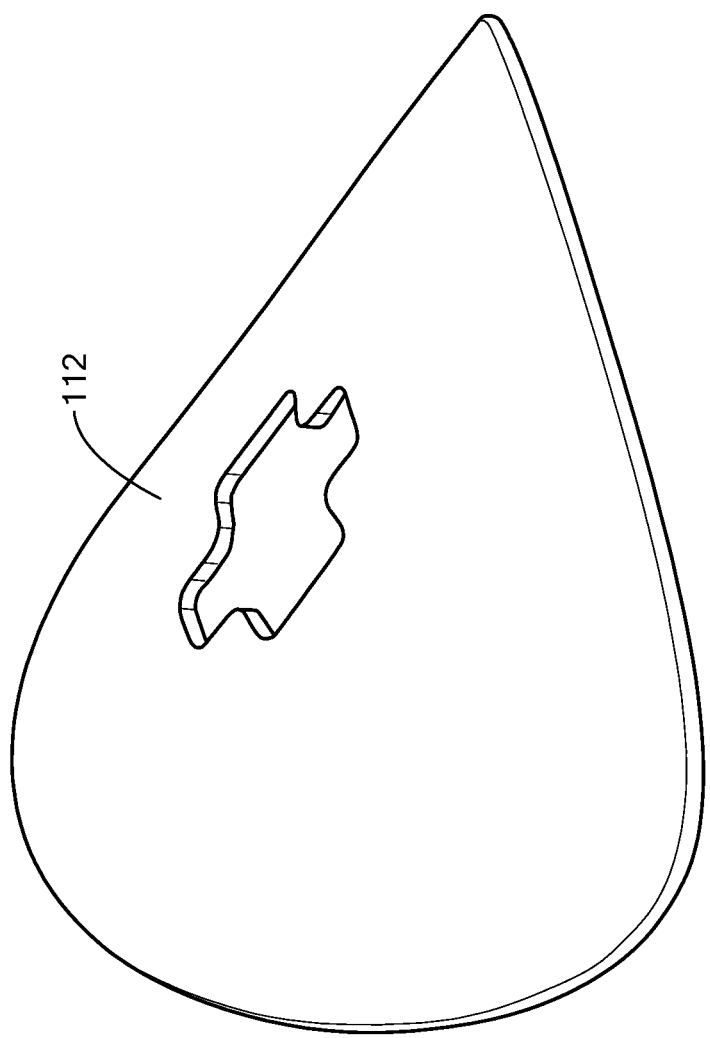
FIG. 12 is an isometric view of a flexible wing component of the intra-arterial foot shown in FIGS. 9 and 10.

FIGS. 11 and 12 illustrate each of the two components of intra-arterial foot 102, with FIG. 11 illustrating central core component 110 and FIG. 12 illustrating flexible wings 112.

Flexible wing 112 increases the surface area of the intra-arterial foot contacting the inner surface of an artery and hence, increases the tamponade effect of intra-arterial foot 102. As such, bleeding from arteriotomy 202 is increasingly controlled during the delivery and securing of the closure device 100. Central core component 110 provides intra-arterial foot 102 with additional structural integrity. Additionally, central core 110 facilitates the delivery of sutures 104 and maintains the engagement of the sutures after tensioning of the sutures. In particular, as shown by FIG. 9 and particularly FIG. 11, central core component 110 includes a plurality of openings or slots for receiving sutures 104. More particularly, needles 108 are ejected from their driving member and pass through channel 111. Providing flexible wing 112 separate and independent from the central core component 110 further facilitates the longitudinal flexibility of flexible wing 112.

Figure 16:
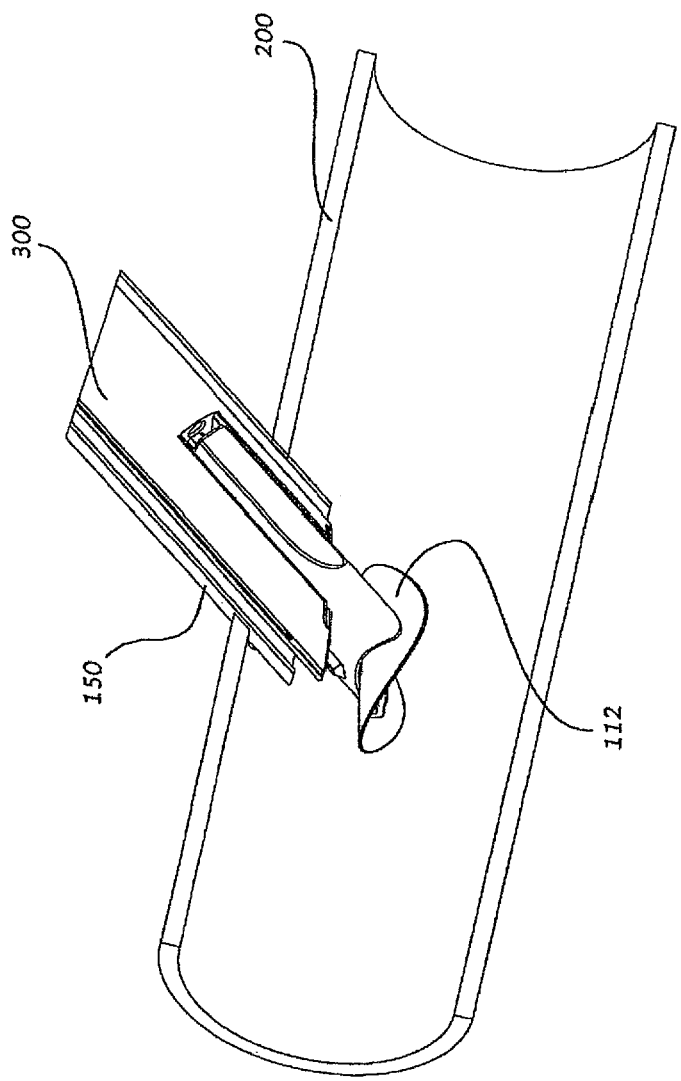
FIG. 16 is an isometric side view of the intra-arterial foot of FIGS. 9-14 illustrating the flexible wing component deployed when the intra-arterial foot is advanced through the delivery sheath into the artery.

With reference to FIGS. 13-16, a method of delivering the intra-arterial foot 102 of FIGS. 9-10 is described. During delivery of the two-piece intra-arterial foot 102, flexible wing 112 is folded to fit within a procedural or delivery sheath 150. Upon exiting delivery sheath 150, flexible wing 112 intrinsically spreads open during deployment. FIGS. 15 and 16 illustrate isometrically the flexible wing folded within delivery sheath 150 and opened once the intra-arterial foot 102 is advanced through the delivery sheath 150 into artery 200. After exiting the delivery sheath, at least a portion of the delivery device, automatically or under direct control of the operator, is partially retracted thereby positioning wing 112 of foot 102 on the inner lumen surface directly below the arteriotomy site. In embodiments including a wound spreader, this retraction may place the wound spreader within the arteriotomy, thereby shaping the wound as discussed further below and assisting with the occlusion of the wound to provide a hemostatic effect. In concert with the wound spreader shaping and occluding the arteriotomy the deployed flexible wing 112 creates a tamponade on the arteriotomy 202, immediately controlling arterial bleeding. As such, flexible wing 112 takes advantage of hydraulic forces within artery 200 to create a seal as the foot in its entirety is secured in place. It is noted that the intrinsic opening of wings 112 is by way of the elastic properties of the wing materials.

In other embodiments, flexible wing 112 may be actively spread, once deployed from the delivery sheath 150, by applying tension to sutures that are attached to the lateral extremities of wing 112. In this particular embodiment (not shown by the figures), the lateral sutures would also retract the lateral wound edges 203a, 203b of arteriotomy 202 during applied tension to the structures. Controlling the positioning of the wound edges 203a, 203b in this manner is significant in (1) aiding the tamponade of the winged intra-arterial foot, (2) facilitating the ability to accurately deploy the needle 108 and suture system 104 relative to the controlled position of the wound edges, and (3) centralizing the device relative to the arteriotomy 202. Mechanically, positioning the wound edges once the delivery sheath 150 has been removed from the arteriotomy has particular relevance to large arteriotomies (e.g. above 10 French units), which loose their intrinsic ability to contract the wound edges.

Figure 63:
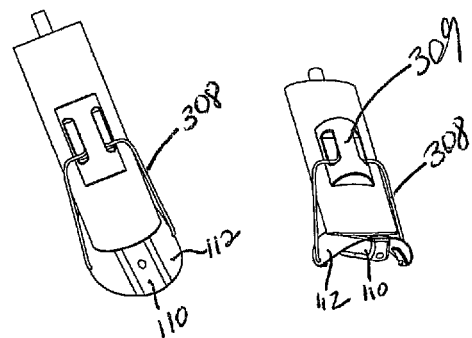
FIG. 63 illustrates two isometric views of the distal end of a delivery device having first and second clips attached to the flexible wing of the intra-arterial foot of FIGS. 9 and 10.

With reference to FIG. 63, an alternative to actively spreading flexible wing 112 and retracting wound edges 203a and 203b is illustrated. In this particular embodiment, the stored energy in a spring clips 308 is used to spread wing 112. Spring clips 308 may be, for example, a stainless steel wire or a nitinol clip. In some embodiments, each spring clip 308 is flexible enough to allow flexible wing 112 to fold within delivery sheath 150, actively spread the wing and simultaneously retract the lateral edges of arteriotomy 202. Each clip 308 is attached to either side of flexible wing 112, as illustrated by the figure. Clips 308 may be released from flexible wing 112, after intra-arterial foot 102 is implanted about arteriotomy 202, by pulling clips 308 in an upward direction relative to the plane of the intra-arterial foot 102, and using arterial wall 204 to provide counter traction to allow clip 308 to release from flexible wing 112 wing spreader recess. Clip housing 309 houses the proximal end of each clip 308, leading and aiding the control the movement of the clips 308 during the pulling action. In some embodiments, clips 308 are adapted for spreading the wound edges of the arteriotomy.

With reference to the embodiment shown in FIG. 12, the geometry of wing 112 is elliptical in shape, i.e. wider in the latitudinal or transverse to the longitudinal axis of the artery. In some embodiments, the minor diameter of the ellipse is larger than the diameter of the arteriotomy by at least $(\pi) \times (diameter)/2$. This particular dimensioning of wing 112 is necessary to form an effective seal. Typically, arteriotomy 202 is formed by progressive dilation. In addition, and as a consequence of the morphology of arterial wall 204, the arteriotomy is generally of a transverse nature, and hence the width of the arteriotomy (in its natural state) is given by $(\pi) \times (diameter)/2$, where "diameter" is the outer diameter of the dilator (not shown by the figures) used to create the arteriotomy. An elliptically shaped wing oriented with its major diameter transverse to the longitudinal axis of the artery offers an advantageous seal over a circular profile with respect to the transverse nature of the arteriotomy since the material needed to create the seal is reduced. That is, although a circular wing could create a seal, a larger surface area would be required.

As shown in FIG. 12, wing 112 may be curved in profile to match the profile of the lumen of artery 200. Alternatively, wing 112 may be flat (FIGS. 31-39) to increase its shape memory (i.e. spring-back).

Figure 18:
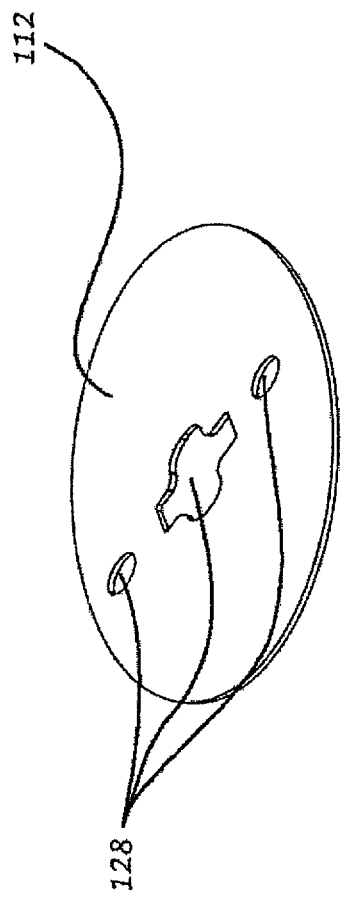
FIG. 18 is an isometric view of a profiled flexible wing component having a plurality of openings for facilitating alignment of the central core component of FIG. 11, in accordance with other embodiments of the present invention.
Figure 17:
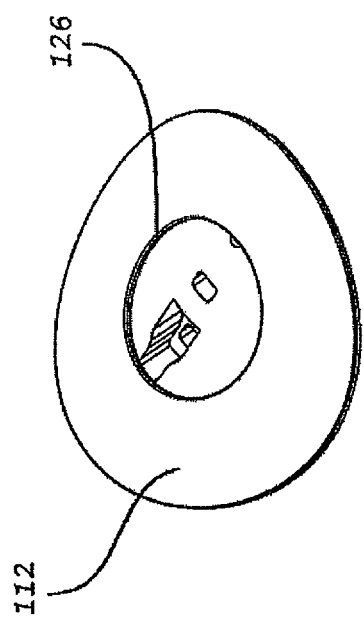
FIG. 17 is an isometric view of the flexible wing component illustrating a central opening, in accordance with various embodiments of the present invention.
Figure 19:
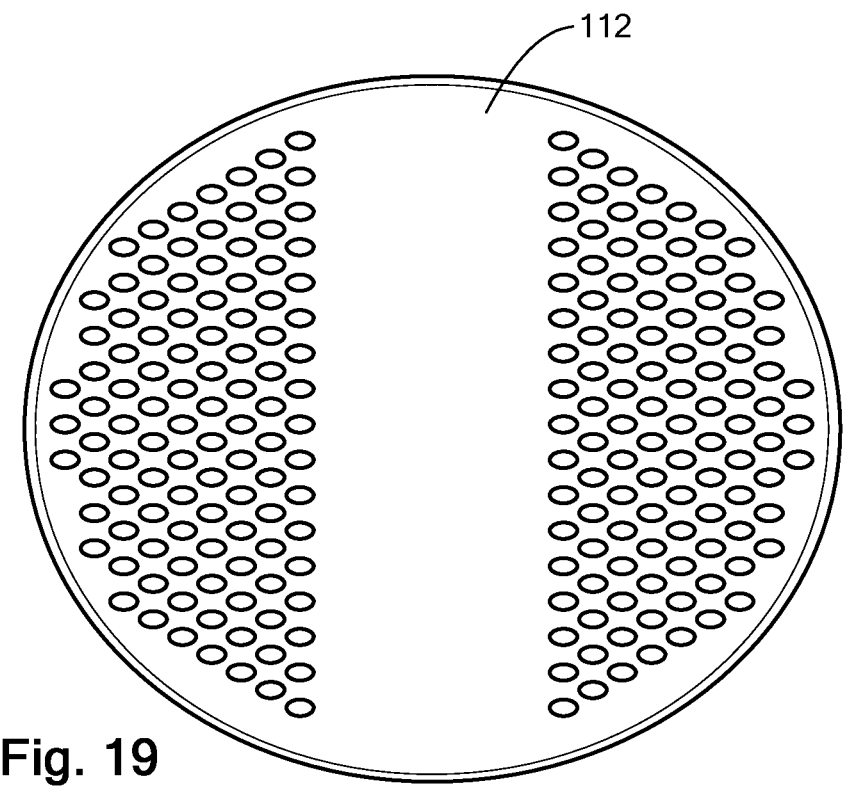
FIG. 19 illustrates a plan view of one embodiment of the flexible wing component of FIG. 12, having patterned holes and a non-porous mid-section.
Figure 20:
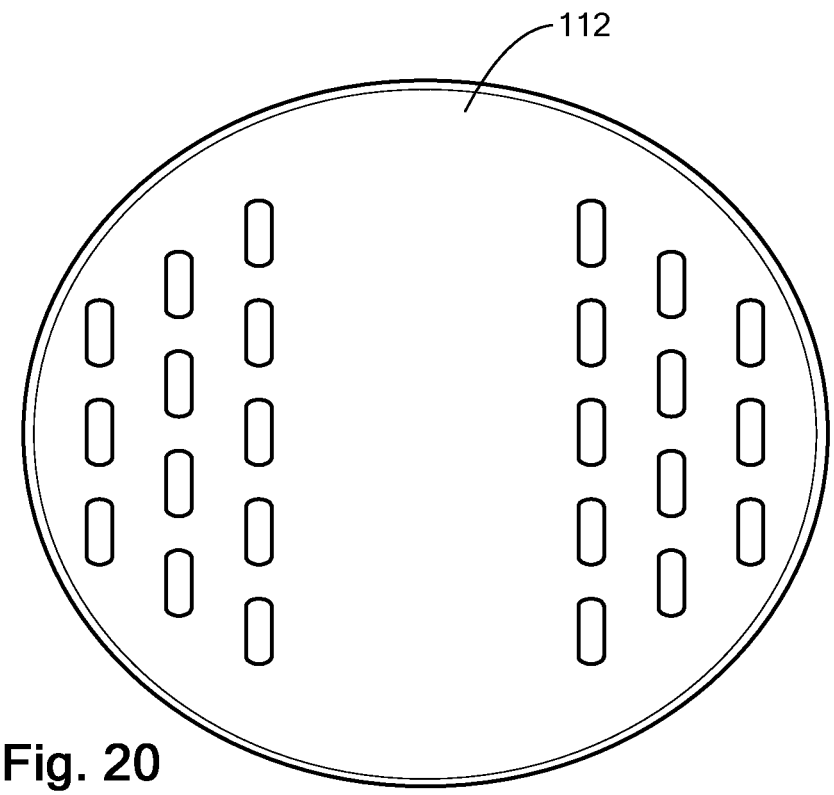
FIG. 20 illustrates a plan view of another embodiment of the flexible wing component of FIG. 12, having patterned slots and a non-porous mid-section.
Figure 21:
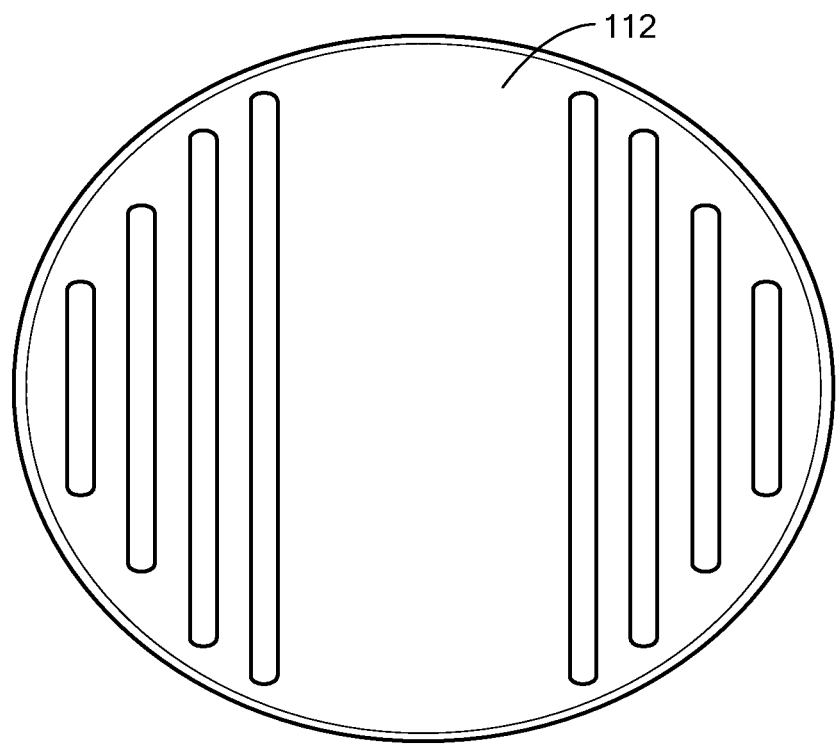
FIG. 21 illustrates a plan view of another embodiment of the flexible wing component of FIG. 12, having parallel slots and a non-porous mid-section.
Figure 22:
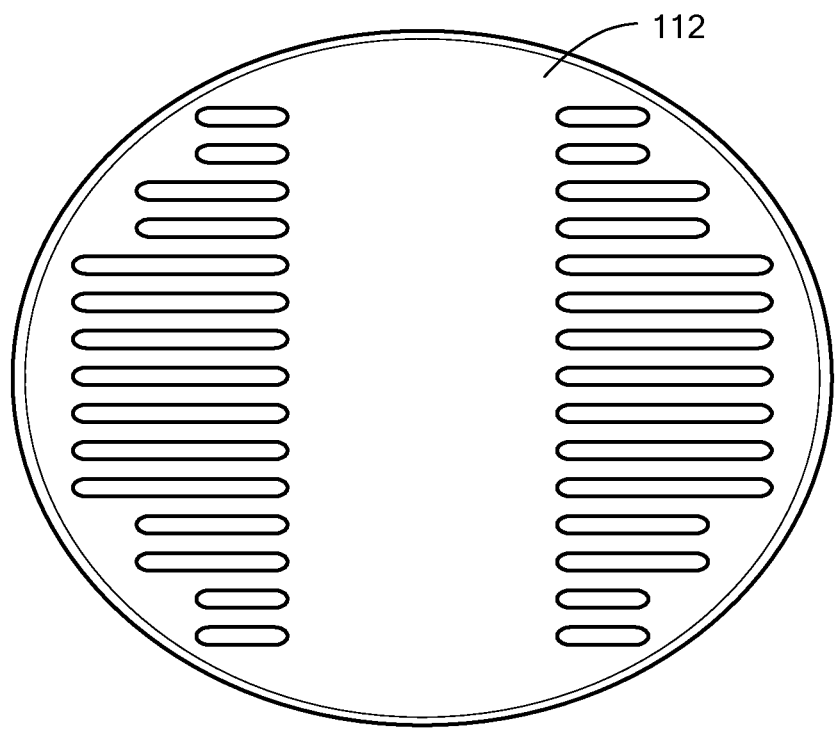
FIG. 22 illustrates a plan view of yet another embodiment of the flexible wing component of FIG. 12, having parallel slots and non-porous mid-section.
Figure 23:
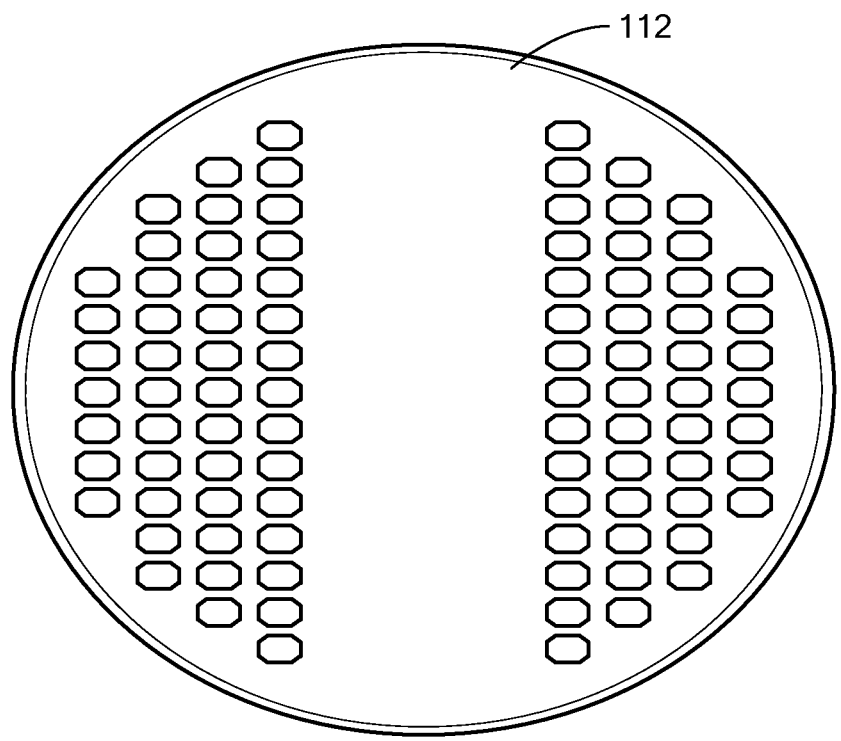
FIG. 23 illustrates a plan view of yet another embodiment of the flexible wing component of FIG. 12, having profiled patterned holes and non-porous mid-section.
Figure 24:
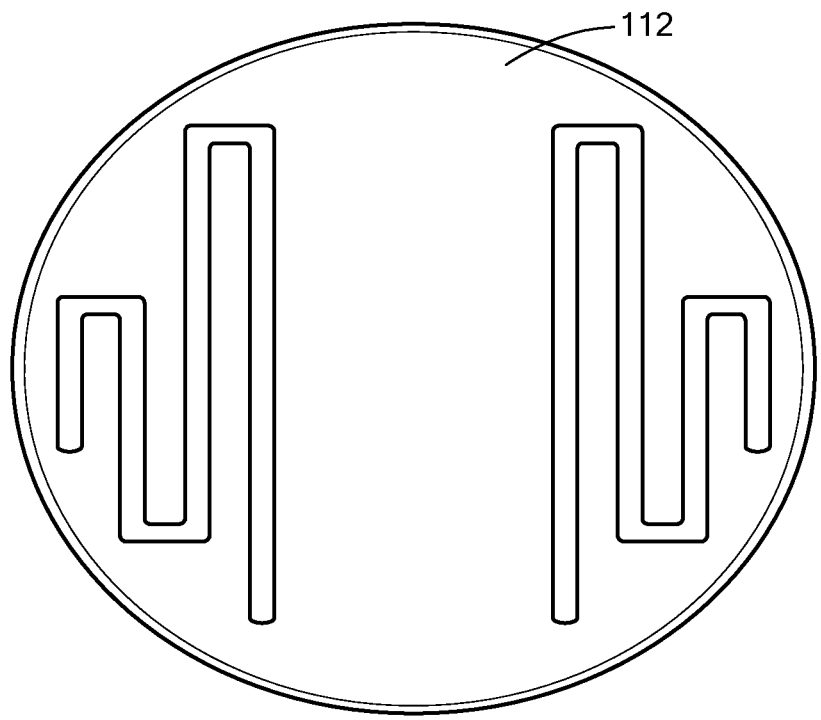
FIG. 24 illustrates a plan view of yet another embodiment of the flexible wing component of FIG. 12, having profiled slots and non-porous mid-section.

Wing 112 may include a central opening 126 (FIG. 17), which may be circular to allow the wing to freely rotate independent of the foot core. Alternatively, wing 112 may include a plurality of openings 128 (FIG. 18) that correspond to a plurality of openings in central core 110 (not shown) in a specific alignment.

The flexibility of wing 112 is not just important in a lateral configuration to facilitate collapse during delivery (FIGS. 13-16), but it is also important to have flexibility in a longitudinal plane. Flexibility in both lateral and longitudinal planes is important for some embodiments to ensure an effective tamponade of arteries in differing disease states with different surface topographies and varying anatomical configurations. Independent flexibility in different planes may be achieved with elastomeric materials such as polydioxanone, polyurethane films, or by very thin films produced by extrusion, solvent casting, or compression molding, etc. Wing geometry, perforations, slots, etc. can also be utilized to infer independent flexibility in different directions. It is also advantageous that the wing be porous in some embodiments to allow nutrient exchange to the luminal surface 206 of artery 200, whilst maintaining sufficient tamponade effect. This facilitates blood coagulation on the wing surface and creates a seal.

Figure 25:
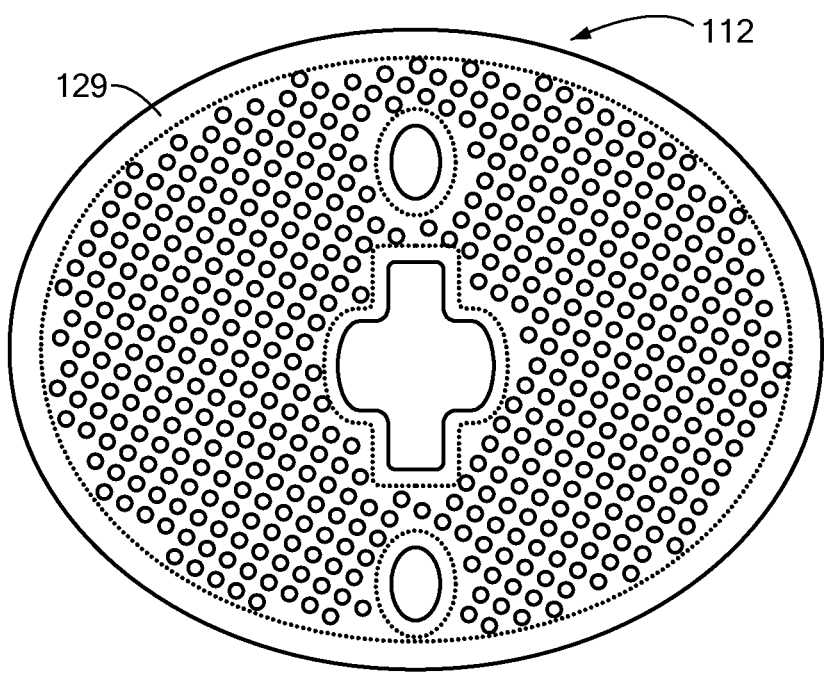
FIG. 25 illustrates a plan view of yet another embodiment of the flexible wing component of FIG. 12, having patterned holes and non-porous border around the edges.
Figure 26:
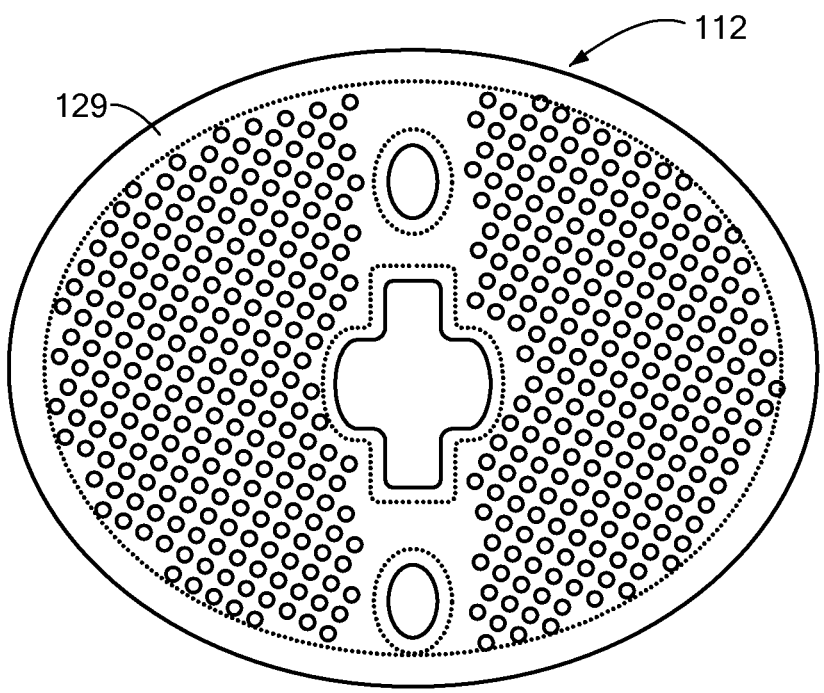
FIG. 26 illustrates a plan view of another embodiment of the flexible wing component of FIG. 12, having patterned holes and solid non-porous mid-section.

FIGS. 19-26 illustrate various embodiments of different types of wing designs to increase the flexibility and the porosity of wing 112, in accordance with various embodiments of the present invention. With particular reference to FIGS. 25 and 26, the solid broader silhouette 129 is designed to stiffen the wing's perimeter to prevent the potential of the wing to folding-back-on-itself during deployment within the artery 200 and during the natural blood flow of the artery. It is noted that porosity of the wing may also be achieved by use of absorbable porous materials, such as, for example, electrospun Polyglycolic acid (PGA) or the addition of soluble materials to the polymer during processing.

Figure 27:
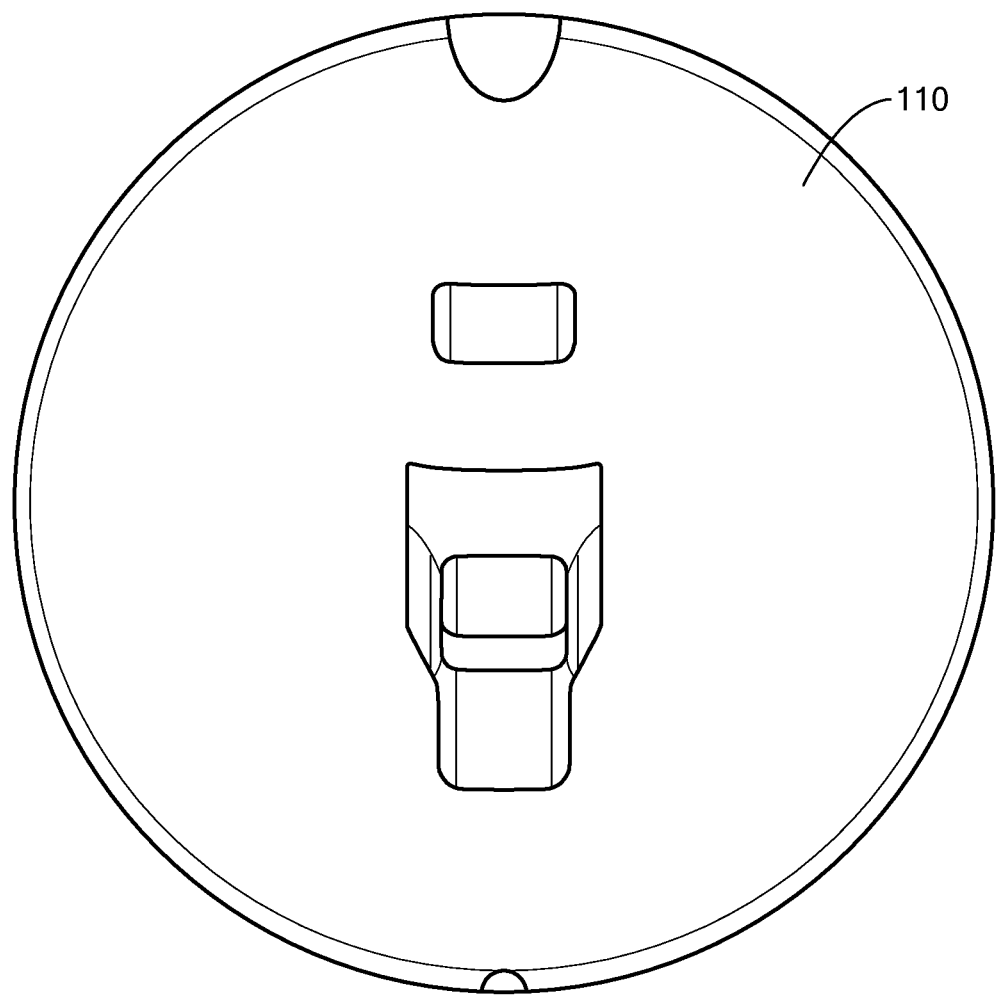
FIG. 27 is a plan view of an embodiment of the central core component of FIG. 11.
Figure 28:
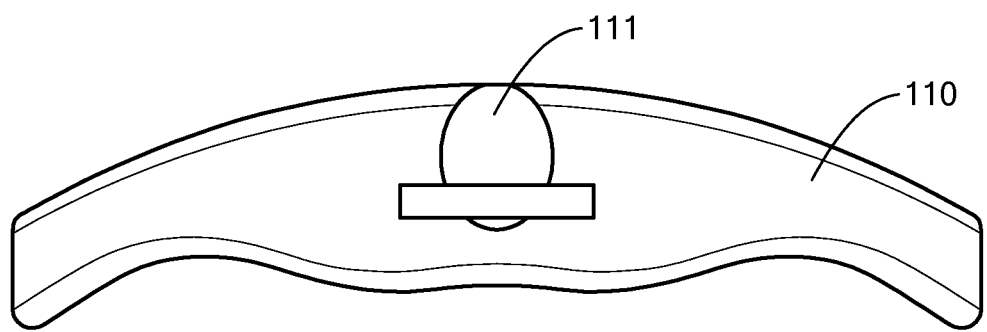
FIG. 28 is an end view of the central core component of FIGS. 11 and 27.
Figure 29:
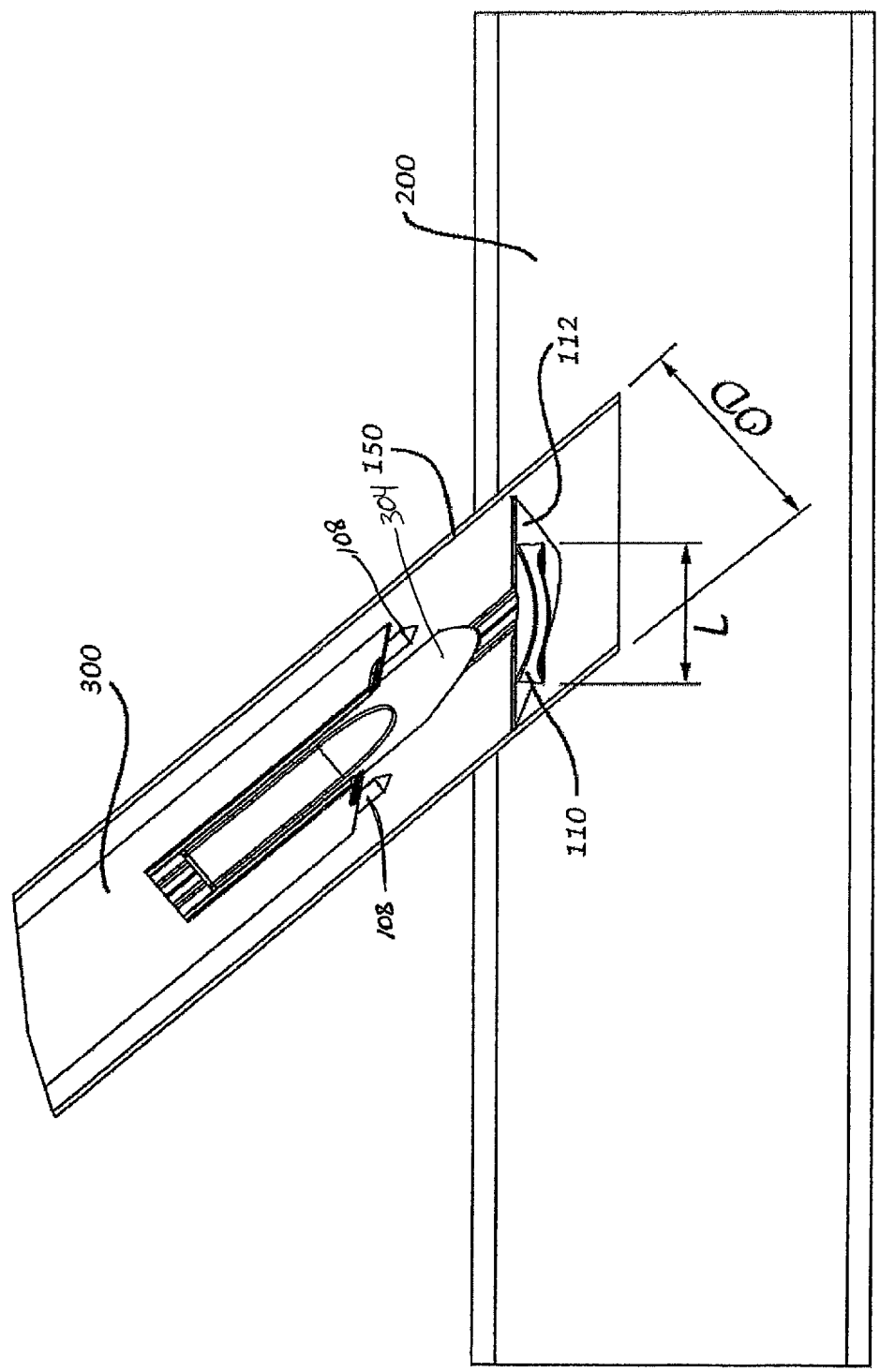
FIG. 29 is an elevated cross-sectional view of the intra-arterial foot, illustrating the dimensions of the intra-arterial foot relative to an arteriotomy, in accordance with embodiments of the present invention.
Figure 31:
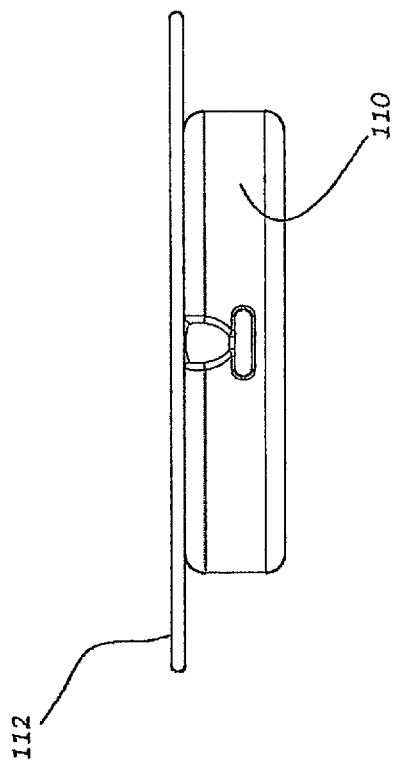
FIG. 31 is an end view of the intra-arterial foot of FIG. 30.
Figure 30:
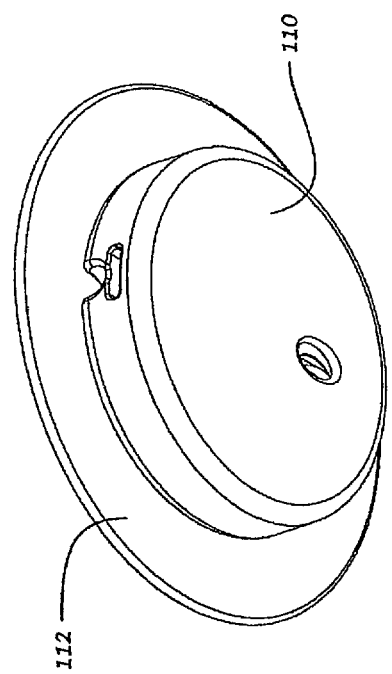
FIG. 30 is an isometric view of another embodiment of an intra-arterial foot illustrating the central core portion with a uniform thickness.
Figure 32:
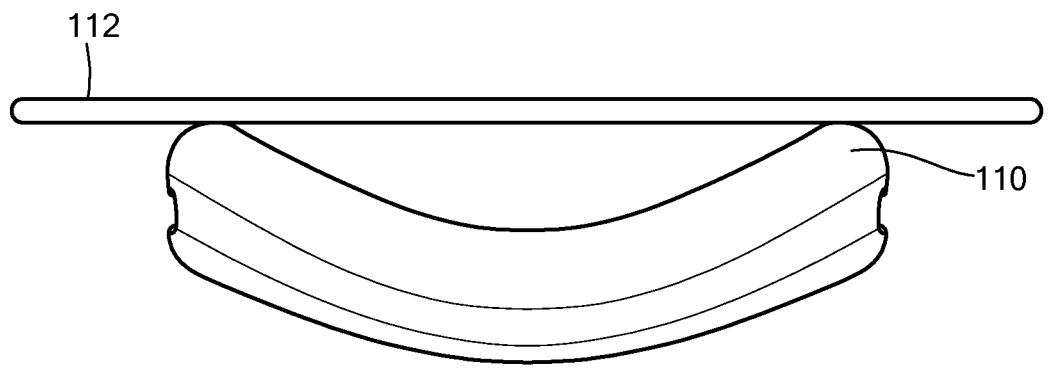
FIG. 32 is a side view of another embodiment of an intra-arterial foot illustrating the central core portion having a circular profile with uniform thickness.
Figure 33:
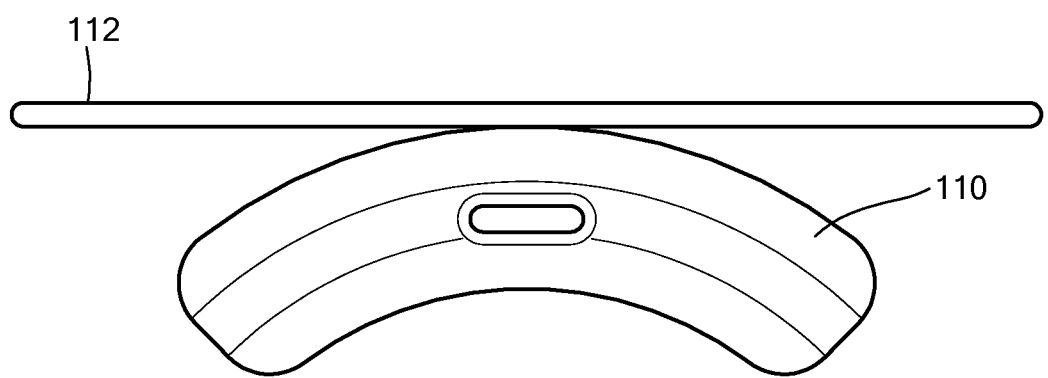
FIG. 33 is an end view of the intra-arterial foot of FIG. 32.
Figure 34:
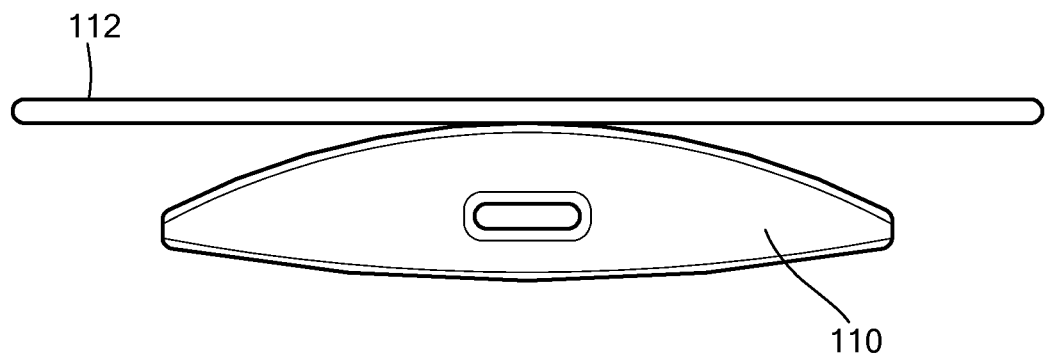
FIG. 34 is an end view of yet another embodiment of an intra-arterial foot illustrating the central core portion having a circular profile with varying thickness.
Figure 35:
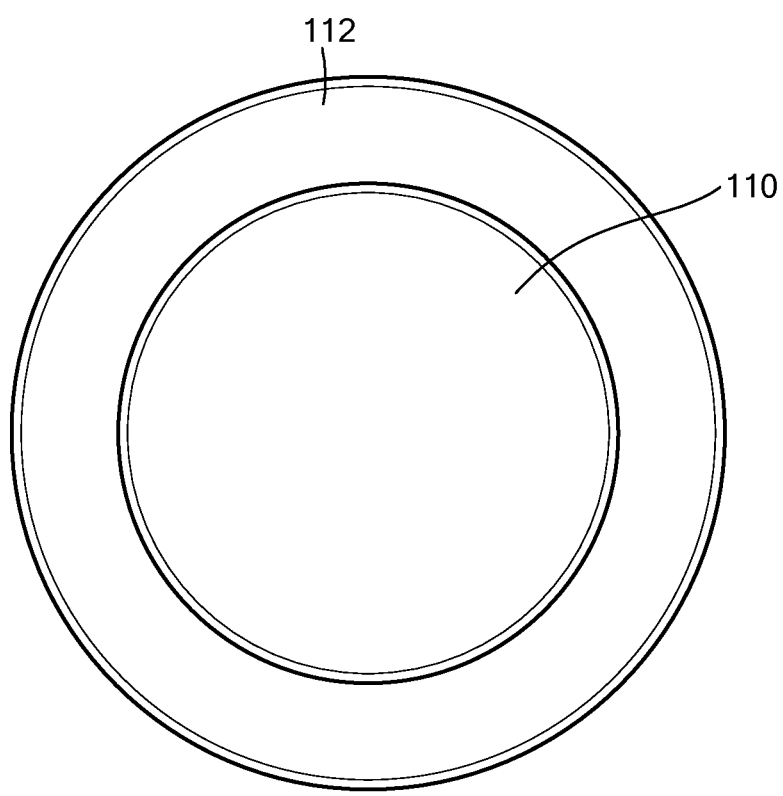
FIG. 35 is a bottom view of the intra-arterial foot of FIG. 34.
Figure 37:
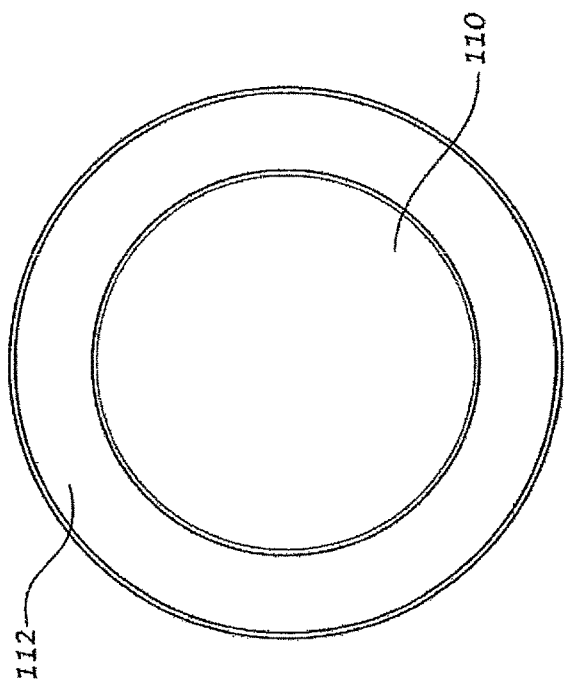
FIG. 37 is a bottom view of the intra-arterial foot of FIG. 36.
Figure 36:
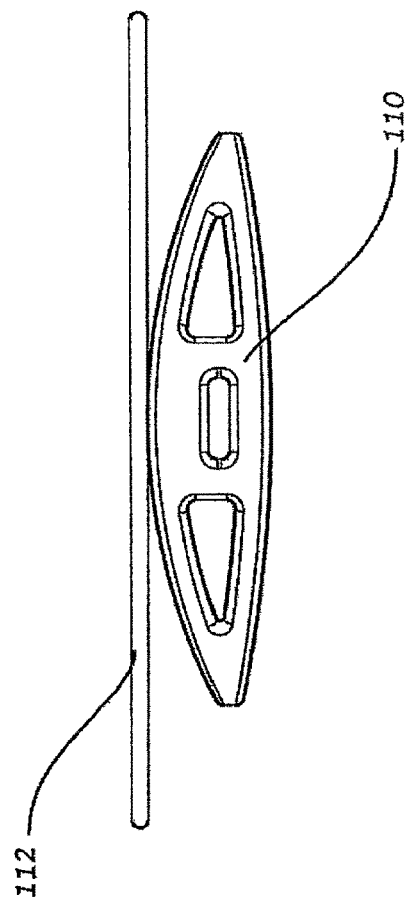
FIG. 36 is an end view of yet another embodiment of an intra-arterial foot illustrating the central core portion having a circular profile with varying thickness and hollowed sections.
Figure 39:
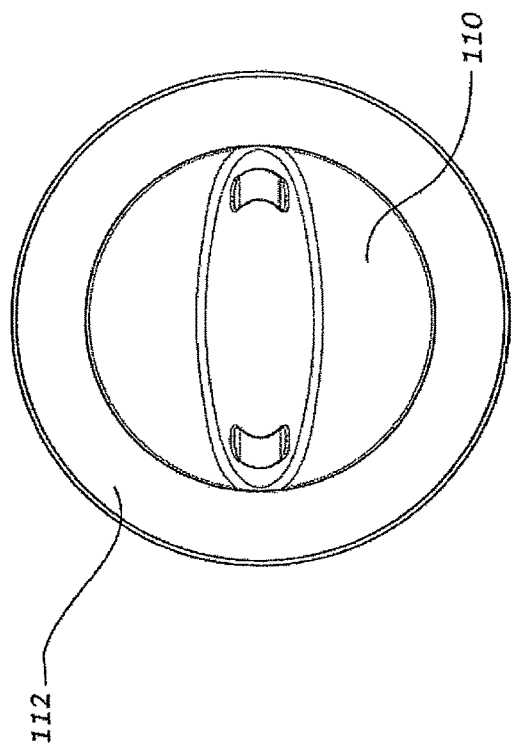
FIG. 39 is a bottom view of the intra-arterial foot of FIG. 38.
Figure 38:
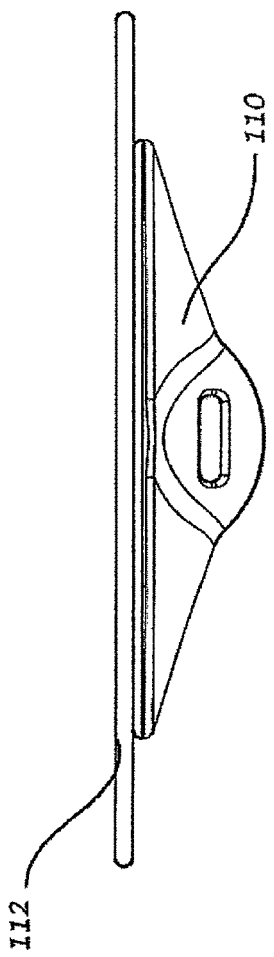
FIG. 38 is an end view of yet another embodiment of an intra-arterial foot illustrating the central core portion having a circular profile and varying thickness.
Figure 41:
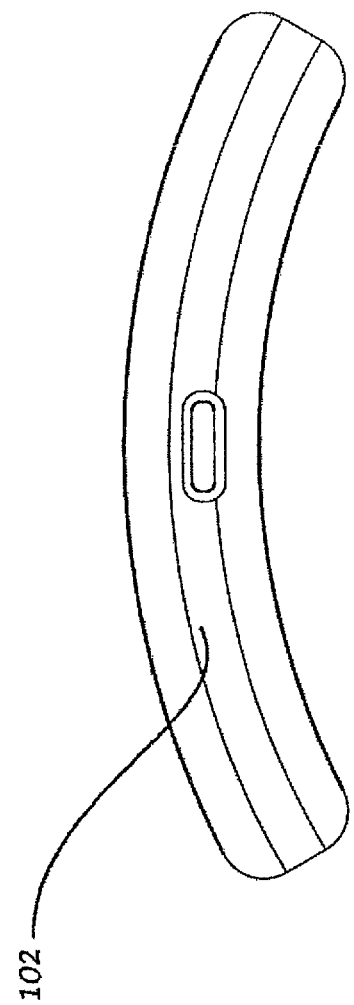
FIG. 41 is an end view of the intra-arterial foot of FIG. 40.
Figure 40:
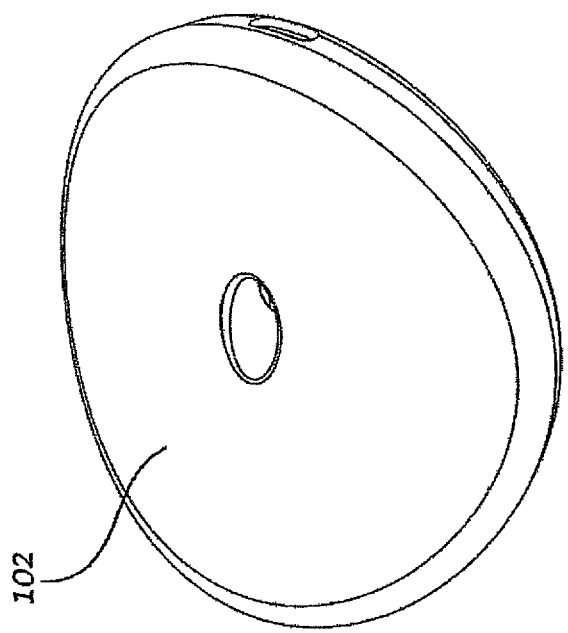
FIG. 40 illustrates an isometric view of another embodiment of the intra-arterial foot, in accordance with embodiments of the present invention.
Figure 43:
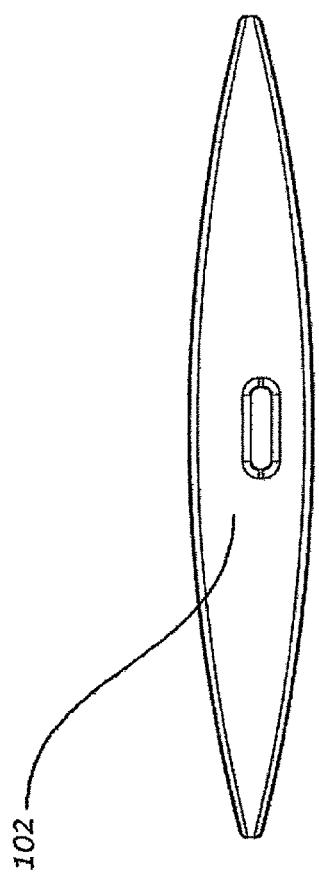
FIG. 43 is an end view of the intra-arterial foot of FIG. 42.
Figure 42:
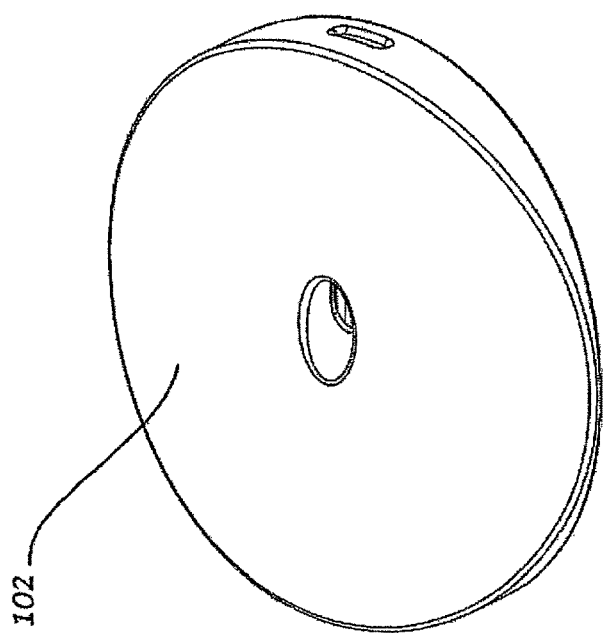
FIG. 42 illustrates an isometric view of another embodiment of the intra-arterial foot, in accordance with embodiments of the present invention.
Figure 47:
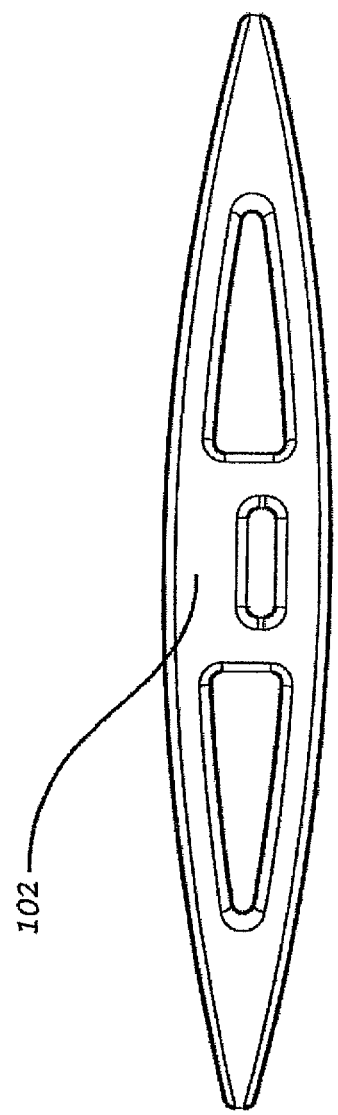
FIG. 47 is an end view of the intra-arterial foot of FIG. 46.
Figure 46:
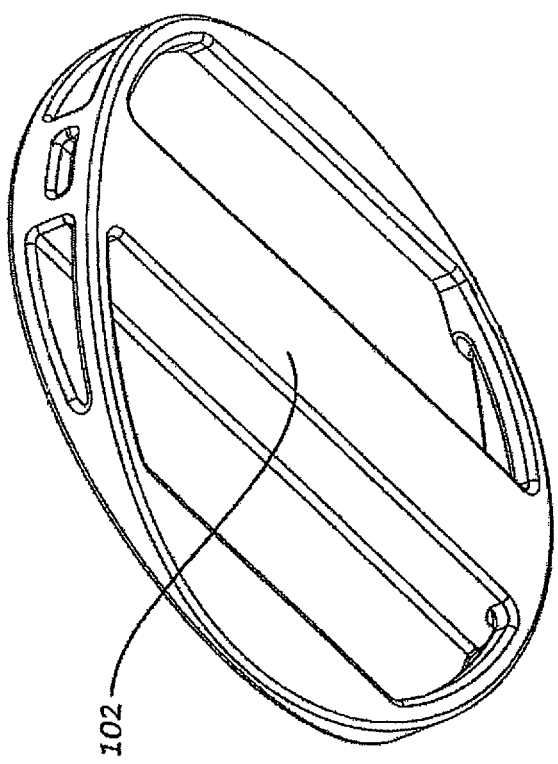
FIG. 46 is illustrates an isometric view of yet another embodiment of the intra-arterial foot, in accordance with embodiments of the present invention.
Figure 49:
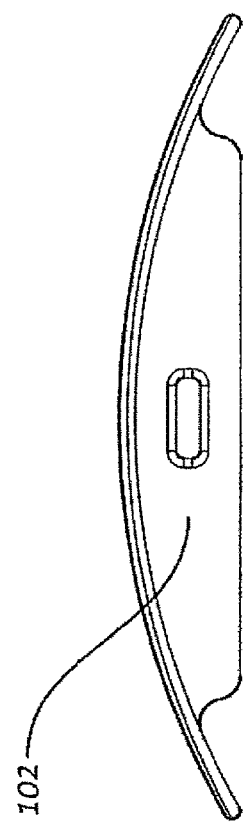
FIG. 49 is an end view of the intra-arterial foot of FIG. 48.
Figure 48:
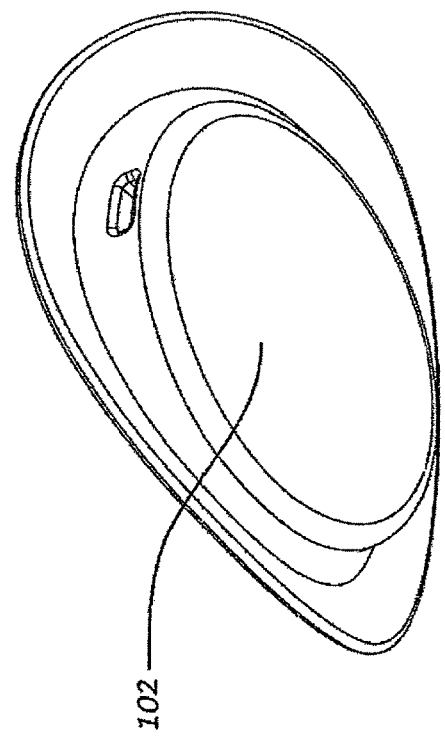
FIG. 48 illustrates an isometric view of another embodiment of the intra-arterial foot, in accordance with embodiments of the present invention.

With reference to FIGS. 27-29, in conjunction with FIGS. 9 and 10, central core component 110 may be circular in geometry and of a higher stiffness, relative to wing 112. In some embodiments, central core component 110 is sized to be less than the diameter of the arteriotomy 202 (FIG. 29). This ensures that central core component 110 fits comfortably within the delivery sheath 150. As illustrated by FIG. 29, central core component 110 may include a curvature for suiting the luminal curvature of the artery (see, for example, FIG. 7). This curvature imparts an elliptical surface area on central core component 110, similar to wing 112, with a major diameter transverse to the longitudinal axis of artery 200. The shape of central core component 110 (equivalent to that of wing 112) helps to ensure wing 112 unfolds when deployed from within the delivery sheath 150. Additionally, the shape of central core component 110 supports flexible wing 112 once positioned against the arterial lumen 206 and helps to prevent wing 112 from folding back on itself during deployment.

With continued reference to FIG. 29, central core component 110 includes a diameter "L" that is smaller than the arteriotomy 202 and the outside diameter "OD" of delivery sheath 150. Moreover, flexible wing 112 includes a diameter larger than the arteriotomy 202 and the outside diameter of delivery sheath 150. In such embodiments, and as described herein, flexible wing 112 is deployable from a folded first position to a deployed second position.

FIGS. 30-39 illustrate alternative embodiments of central core component 110 and flexible wing 112. These embodiments illustrate central core component 110 and wing 112 as circular in the plan view. Central core component 110 and wing 112 may include the same material. Moreover, wing 112 is independent from central core component 110, where wing 112 is larger than the diameter of arteriotomy 202 and central core component 110 is smaller than the diameter of arteriotomy 200.

With reference to FIGS. 40-49, alternative embodiments of intra-arterial foot 102 are illustrated. In these embodiments, intra-arterial foot 102 is a single piece configuration (i.e. central core component 110 and wing 112 are one unit) manufactured from one material. These embodiments illustrate designs that are circular in the plan view. The outer diameter of the intra-arterial foot 102 of FIGS. 40-49 is larger than the diameter of arteriotomy 202. This design concept requires that the intra-arterial foot material be elastomeric so that, the one piece intra-arterial foot can be deformed during insertion into the delivery sheath and will open out to its original diameter without any plastic deformation, once deployed within the artery. By way of example, for an 18 French arteriotomy, these designs would typically have an intra-arterial foot diameter of 10 mm in the plan view.

In accordance with embodiments of the present invention, closure device 100 is bio-absorbable. In particular, closure device 100 has a functional requirement with structural integrity in the order of approximately 1 to 100 days to allow clinical healing of the arterial wall and absorption should be complete within approximately 1 to 300 days. As known in the art, complete absorption is defined as less than approximately 10% of the original mass.

In some embodiments, material for the intra-arterial foot is the same for both the flexible wing and the central core to ensure consistent, more predictable biocompatibility and ease of manufacturing. These materials are required to be both haemocompatible and biocompatible in some embodiments. The materials may be non-absorbable, however, the preferred material would be synthetic absorbable polymer. Selection of the appropriate absorbable material is based on haemocompatibility, biocompatibility functional and physical characteristics and absorption profile.

The haemo- and biocompatibility requirements of the material, in accordance with embodiments of the present invention, include, but are not limited to materials that do not cause adverse tissue reaction, haemolysis, and severe thrombogenesis or occluding emboli formation. During absorption of the material, the breakdown products from the absorbable material should not result in producing emboli, which would cause downstream occlusion. This is achieved by surface erosion which produces particles of less than 8 µm (to allow them to pass through a capillary bed), or by encouraging encapsulation of the intra-arterial implant to anchor all fragmented particles from the absorbing implant to the arterial wall 204.

Moreover, the functional and physical characteristics of the material should allow elastic deformation of the flexible wing (to allow it to fold within the delivery sheath 150 and conform to the luminal surface of the artery once delivered), and provide sufficient strength, stiffness or rigidity to the central-core to allow correct positioning, suture capture and locking during the delivery process.

In one particular embodiment, the absorption profile should allow structural integrity of the implant for at least 20 days to allow clinical healing of the arterial wall 204 and absorption should be complete within approximately 90 days, in which time the arterial wall will have completely remodeled to its original condition. Complete absorption is defined as less than 10% of the original mass. Intra-arterial foot 102 may be manufactured with bio-degradable plastic and elastomeric materials such as, for example, PGA, PGLA, PUR and PDO.

In one particular embodiment, the intra-arterial foot 102 is radiopaque such as to locate intra-arterial foot 102 in situ, after implantation by means of a radiograph or fluoroscopy or other x-ray imaging modality. Radiopacity of the intra-arterial foot can be achieved by the addition of contrast agents to the polymer such as, for example, barium sulphate. An alternative method is to incorporate the addition of an absorbable radiopaque metal alloy such as, for example, bioabsorbable magnesium alloy.

In accordance with embodiments of the present invention, intra-arterial foot provides numerous advantages over the prior art. For example, flexible wing 112 allows the sealing component of intra-arterial foot 102 to fold for delivery. In addition, flexible wing 112 allows large surface area sealing member (greater than the diameter of the arteriotomy) to be delivered into the artery for effective tamponade of the arteriotomy. Moreover, the flexible and independent wing 112 allows the sealing member to conform to the topology of the arterial luminal surface. Furthermore, flexible wing 112 may be made from porous material to aide nutrient exchange to the luminal surface beneath the wing. Because flexible wing 112 is wider in the latitudinal plane, it reduces the surface of the sealing member without compromising the effectiveness of the seal. Moreover, an active wound refraction (on the lateral edges) controls the wound edges position for better control of bleeding, ensuring the intra-arterial foot 102 is centrally aligned relative to the arteriotomy, and increases the distance from the wound edge to the suture penetration point.

The central core component 110 facilitates both delivery and securing of the closure device. In addition, the central core component 110 in circular plan-view profile aids in supporting the flexible wing within the artery, to ensure the wings 112 unfold and help to prevent fold-back of the wings. Moreover, intra-arterial foot 102 can be made from absorbable material, leaving no permanent implant once healing is complete.

With reference to FIGS. 50-56, needle tip 108 includes a body portion 130 having a proximal spherical end 132. In accordance with some embodiments of the present invention, needle tip 108 and suture 104 form a "T" configuration (See, for example, FIG. 75). In particular, the proximal spherical end 132 facilitates rotation of the needle tip 108 to and from the "T" configuration with suture 104 upon ejection from its driver (not shown). Body portion 130 includes an opening 134 for receiving a portion of suture 104 therein. In one particular embodiment, opening 134 is conical with a first diameter substantially smaller than a second diameter, where the first diameter is adjacent to the suture side so as to increase security of the attached suture 104. As discussed herein, suture 104 may be secured to body portion 130 by conventional means including adhesives, bonding, etc.

Figure 50:
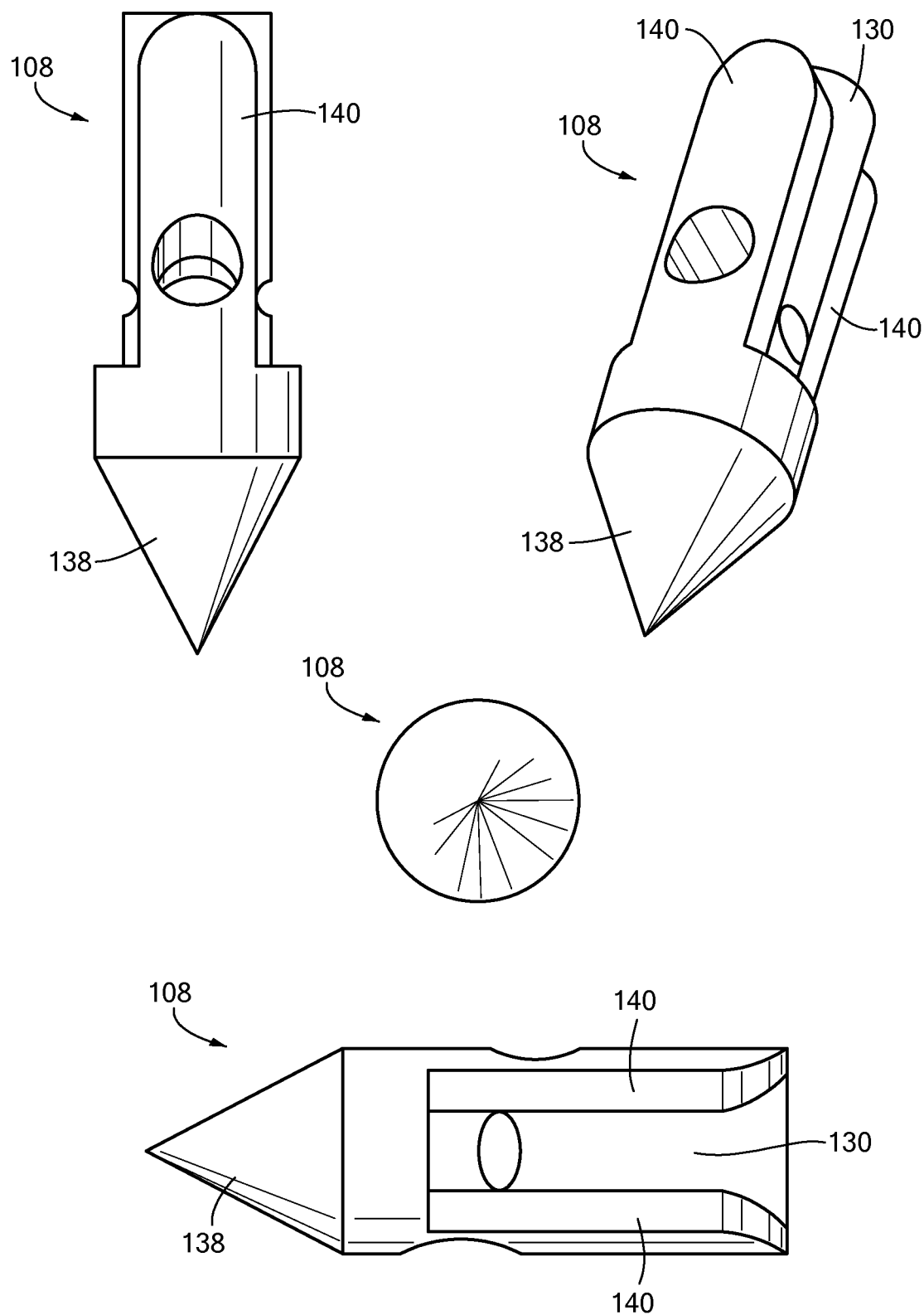
FIG. 50 illustrates top, front, side and isometric views of a needle, in accordance with embodiments of the present invention.
Figure 51:
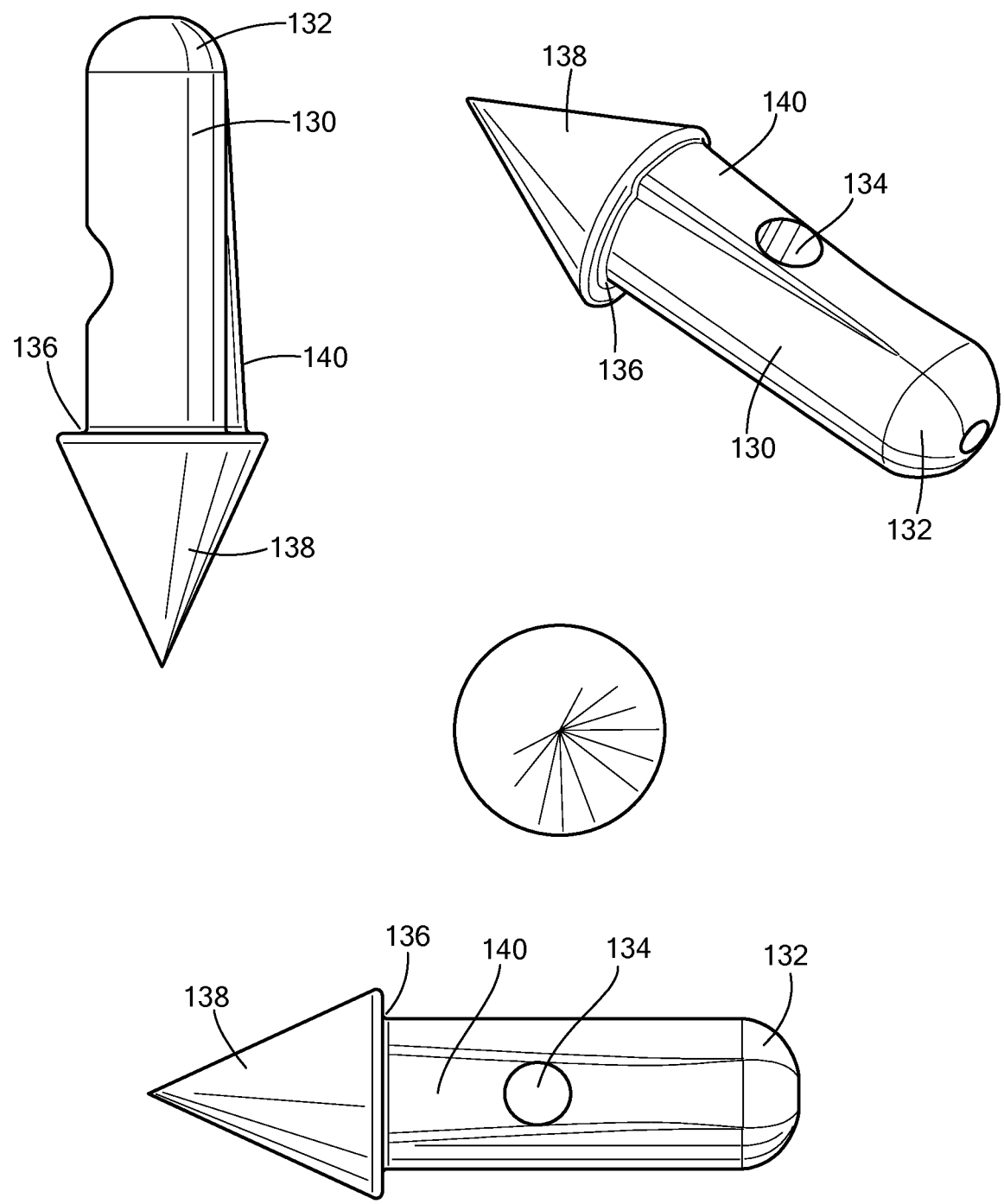
FIG. 51 illustrates side, front, top and isometric views of a needle, in accordance with embodiments of the present invention.
Figure 52:
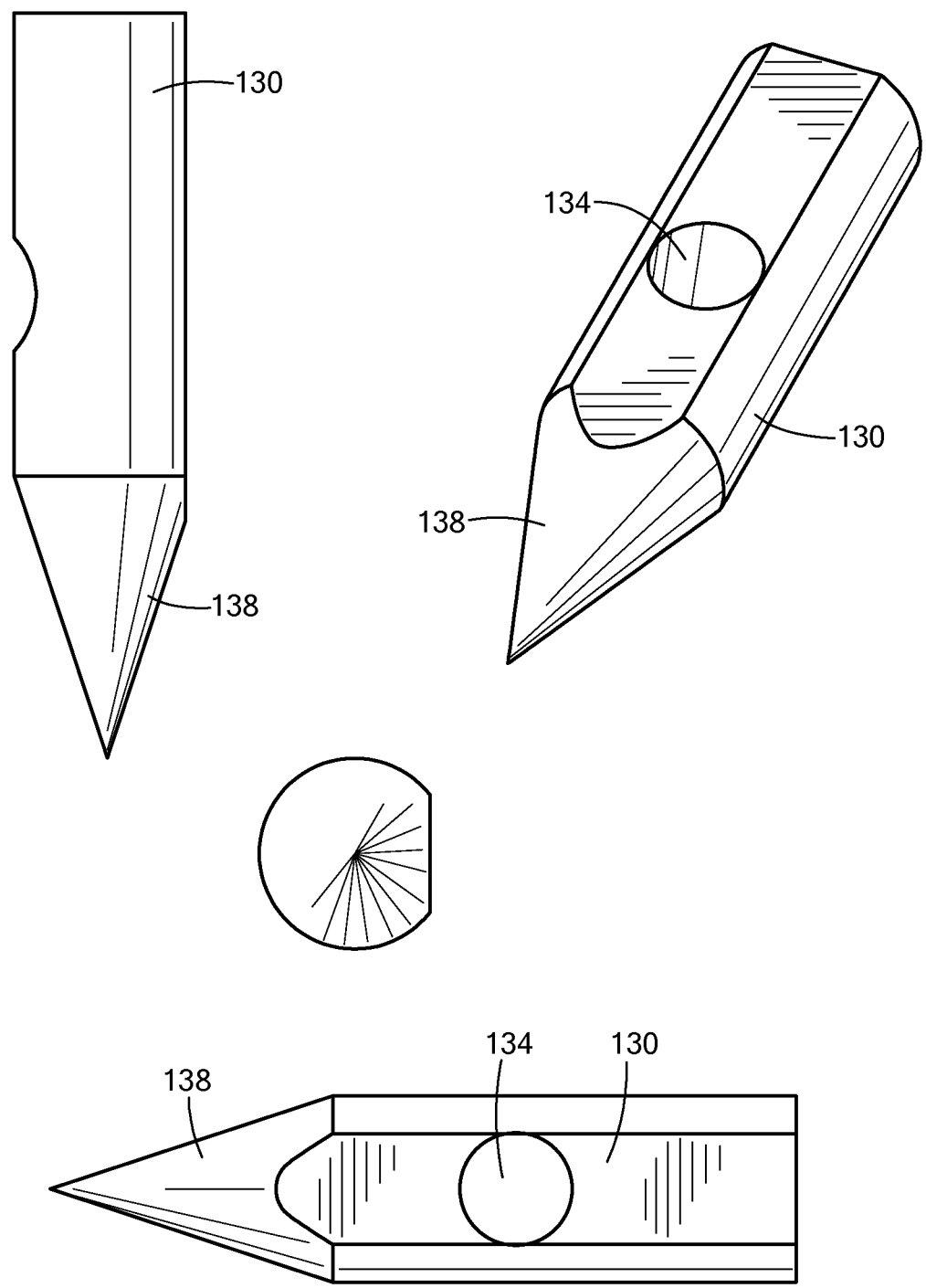
FIG. 52 illustrates side, front, top and isometric views of a needle, in accordance with embodiments of the present invention.
Figure 53:
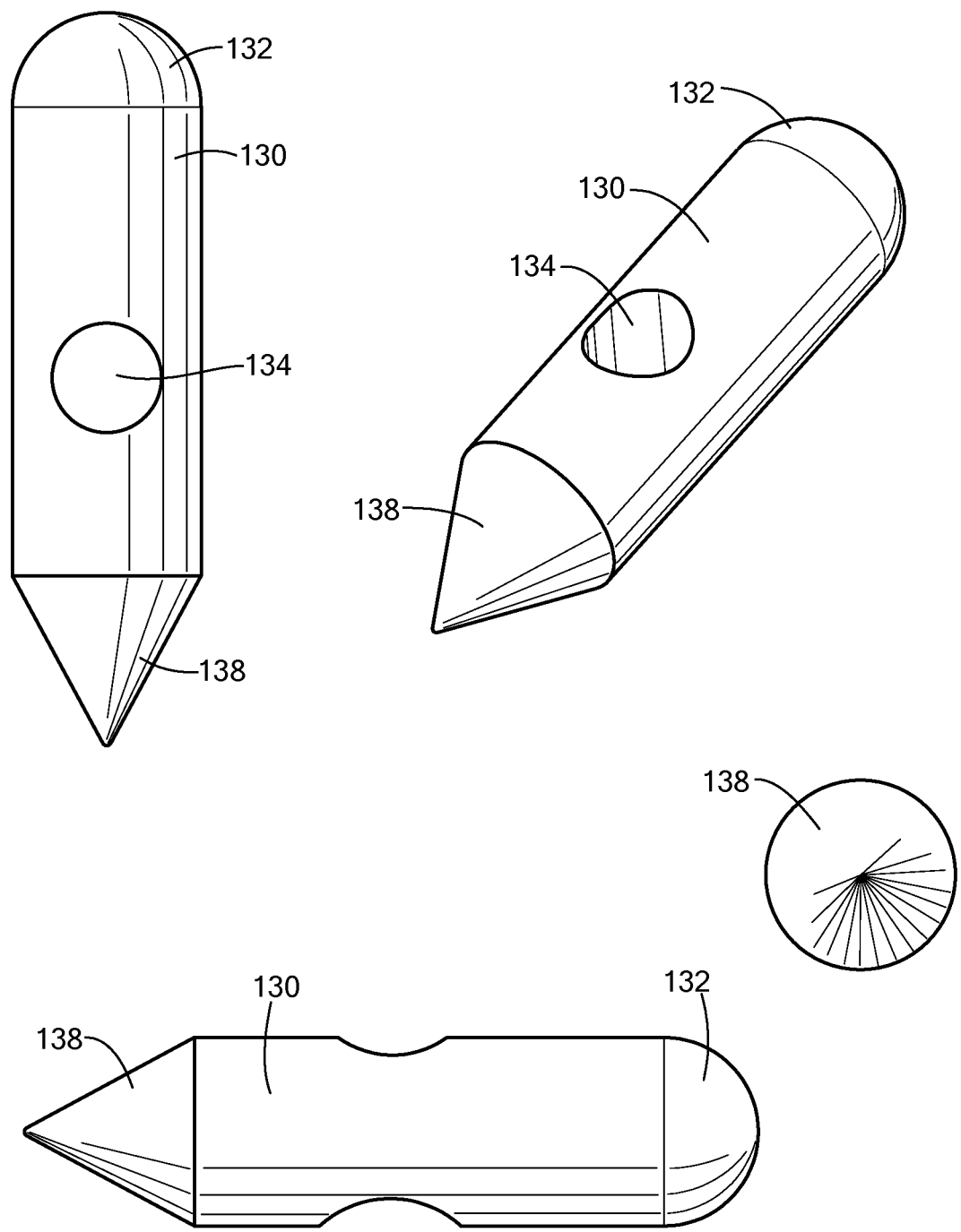
FIG. 53 illustrates top, front, side and isometric views of a needle having a cylindrical profile, in accordance with embodiments of the present invention.
Figure 54:
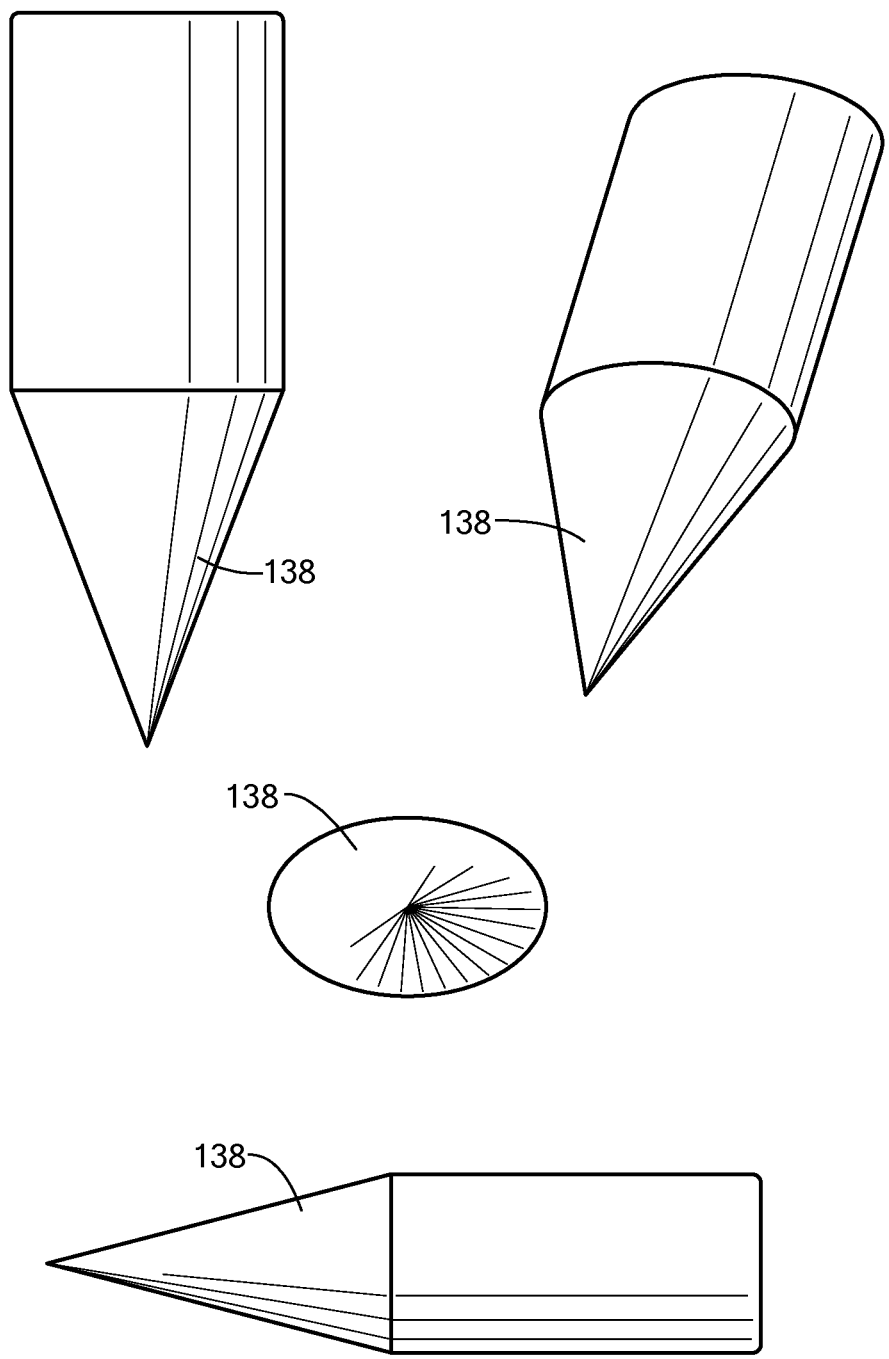
FIG. 54 illustrates top, front, side and isometric views of a needle having an elliptical profile, in accordance with embodiments of the present invention.
Figure 55:
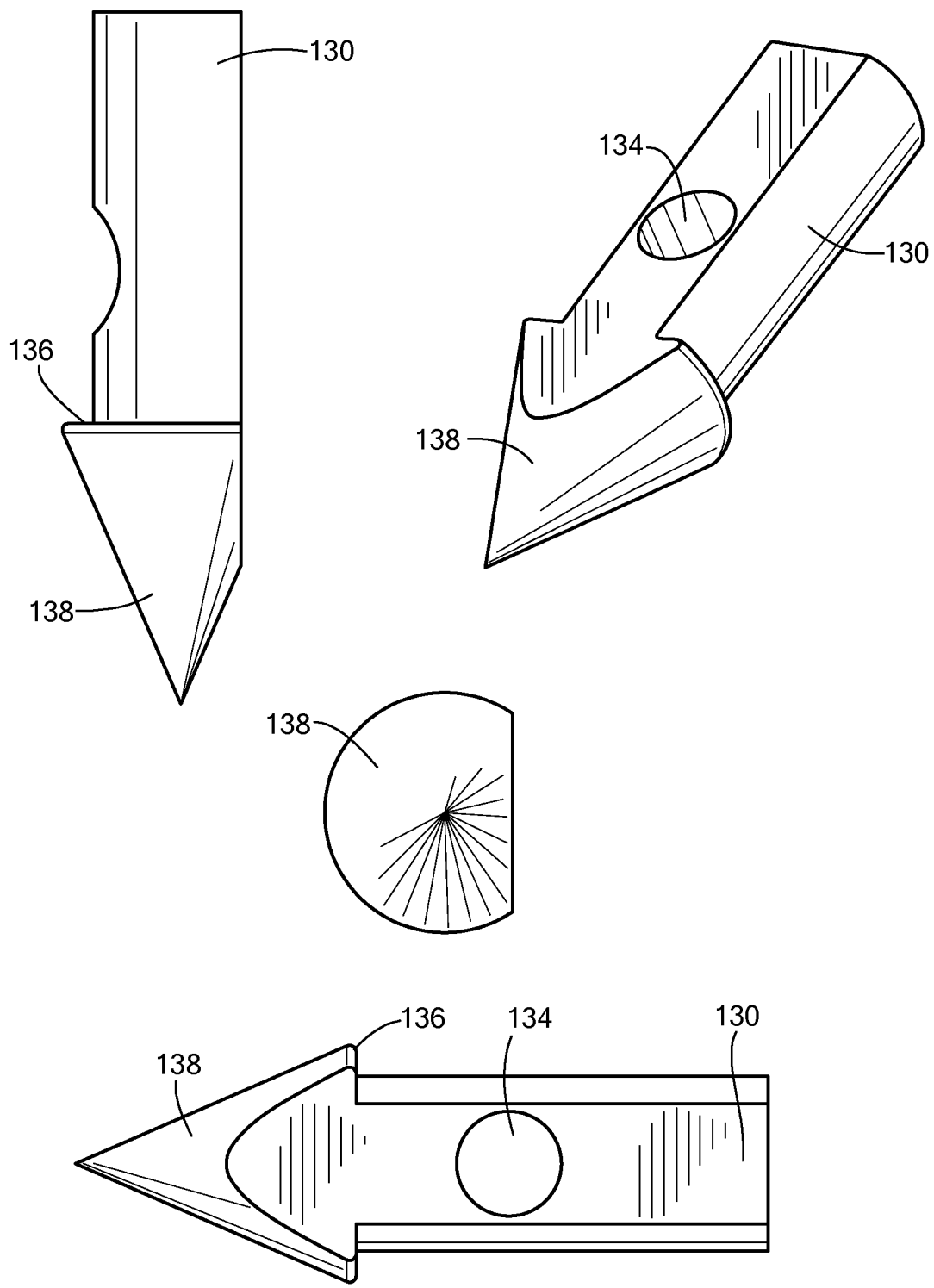
FIG. 55 illustrates side, front, top and isometric views of a needle, in accordance with embodiments of the present invention.
Figure 56:
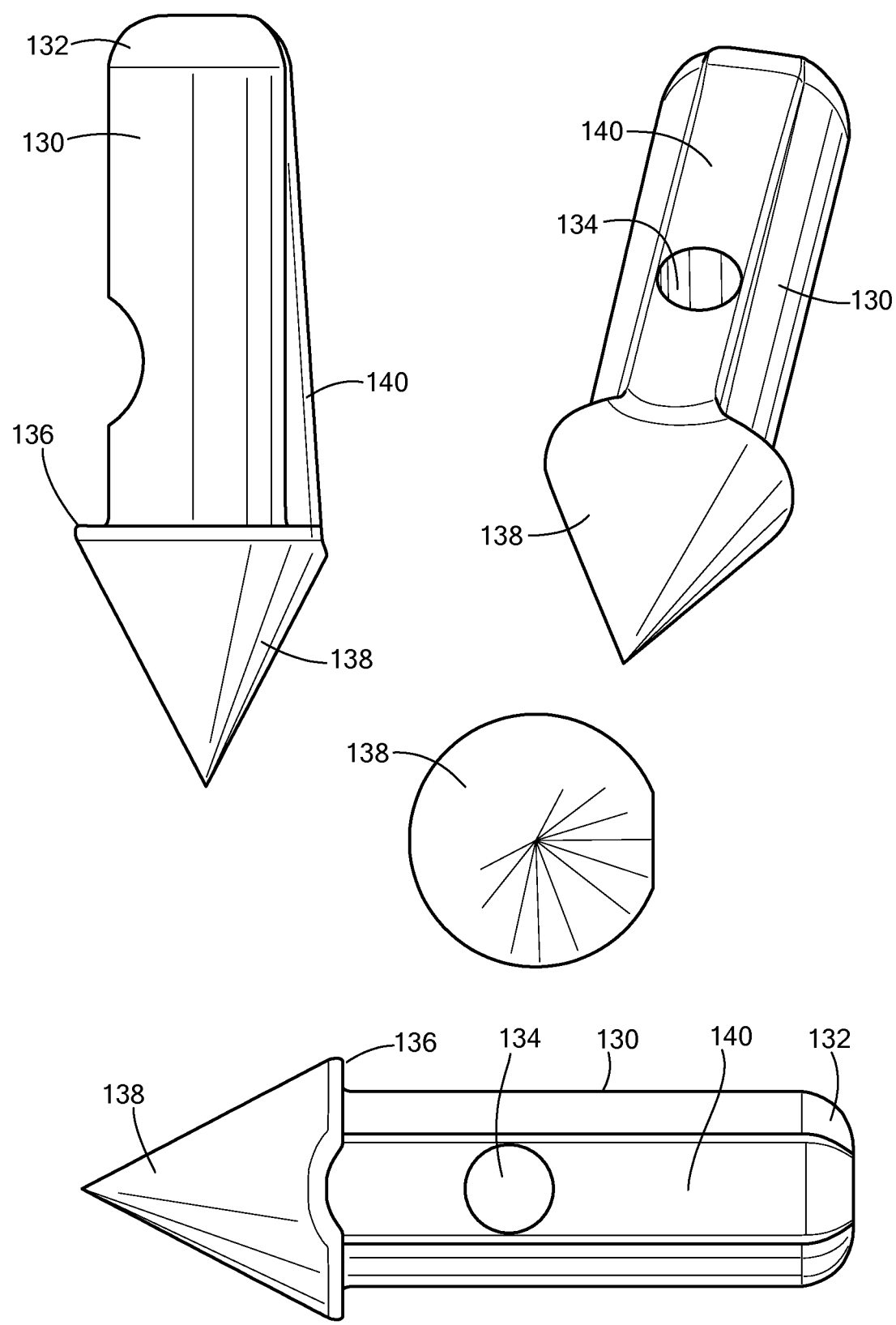
FIG. 56 illustrates side, front, top and isometric views of a needle, in accordance with embodiments of the present invention.

With continued reference to FIGS. 50-56, in one embodiment, needle tip 108 includes a shoulder 136 and a penetrating tip 138 (FIGS. 51, 55 and 56). In this particular embodiment, shoulder 136 is adapted such that it rests on a distal portion of a driving member (i.e. the delivery system). In other embodiments, the distal end of needle tip 108 includes a penetrating tip 138 but no shoulder (FIGS. 50, 52 and 53). In yet other embodiments, the body portion 130 includes a raised portion 140 tapering from shoulder 136 to a proximal end of needle tip 108 (FIGS. 51 and 56). In this particular embodiment, raised portion 140 is designed to engage with a slot within a needle driver 312 (FIGS. 70, 71 and 73) to prevent needle tip 108 from rotating relative to the driver 312 and damaging suture 104. Moreover, raised portion 140 may taper to reduce the profile of both the needle and the emanating suture during penetration. Thus, suture 104 is permitted to shelter behind shoulder 136. In some embodiments, needle 108 includes a cylindrical profile (FIG. 53). In other embodiments, needle 108 includes an elliptical profile (FIG. 54). The elliptical profile reduces the needle profile along the long axis to provide increased surface area for securing the needle tip on the posterior side of the intra-arterial foot 102. In other embodiments, needle 108 includes a cylindrical profile having a flat edge (FIG. 55). In yet other embodiments of needle tip 108 includes shoulder 136 and body portion 130 includes a flat edge (FIG. 56).

With reference again to FIGS. 15 and 16, in conjunction with FIGS. 1 and 2, a method of use and operation of closure system 100 will be described in detail. Closure system 100 is positioned on a distal end of a delivery system 300 and advanced within the lumen of artery 200 via a delivery sheath 150. As illustrated by FIG. 15, flexible wing 112 of intra-arterial foot 102 is folded within delivery sheath 150 and is deployed as it emerges from delivery sheath 150 within the lumen of artery 200 (FIG. 16). Intra-arterial foot 102 is tethered in position by two independent sutures 104 and bolsters 106. Each suture 104 includes a bolster 106 at its proximal end and a needle 108 at its distal end. In accordance with the present disclosure, delivery system 300 drives needle 108, and therefore suture 104, to move distally in a straight, linear pathway through arterial wall 204. Such movement drives needle tip 108 (and suture 104), through intra-arterial foot 102 and is ejected on the posterior side of intra-arterial foot 102. A shear force is then applied to suture 104, pulling sutures 104 into a channel 111 within intra-arterial foot 102 and generating a tensile force within the suture. The tensile force in suture 104 secures the intra-arterial foot 102 on the luminal surface 206 of artery 200. This tensile force additionally pulls bolsters 106 against the adventitial surface 208 of artery 200. Moreover, needle tips 108 are anchored against the posterior surface of intra-arterial foot 102 in response to the applied tension on the sutures 104. The tension applied to the sutures 104 bring about a closure of the arteriotomy 202. In particular, bolsters 106 distribute the tension on the suture such that the wound edges 203a and 203b are brought into alignment and/or apposition. Delivery system 300 is then removed leaving behind the secured closure system 100 with arteriotomy 202 sealed by the intra-arterial foot 102.

Figure 66:
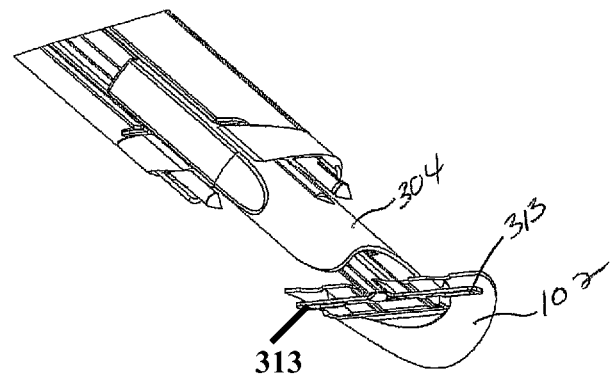
FIG. 66 is an isometric side view of a closure device attached to a delivery device, in accordance with embodiments of the present invention, with the closure device shown in cross section.
Figure 67:
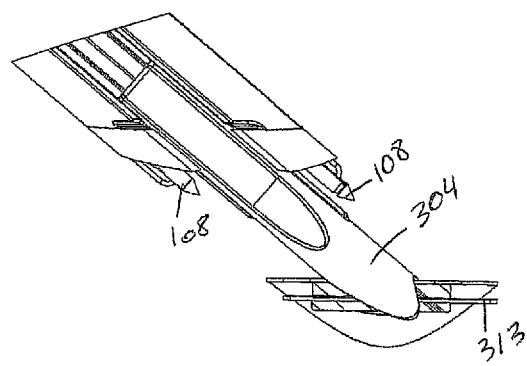
FIG. 67 is another isometric side view of the closure device and delivery device of FIG. 66.

With reference to FIGS. 66 and 67, an exemplary delivery device and method will now be described in detail. Delivery device 300 includes generally a wound spreader, a ribbon capture and release component and a needle driver having an ejection pin. As already described herein above, the closure device 100, in accordance with the present disclosure, is attached to the distal end of the delivery device 300 and is driven into position via a delivery sheath 150. When the intra-arterial foot component 102 exits procedural sheath 150, it opens, spreading open to effect a tamponade affect of the intra-arterial foot 102 to control arterial bleeding (FIGS. 15 and 16). In one embodiment, the spreading of intra-arterial foot 102 is a result of the elastic properties of intra-arterial foot 102. In an alternative embodiment, intra-arterial foot 102 may be actively spread, once deployed from the procedural sheath, by applying tension to spring clips 308, which are attached to the lateral extremities of the flexible wings 112 (FIG. 63). Clips 308 attached to a lateral flexible wing 112 performs a second important function of retracting the lateral wound edges 203a and 203b of arteriotomy 202.

Typically, dilated arteriotomies are configured in a circumferential orientation, transverse to the longitudinal axis of artery 200. Thus, applying lateral traction to the wound edges 203a, 203b of arteriotomy 202 has the effect of bringing the wound edges towards apposition. In accordance with the present disclosure, a wound spreader component controls the positioning of the wound edges 203a, 203b aids the tamponade of flexible wings 112 of intra-arterial foot 102. This positioning of wound edges 203a and 203b helps to facilitate the ability to accurately deploy needle 108 and sutures 104 relative to the controlled position of wound edges 203a and 203b. Furthermore, it centralizes the closure device 100 relative to the arteriotomy.

Figure 57:
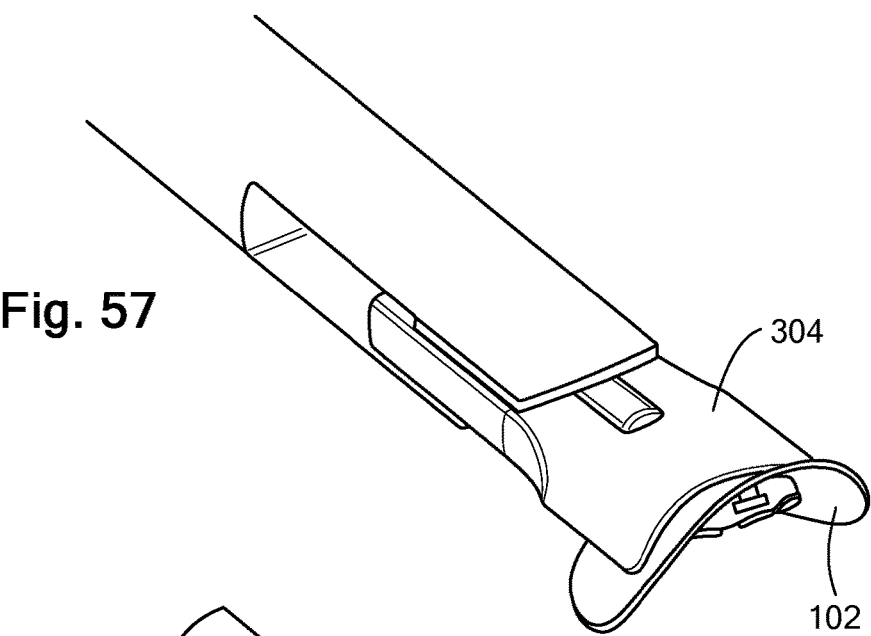
FIG. 57 illustrates an isometric view of a wound spreader and an intra-arterial foot attached to the distal end of a delivery device, in accordance with embodiments of the present invention.
Figure 58:
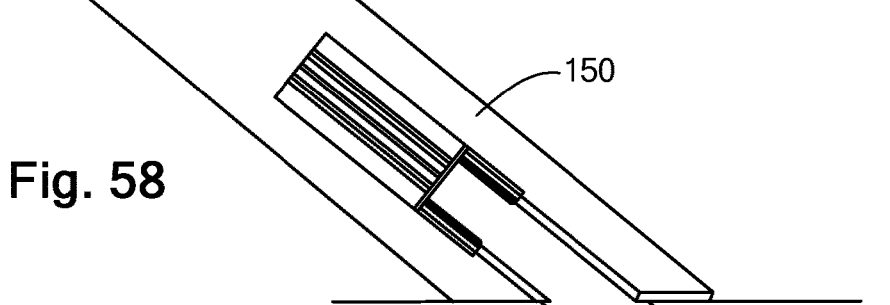
FIG. 58 is a side view of the delivery device of FIG. 57 positioned within a delivery sheath and having the distal end advanced into the lumen of an artery, in accordance with embodiments of the present invention.
Figure 59:
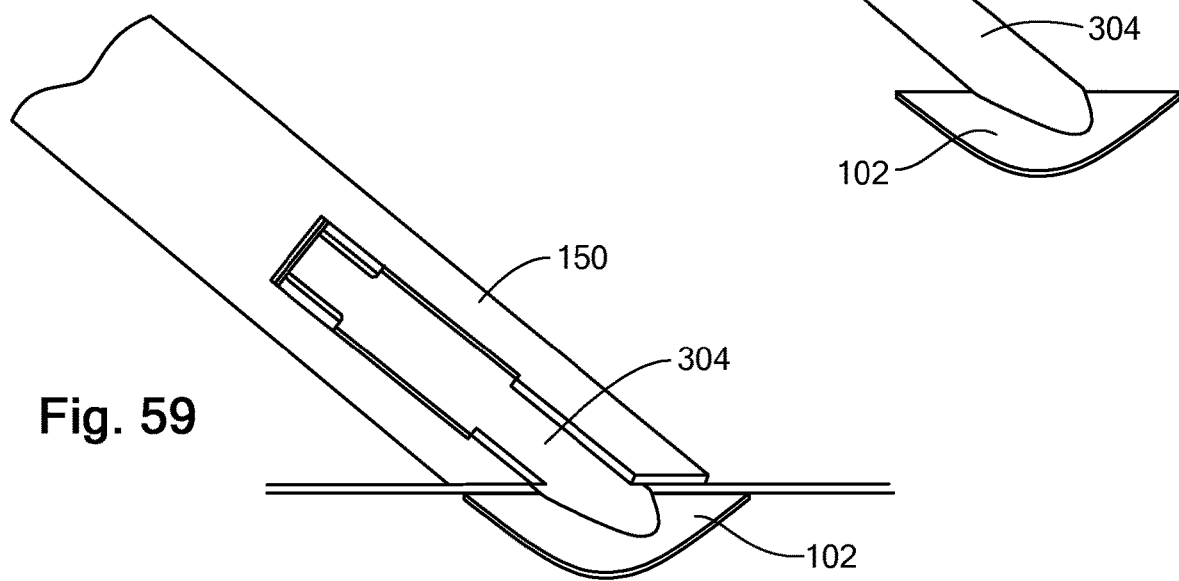
FIG. 59 is a side view of the delivery device of FIGS. 57 and 58 illustrating the wound spreader in a retracted position, engaging the wound edges of an arteriotomy.

With reference to FIGS. 57-59, a portion of an exemplary delivery device 300 is illustrated, in accordance with one embodiment of the present disclosure. Delivery device 300 includes a foot anchor 358 and a wound spreader component 304 adjacent to foot anchor 358. Delivery device 300 is adapted for delivering closure device 100 for closing wound edges 203a and 203b of an arteriotomy 202, in a manner described in detail herein below.

In some embodiments, wound spreader component 304 includes a flexible member forming an elliptical profile. The spreader component 304 may be oriented in the direction relevant to the appropriate or desired wound retraction. In some particular embodiments, the major diameter of wound spreader 304 may be substantially the same as the outermost diameter of intra-arterial foot 102. Moreover, the major diameter of wound spreader 304 may be substantially the same diameter as the diameter of delivery sheath 150. In other embodiments the major diameter of the wound spreader is substantially larger than the diameter of delivery sheath 150. In such embodiments, the compressible nature of the spreader allows the spreader to fit within the sheath.

With continued reference to FIGS. 57-59, foot anchor 358 is releasably attached to intra-arterial foot 102. More specifically, foot anchor 358 anchors intra-arterial foot 102 during its delivery and positioning against the arteriotomy.

As illustrated by these figures, wound spreader 304 is adjacent to foot anchor 358, wherein a distal end of the wound spreader 304 is substantially abutting a portion of intra-arterial foot 102. Thus, when the closure system of the present disclosure is used in arterial application, wound spreader 304 helps minimize blood loss into the surrounding soft tissues. In particular, when the introducer sheath 150 is removed from artery 200 prior to deploying the intra-arterial foot 102, spreader component 304 functions as a temporary seal, prior to securing the intra-arterial foot on the arteriotomy. As delivery sheath 150 is removed from the arteriotomy, the arteriotomy conforms substantially to the geometry and shape of wound spreader 304.

With reference to FIGS. 58 and 59, in operation, wound spreader 304 and intra-arterial foot 102 are advanced through delivery sheath 150 and into the lumen of an artery. Wound spreader 304 and foot anchor 358 are then retracted proximally such that the wound spreader 304 controls the wound edges 203a and 203b of arteriotomy 202 and intra-arterial foot 102 is positioned against the internal wall of the artery. A needle housing (not shown), housing needle drivers and positioned within delivery sheath 150, is then positioned against the exterior wall of the artery. Once intra-arterial foot 102 is positioned in the internal surface of the arterial lumen 206 juxtaposed with arteriotomy 202, a "sandwich" is created, wherein arterial wall 204 is held between intra-arterial foot 102 and the needle housing (FIG. 59).

Figure 68:
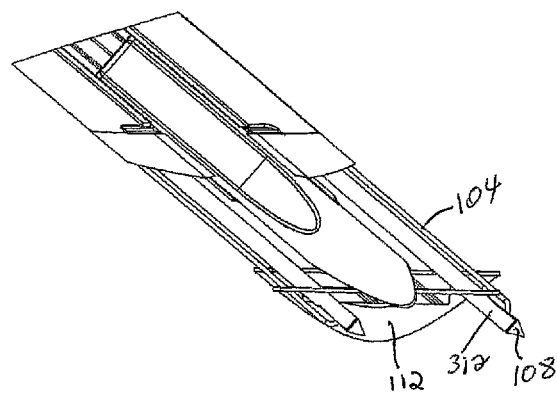
FIG. 68 is an isometric side view of the delivery device of FIGS. 66 and 67, illustrating the needle drivers in an advanced position.

In accordance with the embodiment illustrated by FIGS. 29, 59, and 68 the intra-arterial foot is held in its correct position against the internal arterial surface (i.e. internal wall), centrally located relative to the arteriotomy. Additionally, the needle/suture subassembly and needle driver assembly 312 have unobstructed and direct passage through arterial wall 204 into intra-arterial foot 102.

Wound spreader component 304 may be manufactured from a semi compliant material such that it can deform to fit within delivery sheath 150 during delivery through the percutaneous tissue (not shown by the figures) and into arterial lumen 206. Once positioned in arterial lumen 206, wound spreader 304 is exposed distally relative to delivery sheath 150 and is deployed to its initial profile. Delivery sheath 150 is then withdrawn until the delivery sheath is no longer within the arteriotomy, and is replaced by the geometry of wound spreader 304. As such, arteriotomy 202 moves from a first geometry (e.g. circular) to a second geometry (e.g. elliptical) to conform to the shape of spreader component 304. It is noted that bleeding is controlled during this withdrawal and transition between geometries by the tamponade of both delivery sheath 150 and spreader 304.

Figure 60:
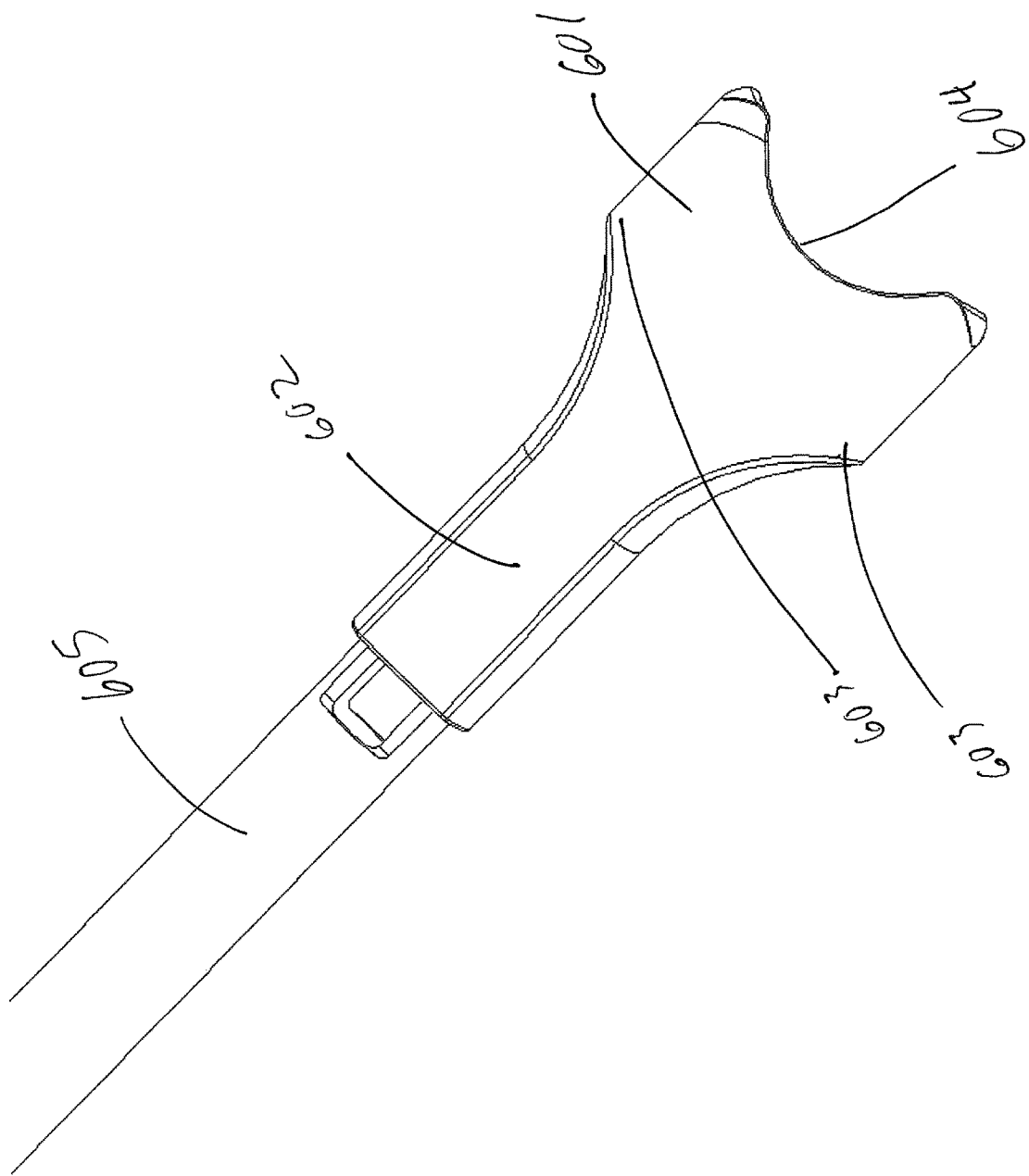
FIG. 60 illustrates a perspective view of a wound spreader according to embodiments of the present invention.

FIG. 60 illustrates a perspective view of a wound spreader according to embodiments of the present invention. The wound spreader 601 is a magnified view of wound spreader 304 depicted in FIG. 57. Like wound spreader 304, wound spreader 601 may be incorporated with the anchor assembly of a delivery device. The spreader assists with spreading the wound edges and additionally assists in minimizing blood loss into the surrounding soft tissue when the introducer sheath of the delivery device is removed from the artery, but prior to the intra-arterial foot being secured in place. In some embodiments, the spreader occupies substantially the entire wound space once the sheath is removed. Sheath 601 is geometrically designed such that the shoulders 603 of the spreader are spread further apart than the neck 602 of the spreader. The increased width of the spreader in the shoulder region is designed to be substantially as wide as the diameter of the introducer sheath delivering an intra-arterial foot in some embodiments. The width of the spreader maintains a lateral tension in a wound such that the edges of the wound, for example edges 203a and 203b shown in FIG. 2, are drawn closer together. By occupying the space of the wound and by drawing the edges of the wound together the wound spread helps minimize fluid flow through the wound. The shape of the wound spreader may be an elliptical shape, and the spreader may be composed of a compressible material.

Figure 61:
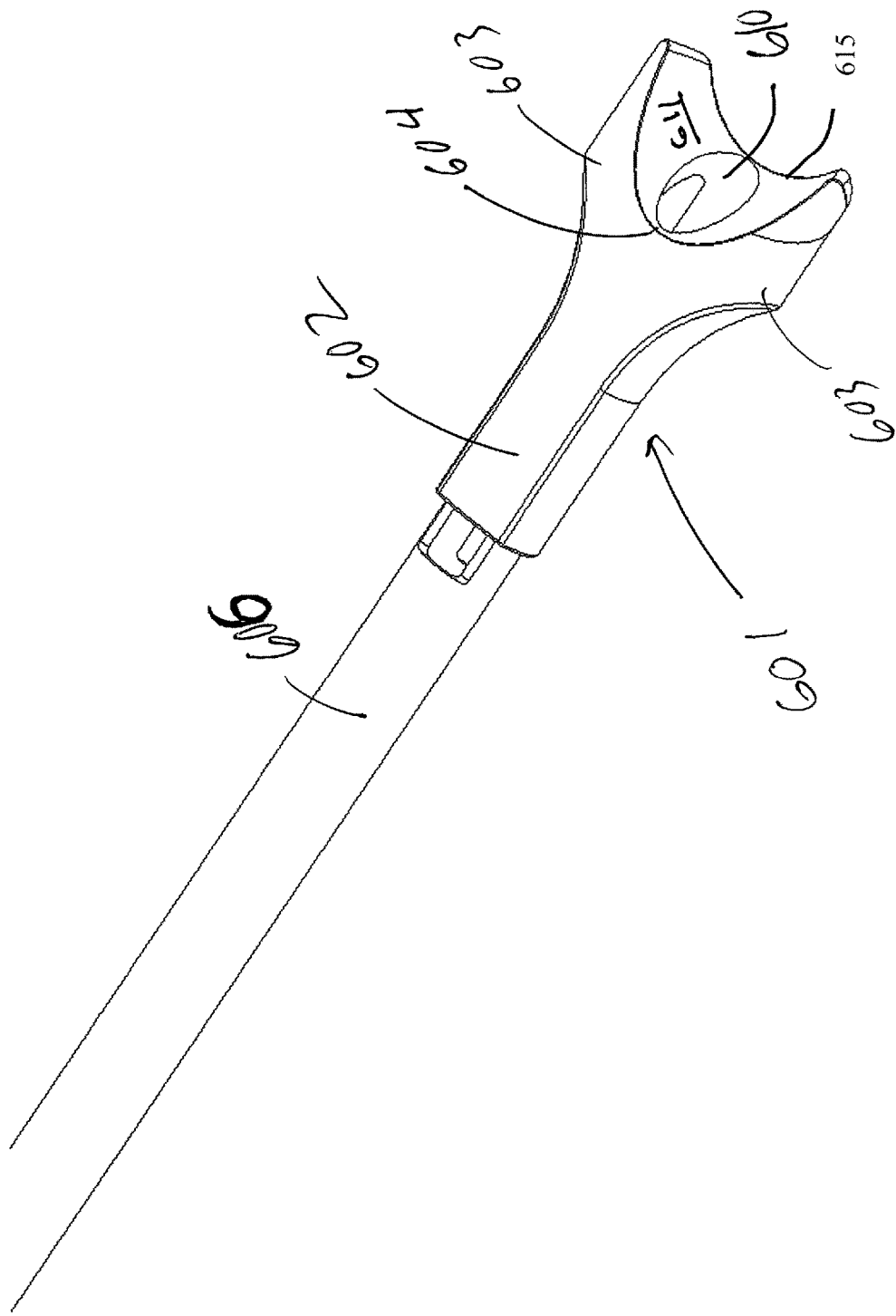
FIG. 61 illustrates a perspective view of the wound spreader of FIG. 60 from below the spreader.
Figure 62:
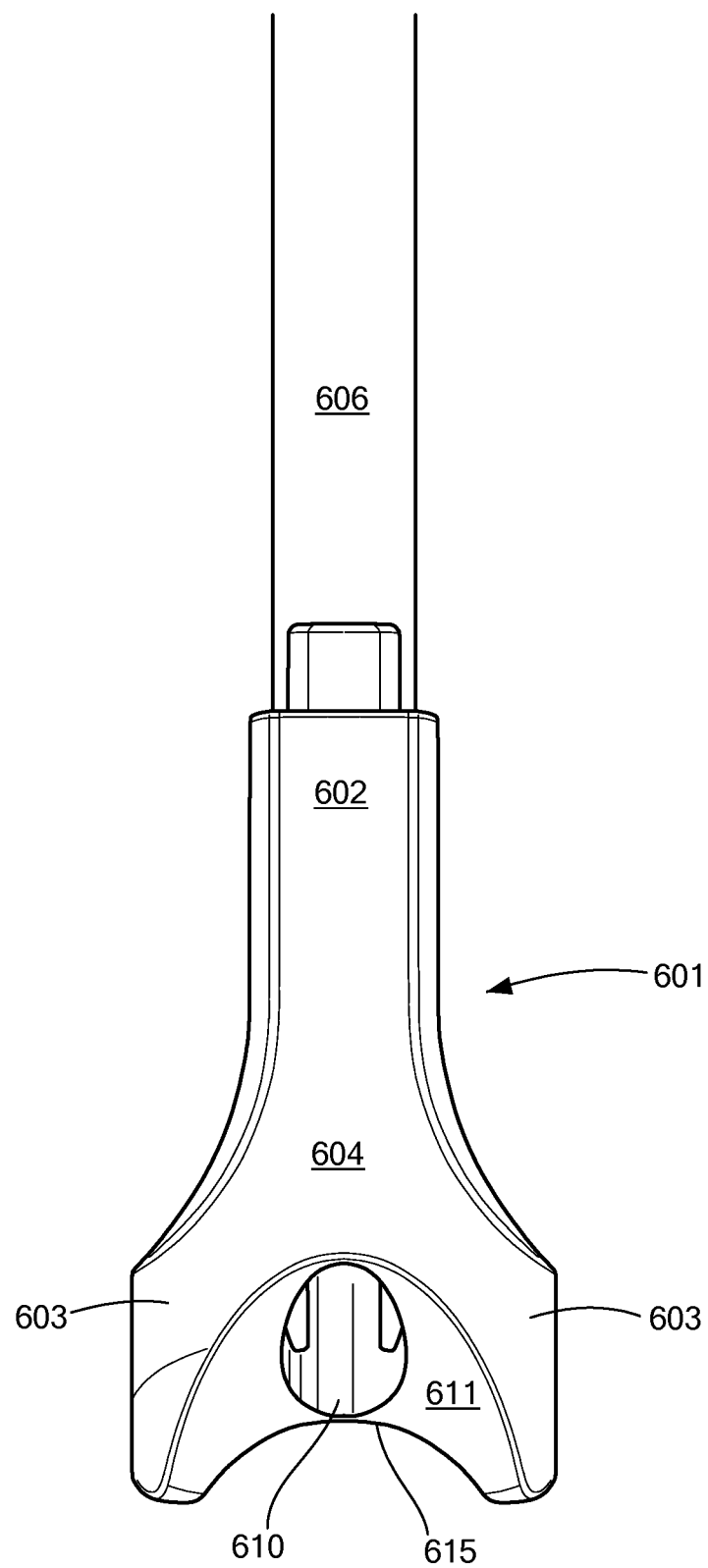
FIG. 62 illustrates a bottom view of the wound spreader of FIG. 60.

FIG. 61 illustrates a perspective view of the wound spreader of FIG. 60 from below the spreader, and FIG. 62 illustrates a bottom view of the wound spreader of FIG. 60. As demonstrated in FIGS. 61 and 62, spreader 601 may include arcuate edges 604 and 615, conforming to the shape of the wing of the intra-arterial foot. Edges 604 and 615 may recede to different depths into respective surfaces of the spreader such that face 611 of the spreader is at an angle or taper. Additionally, the wound spreader generally includes an opening 610, which provides a passageway through which an object such as a foot anchor, ribbons or other objects interacting with the intra-arterial foot may pass. The spreader is generally coupled to an extension of the anchor assembly 606 at the neck 602 of the spreader in a co-axial alignment. In some embodiments the axial extension 606 of the anchor assembly is coupled to an interior region of spreader 601. In other embodiments, the extension may be coupled to an exterior portion of the anchor assembly. However, as demonstrated, the extension 606 and spreader 601 maintain a passageway for entry and exiting of various elements.

Figure 64:
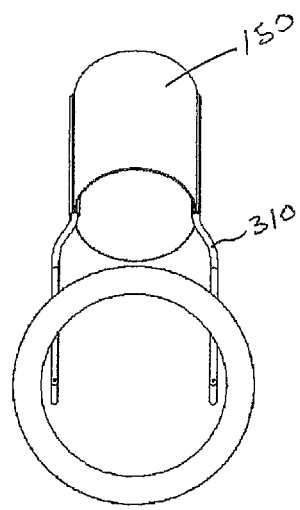
FIG. 64 is an end view of a delivery sheath having spreader tangs for spreading the wound edges an arteriotomy.
Figure 65:
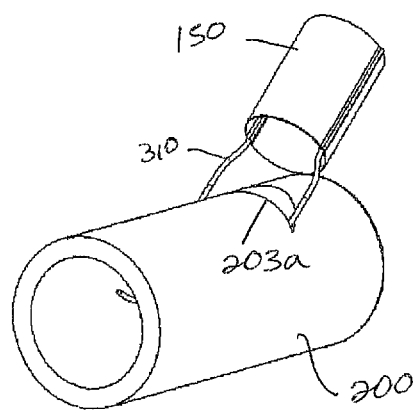
FIG. 65 illustrates an isometric view of the delivery device of FIG. 64.

With reference to FIGS. 64 and 65, an alternative method of spreading and orienting wound edges 203a, 203b is illustrated wherein delivery device 300 includes spreader tangs 310 having a length and a distal end positioned on a side portion of delivery sheath 150. In this particular embodiment, delivery sheath 150 is a tri-lumen extrusion (not shown): a large inner lumen for providing access to various surgical instruments and delivery device 300, and two smaller lumens for housing spreader tangs 310. During delivery, spreader tangs 310 are retracted back inside procedural sheath 150. Once positioned inside artery 200, tangs 310 are advanced out to the front end of delivery sheath 150 then sprung outwardly such that once they exit distally from delivery sheath 150, the distance between them would be greater than the distance between them when contained inside delivery sheath 150. This added width assists to actively retract and spread the wound edges 203a and 203b.

In one embodiment, tangs 310 include a floppy, atraumatic tip at the distal end. An atraumatic tip ensures that tangs 310 are advanced into internal lumen 206 like guide wires, with minimal trauma to the lumen during delivery and use. The length of tangs 310 eliminates the risks of tangs 310 accidentally being pulled out of arteriotomy 202 during the spreading and orientation of wound edges 203a and 203b. In other embodiments, tangs 310 include a mating feature for securing them to procedural sheath 150 such that when tangs 310 exit from the front end of sheath 150, their orientation is fixed to one plane, not free to rotate. This configuration ensures that tangs 310 apply traction to wound edges 203a and 203b in the transverse plane only.

Figure 69:
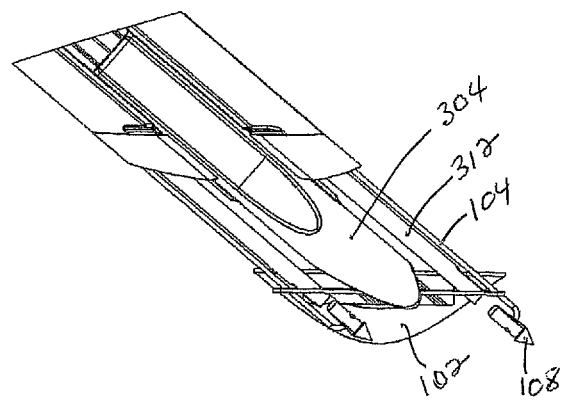
FIG. 69 is an isometric side view of the delivery device of FIGS. 66-68 illustrating the ejection and release of the needle tip/suture assembly, in accordance with embodiments of the present invention.
Figure 77:
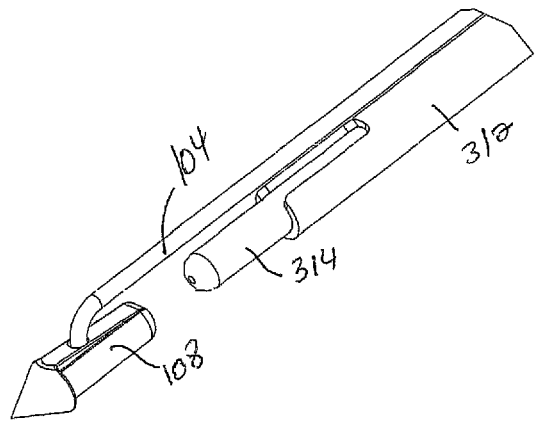
FIG. 77 is an isometric view of an ejector pin ejecting the needle/suture subassembly of FIG. 76.
Figure 78:
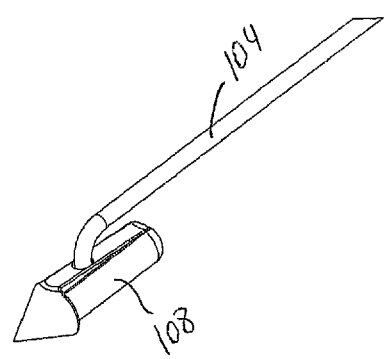
FIG. 78 is an isometric view of the needle/suture subassembly of FIG. 76, in accordance with embodiments of the present invention.
Figure 79:
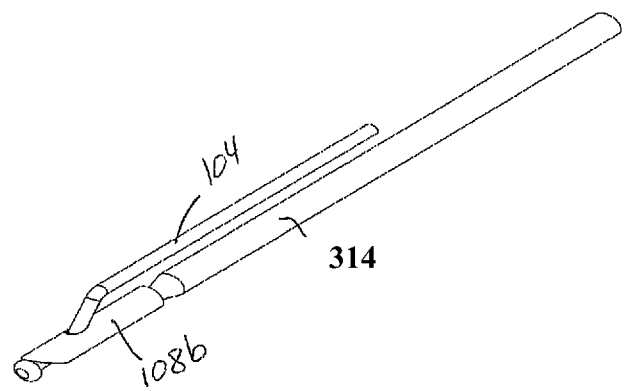
FIG. 79 is an isometric view of an ejector pin in position next to the needle/suture subassembly of FIGS. 73 and 74, in accordance with embodiments of the present invention.
Figure 80:
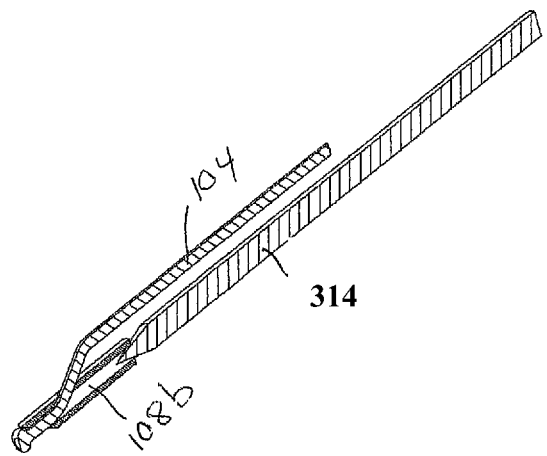
FIG. 80 is a cross-sectional view of the assembly illustrated by FIG. 79.
Figure 81:
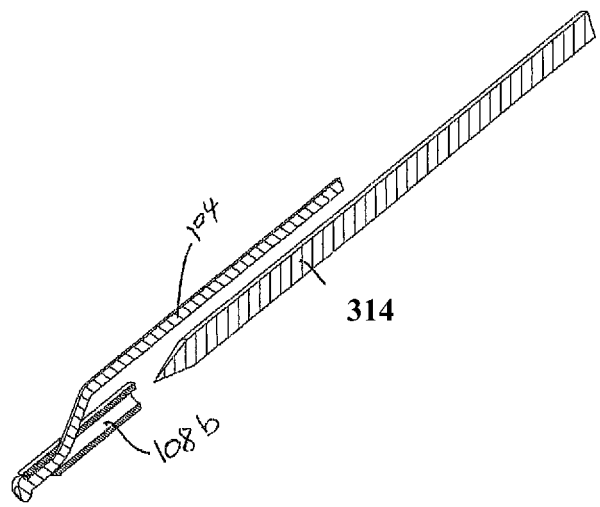
FIG. 81 is a cross-sectional view of the needle/suture subassembly of FIGS. 79 and 80 ejected from the needle driver.

With reference now to FIGS. 66-68, delivery device 300 further includes needle drivers 312 for driving needle 108 and suture 104 through intra-arterial foot 102. Each needle driver 312 includes an ejector pin, such as pin 314 depicted in FIG. 77, contained within needle driver 312 for disengaging the needle/suture (FIGS. 69 and 77). In some embodiments, needle tip 108 is adapted to be re-oriented from a first concentric alignment with needle driver 312 to a second horizontal position once free from driver 312. More in particular, and as described herein above, needle tip 108 forms a "T" configuration with suture 104.

Figure 75:
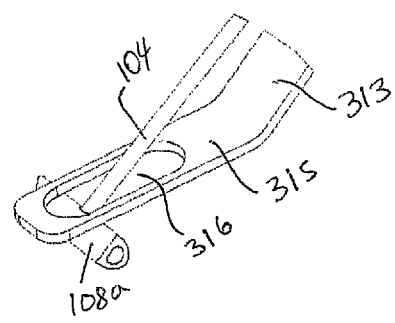
FIG. 75 is an isometric view of the needle/suture subassembly of FIG. 73 deployed within the opening of the capture ribbon component.

With particular reference to FIGS. 67 and 68, in conjunction with FIGS. 73 and 74, after the intra-arterial foot 102 is in position, needle drivers 312 are advanced through the arterial wall and a portion of the intra-arterial foot to drive the needle/suture subassembly to a posterior side of the intra-arterial foot. More in particular, FIG. 68 illustrate needle divers 312 in an advanced position passing through a profiled opening 316 of a capture and release ribbon component 313 (component 313 shown in FIGS. 73 and 74). As shown in various figures, including FIGS. 66-69 and 71, the delivery device may deploy a pair of ribbons 33 through the channel in the intra-arterial foot. The distal end of the ribbons, particularly tab 315, may project in opposing directions, such that one ribbon forms an acute angle with respect to the anchor and sheath and the other ribbon forms an obtuse angle with respect to the sheath. In some embodiments, the acute angle is about 40 degrees. In certain embodiments, the obtuse angle is about 140 degrees. Once needle/suture subassembly passes through opening 316 on tab 315 of ribbon 313, ejector pin 314 ejects the needle tip 108 (FIG. 69). After ejecting needle tip 108, each needle driver 312 and ejector pin 314 are retracted from the intra-arterial foot 102 (i.e. moved in a proximal direction) into the needle housing. Moreover, each needle tip 108 has a length substantially larger than any diameter of the profiled opening 316 of capture ribbon component 313. Thus, once needle tip 108 is ejected from needle driver 312 through profiled opening 316, the needle tip 108 cannot be removed back because of its dimension. Thus, suture 104 remains threaded through the profile opening 316 of capture ribbons 313 (FIG. 75). Furthermore, once a significant amount of the suture extends beyond the capture ribbon, the suture may have enough slack to ensure that the shuttle does not slip back through the hole in the capture ribbon. Accordingly, some embodiments of the present invention may be provided without a T configuration.

With reference to FIGS. 70-72, and FIGS. 73-75, delivery device 300 further includes at least two capture and release ribbon components 313 extending laterally for capturing, retracting and locking the deployed needle/suture subassembly. Capture and release ribbon component 313 includes a first longitudinal portion attached to a movable mount (not shown) and a second tab portion 315 extending from the first longitudinal portion. Second tab portion 315 includes the profiled opening 316. As described hereinabove, profile opening 316 is adapted for receiving and engaging the needle/suture subassembly.

Second tab portion 315 further includes a lock ribbon (e.g. an aperture) (not shown) for receiving and locking a longitudinal member for holding the intra-arterial foot in place during the driving of the needle/suture subassembly.

In operation, during actuation of delivery system 300, each needle driver 312 advance distally to drive each needle/suture subassembly through arterial wall 206, intra-arterial foot components and through profile opening 316 of capture and release ribbon component 313 to a posterior side of intra-arterial foot. Each ejector pin 314 then ejects shuttle-suture subassembly 108a out through the side of needle driver 312 leaving the shuttle-suture subassembly remaining threaded through capture ribbons 313 (FIG. 75). In one embodiment, the timing of this movement could be configured to retract driver 312 and partially retract capture ribbon 313 back up through the center of intra-arterial foot 102.

Figure 70:
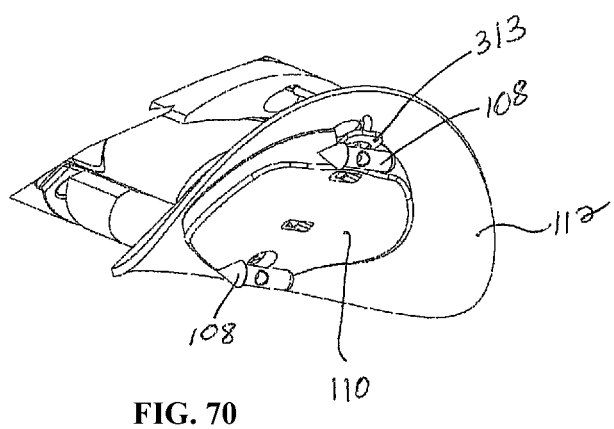
FIG. 70 is an isometric bottom view of the intra-arterial foot of FIGS. 8 and 9 with needles anchored to an underside portion of the intra-arterial foot.
Figure 71:
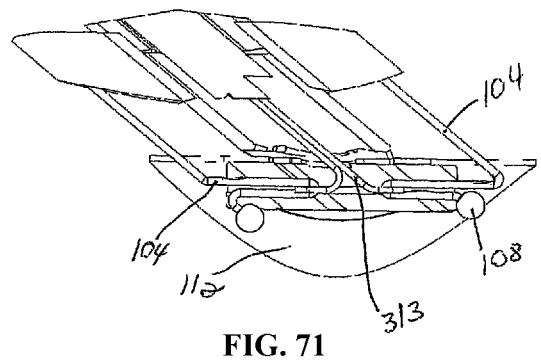
FIG. 71 is a cross-sectional view of the intra-arterial foot of FIGS. 66-70 illustrating a capture ribbon in a retracted position.

With particular reference to FIG. 71, the second tab portion of capture and release ribbon component 313 are moved laterally channel 111 of intra-arterial foot 102 in response to a longitudinal retraction of the first longitudinal portion of capture ribbons components 313. This retracting action pulls a portion of the suture/needle subassembly into channel 111. The re-oriented needle tip 108 acts as an anchor and abuts against the underside and edge of intra-arterial foot 102 (FIG. 70). As noted above, some embodiments of the present invention may be provided without a T configuration and the suture slack may be relied upon to prevent the shuttle from slipping back through the hole in the capture ribbon. Once needle 108 is effectively stationary (i.e. blocked from further travel), suture 104 connected to extra-arterial bolster 106 outside artery 200 will continue to pull into the artery 200 as capture and release ribbon component 313 continue to retract into channel 111. This action will also pull extra-arterial bolster 106 down onto the external surface 208 of artery 200 (FIG. 72). As illustrated by FIGS. 71 and 72, retraction of ribbon components 313 will pull suture 104 into channel 111 and double suture 104 on itself. More in particular, suture 104 is partially pulled into the space (i.e. channel 111) previously occupied by the retracting ribbon capture components 313.

More in particular, and with continued reference to FIGS. 71 and 72, when capture and release ribbons component 313 pull the needle/suture subassembly, needle 108 is secured against a surface of intra-arterial foot 102 while suture 104 is doubled-up and secured within channel 111 of intra-arterial foot 102. Because the distal end of suture 104 (i.e. needle 108) is anchored against intra-arterial foot 102, when ribbon component 313 is retracted, a portion of suture 104 is advanced (i.e. pulled) and doubled within channel 111. This action creates an interference fit between suture 104 and channel 111 of intra-arterial foot 102. FIG. 72 illustrates intra-arterial foot 102 implanted in artery 200 with doubled up sutures 104 tethered into position, needle tips 108 anchored against the intra arterial foot, and external bolster 106 tightened onto the outer wall (i.e. external surface 208) of artery 200.

To accommodate variations in arterial morphology and wall thickness dimensions between patient populations, it is envisioned that the capture and release ribbon components 313 will disengage from suture 104 after the suture is positioned within channel 111 and/or when a predetermined load is reached. It is noted that the release will not be reached until the interference lock with the doubled up suture 104a is reached on both sides of intra-arterial foot 102. In view of the variations in arterial morphology the interference lock with the doubled up suture may be reached at various points in different patients or in vessels with different thicknesses and more arterial tissue with respect to other vessels.

Figure 76:
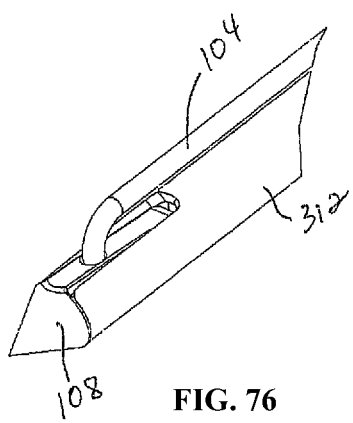
FIG. 76 is an isometric view of the needle of FIG. 51, having a suture attached thereto for forming a needle/suture subassembly, positioned on a distal end of a needle driver, in accordance with embodiments of the present invention.

With reference to FIGS. 76 and 77, in conjunction with FIG. 51, one embodiment of needle/suture subassembly is illustrated attached to a distal end of a driver 312. In this particular embodiment, needle tip 108, with suture 104 attached thereto, punctures the vessel wall during an operation and penetrates the foot and ribbons. This embodiment also incorporates a keying feature, which engages with a slot in the needle driver tube. This feature ensures orientation of the needle-tip and suture relative to the needle driver and prevents damage to the suture or suture/needle junction during assembly, deployment and ejection. The ramped back profile on the needle tip is designed to allow room for the suture to fold down to protect it from any shearing action during the firing through arterial wall and intra-arterial foot 102. Folding of the suture should also help to minimize the penetration force when passing through the arterial wall.

With reference to FIGS. 79-86, one embodiment of a needle-shuttle-suture subassembly attached to a distal end of pusher 314, in accordance with the present disclosure, is described. In the particular embodiment illustrated in FIGS. 79-86, pusher 314 is pointed to engage needle-shuttle suture subassembly 108b having a puncturing tip. In operation, pusher 314 is advanced to deploy through arterial wall 206 and into a recess (i.e. channel 111 within intra-arterial foot 102. During this actuation, pusher 314 and needle-shuttle/suture subassembly also pass through capture and release ribbon component 313 housed in intra-arterial foot 102, as described herein above with reference, for example, to FIGS. 74 and 75.

Figure 87:
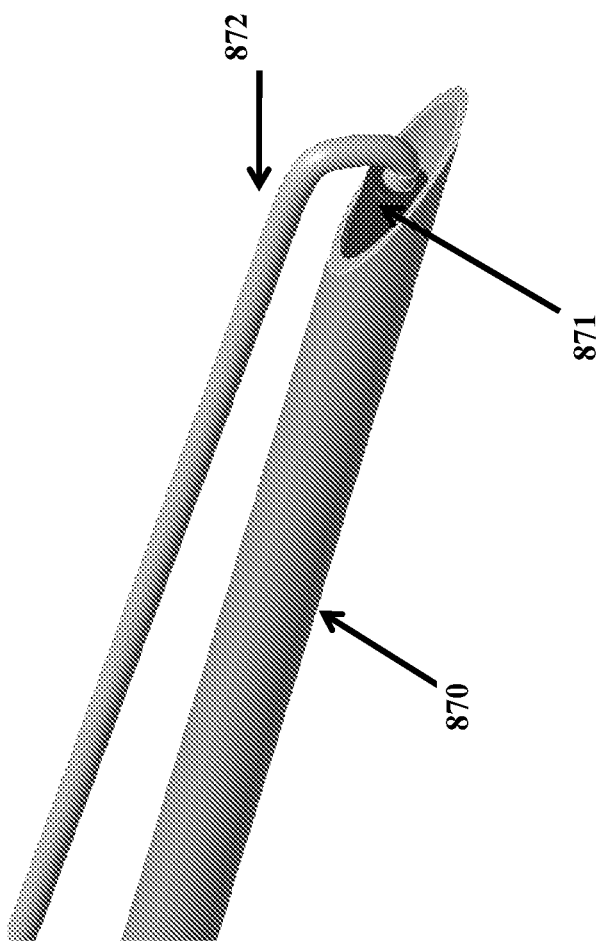
FIG. 87 illustrates a needle assembly in accordance with embodiments of the present invention.

FIG. 87 illustrates a needle in accordance with embodiments of the present invention. The needle demonstrates an embodiment that may be used as an alternative to the needle embodiments demonstrated in FIGS. 73, 76, and 79. The needle embodiment depicted in FIG. 87 may be used in combination with various delivery system embodiments of the present invention. The needle design depicted in FIG. 87, like the embodiment shown in FIGS. 76 and 79 engage a suture configured to extend axially from the needle. However, the needle embodiment depicted in FIG. 87 has a tubular needle 870 that is distinct and detachable from suture 872. Needle tube 870 may be ejected from the sheath of a delivery system, thereby piercing the vessel wall of an artery. Because the suture 872 is engaged with the needle 870 via shuttle 871 attached to suture 872, the suture will enter the vessel wall as the needle pierces the wall, in a manner similar to a thread attached to a sewing needle piercing a piece of fabric.

Figure 88:
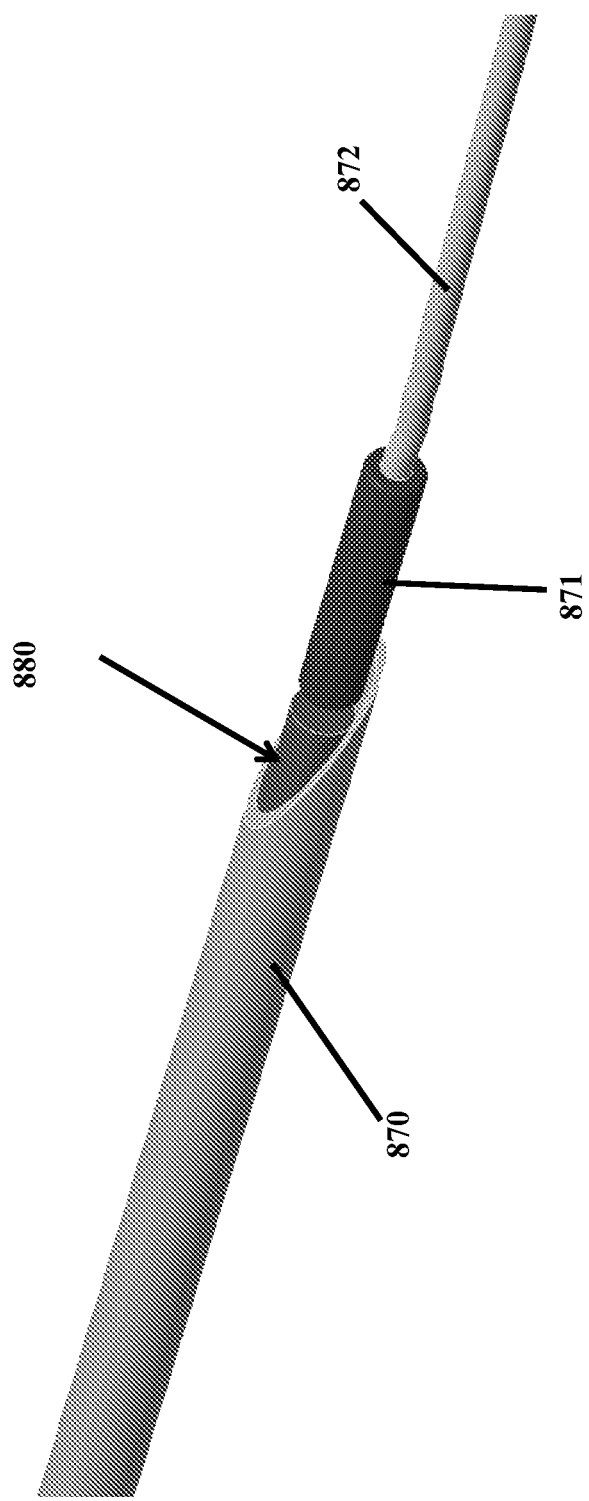
FIG. 88 illustrates the needle assembly of FIG. 87 during actuation.

FIG. 88 illustrates the needle of FIG. 87 during actuation. After needle 870 has penetrated a vessel wall, carrying suture 872 and shuttle 871 with it through the wall, pusher rod 880 may be translated through the hollow tube of needle 870 to eject and hence detach the suture and shuttle from the needle tube 870.

Figure 89:
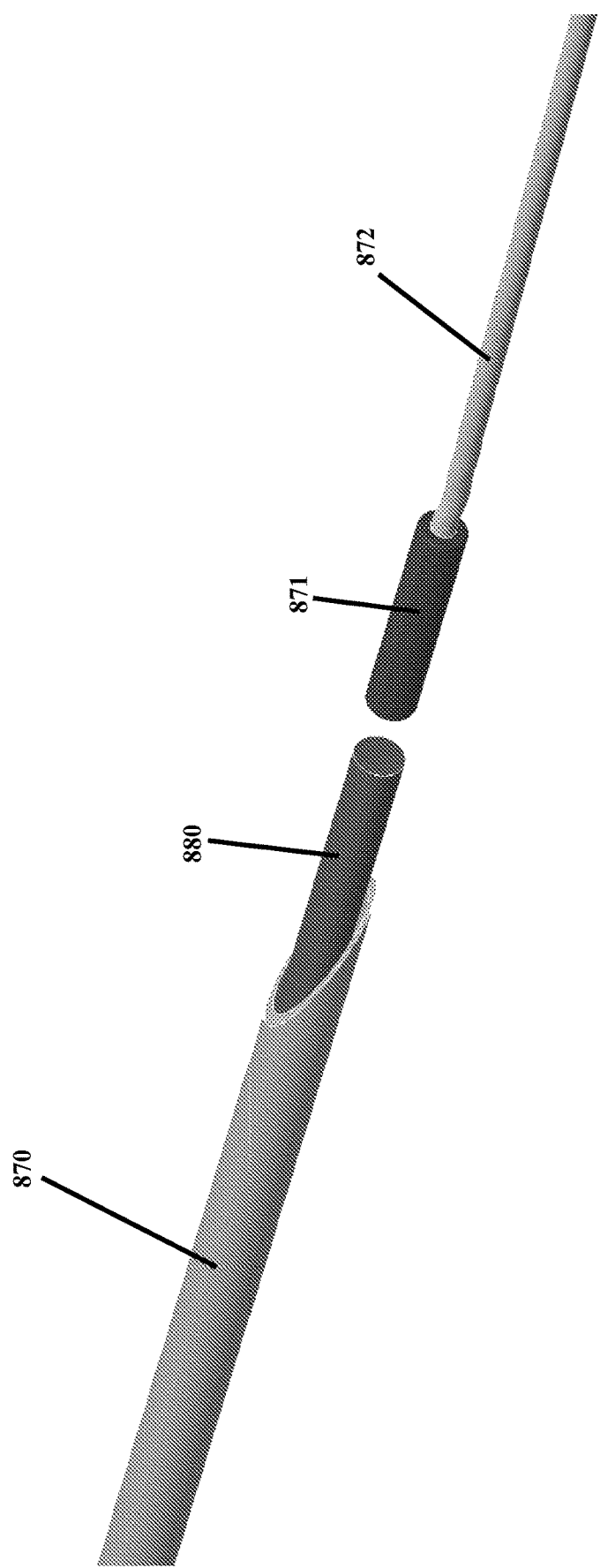
FIG. 89 illustrates the needle assembly of FIG. 87 after ejection of a suture.

As demonstrated in FIG. 89 pusher rod 880 may extend beyond the tip of needle 870 to effect complete ejection and detachment of suture 872 and shuttle 871 from needle 870. During an operating procedure, once the suture penetrates the vessel wall and is detached from the needle, the needle may be withdrawn from the artery. As previously demonstrated the needle may be aligned within the sheath of a delivery system so that it will penetrate a portion of the intra-arterial foot. In some embodiments, the needle penetrates a portion of the intra-arterial foot and a ribbon engaged with the foot through coaxially aligned apertures in the foot and ribbon. Accordingly, once the shuttle and suture are released from the needle and the needle is extracted, the shuttle and suture remain engaged with the foot and ribbon. The shuttle will assist in anchoring the suture to the intra-arterial foot when the suture is pulled taught.

Figure 90:
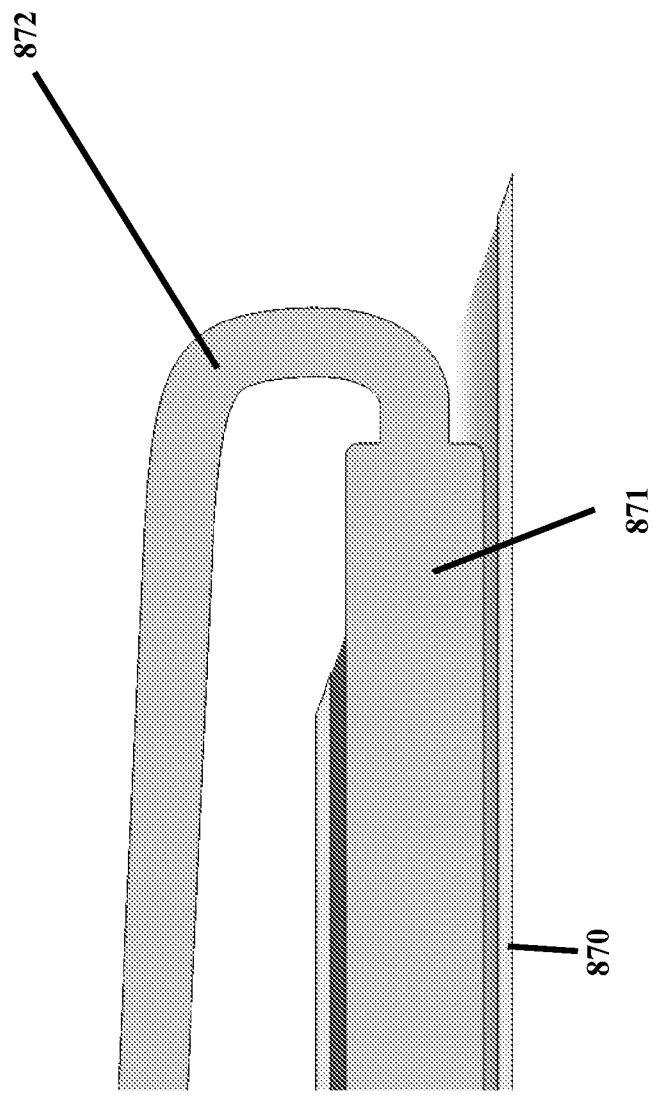
FIG. 90 illustrates a cross-sectional side view of the needle assembly of FIG. 87.

FIG. 90 illustrates a cross-sectional side view of the needle of FIG. 87. As indicated above and depicted in FIG. 90, the engagement of shuttle 871, which is attached to suture 872, with tubular needle 870, maintains the attachment of the suture to the needle and assures that the suture is pulled through any surfaces that the needle penetrates. The pointed edge of the tubular needle assist the needle in piercing an extra-arterial surface.

Figure 91:
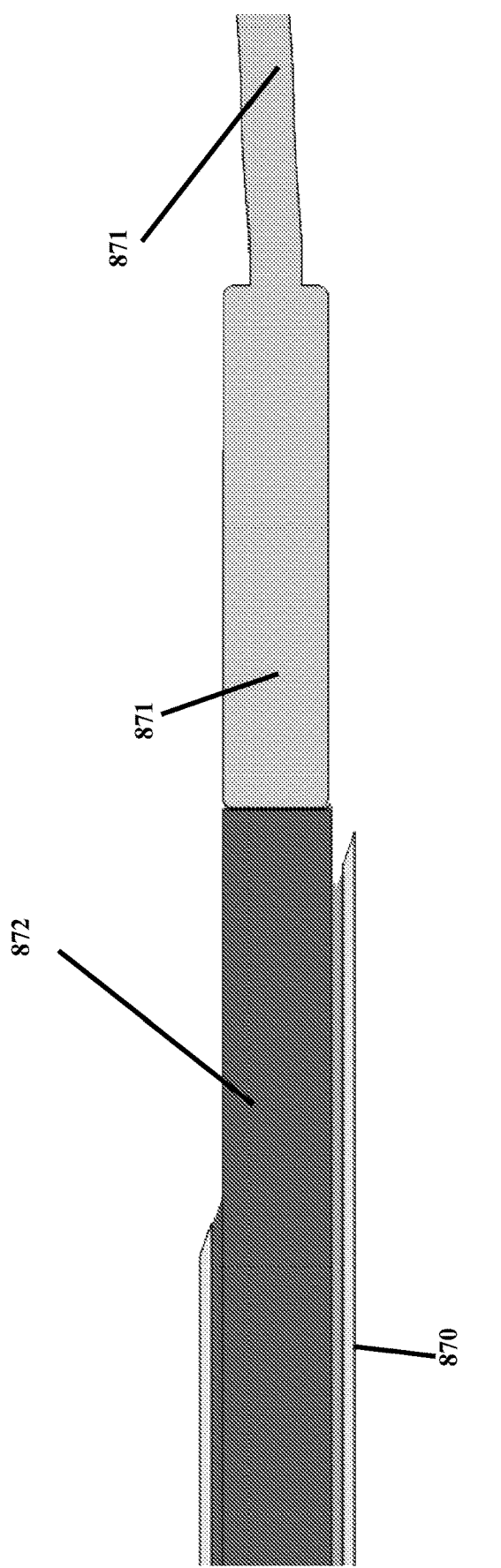
FIG. 91 illustrates a cross-sectional side view of the needle assembly of FIG. 87 ejecting a suture.

FIG. 91 illustrates a cross-sectional side view of the needle of FIG. 87 ejecting a suture. As shown the ejection of the suture is effected by the interaction of the pusher rod 880 with the shuttle 871 attached to suture 872.

Figure 92:
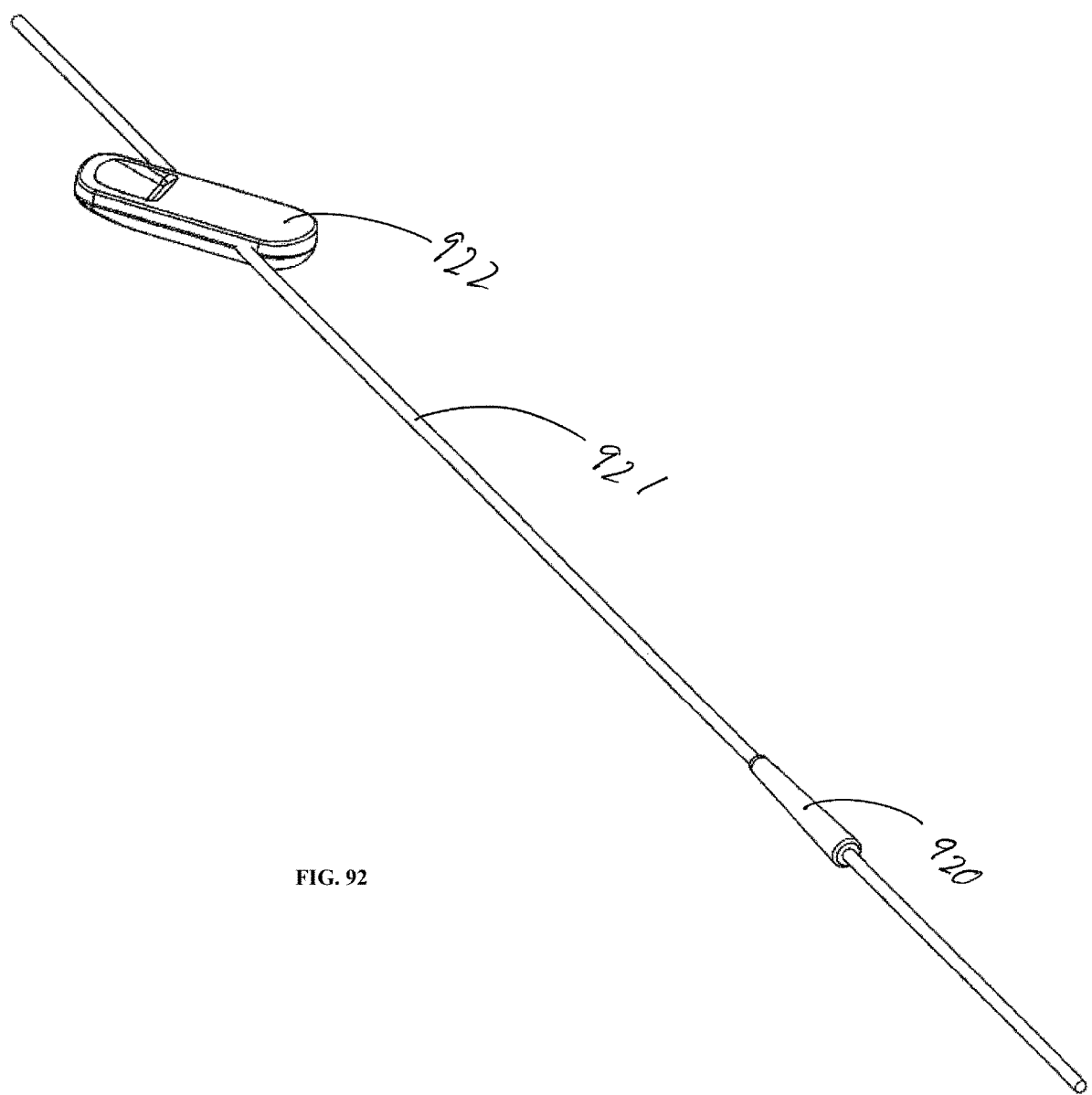
FIG. 92 illustrates an embodiment of a suture assembly in accordance with embodiments of the present invention.

FIG. 92 illustrates an embodiment of a suture assembly in accordance with embodiments of the present invention. The suture assembly depicted in FIG. 92 is engageable with various needle assembly embodiments Unlike the suture assembly depicted in FIGS. 3 and 4, the suture assembly depicted in FIG. 92 includes a shuttle that is co-axial with the extended suture 921. The assembly includes a bolster 922 positioned along the suture 921. Bolster 922, although generally stationary, may be movably attached to the suture in some embodiments so that when the shuttle and suture are inserted into a vessel and an intra-arterial foot via a needle and ejected from the needle, the bolster 922 may be adjusted to contact the exterior surface of the vessel and fixed on the suture at a location that maintains the suture taught and thereby holds the intra-arterial foot in place.

Figure 93:
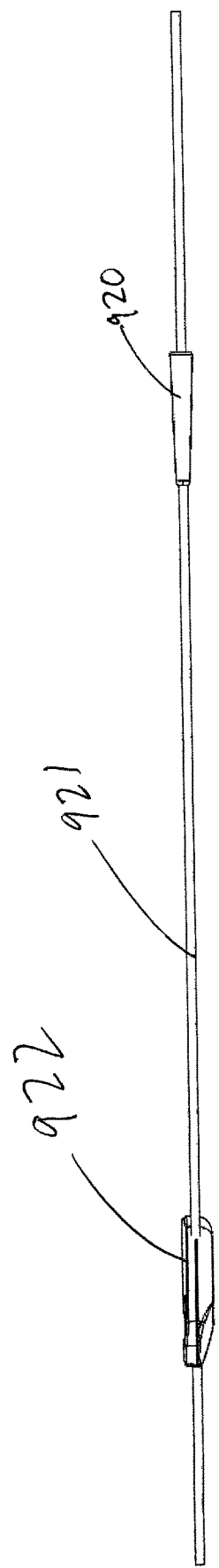
FIG. 93 illustrates a side view of the suture assembly of FIG. 92.
Figure 94:
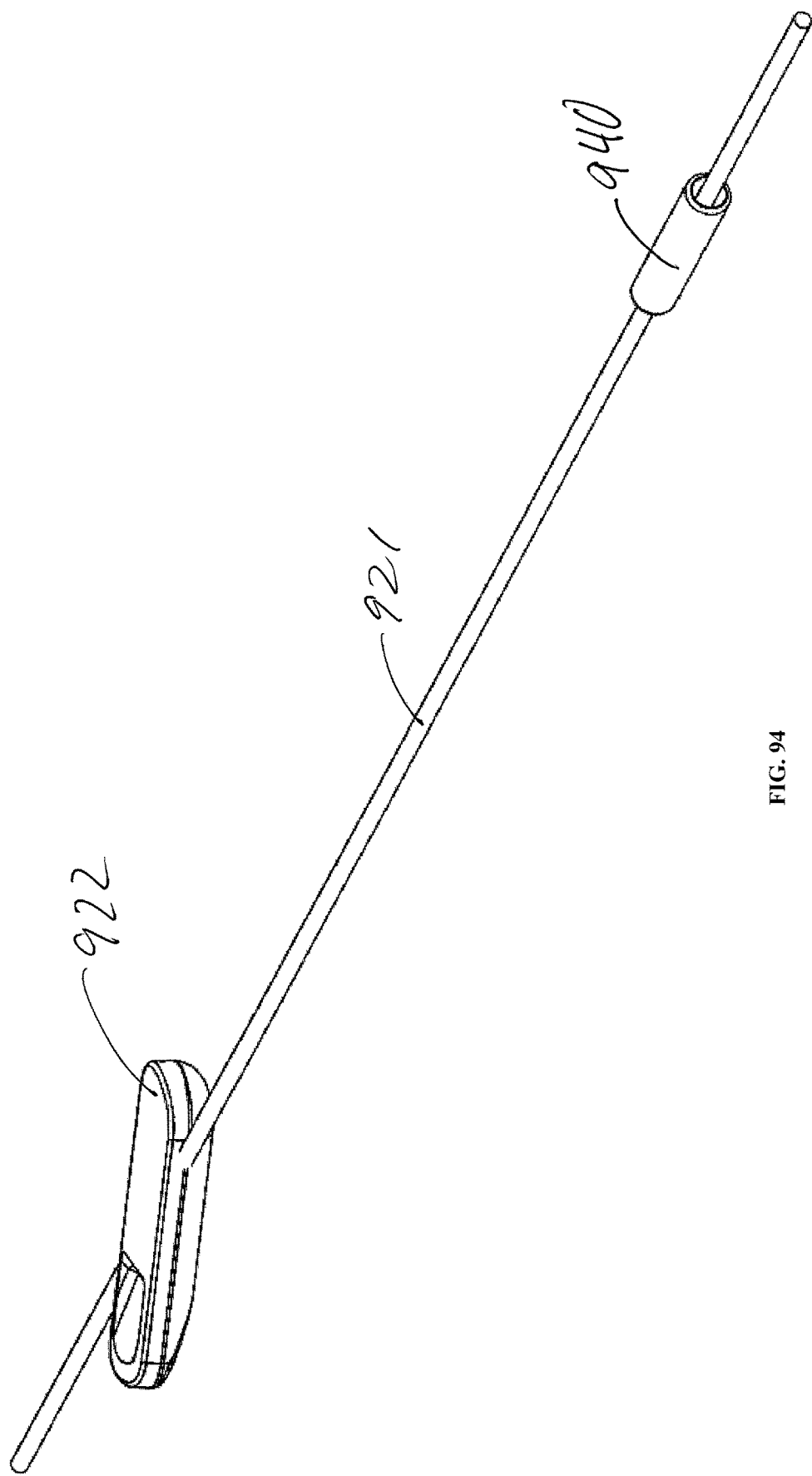
FIG. 94 illustrates the suture assembly of FIG. 92 with an alternative shuttle in accordance with embodiments of the present invention.
Figure 95:
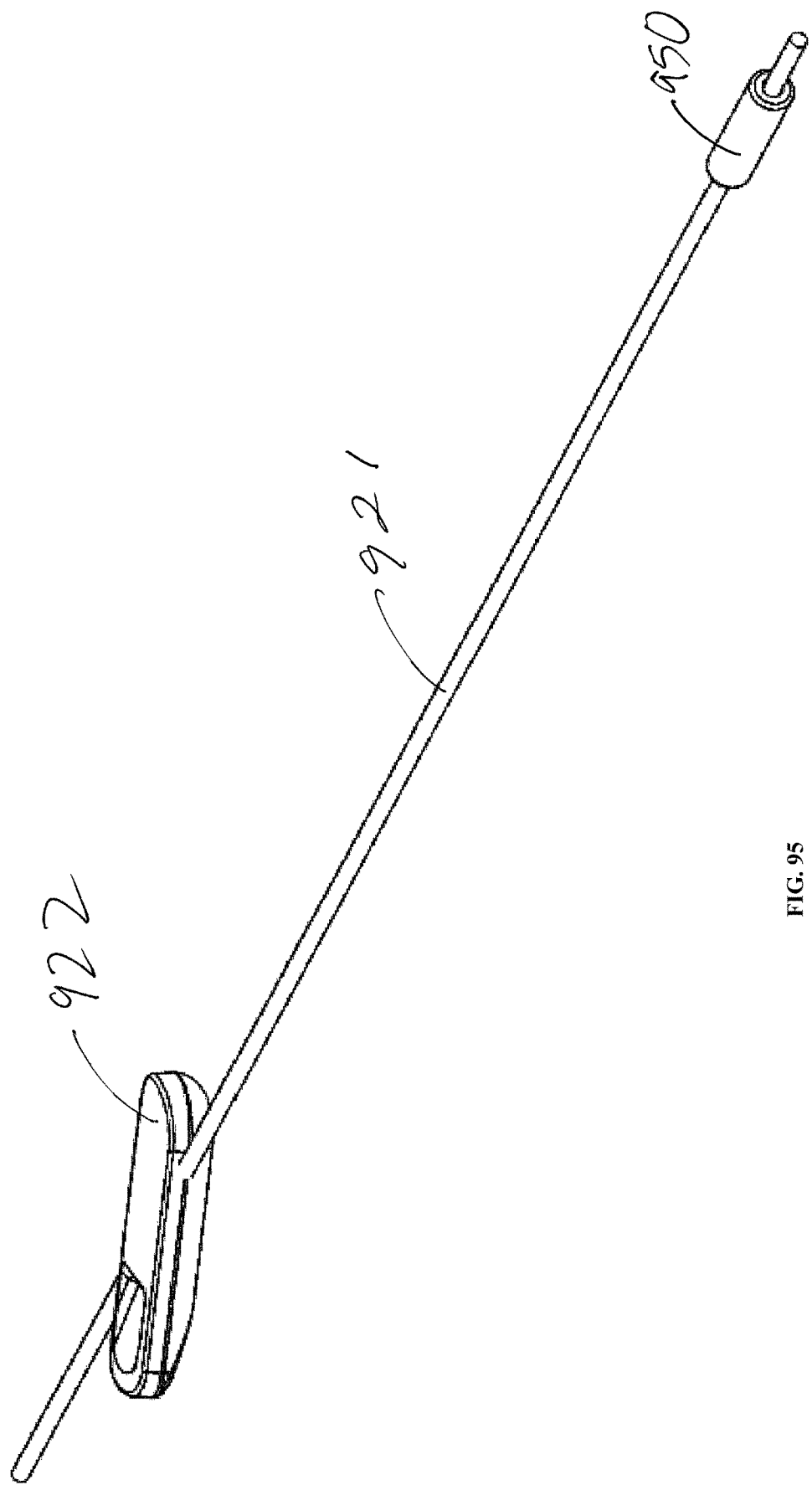
FIG. 95 illustrates the suture assembly of FIG. 92 with yet another alternative shuttle in accordance with embodiments of the present invention.

FIG. 93 illustrates a side view of the suture assembly of FIG. 92. As demonstrated the shuttle 920 is tapered in accordance with various embodiments of the present invention. However as demonstrated in FIGS. 94 and 95, the shuttle may take on other geometric shapes and properties. Specifically, the shuttle may have a uniform cross section, such as the tubular cross-section depicted by shuttle 940 of FIG. 94 and the cylindrical cross section depicted by shuttle 950 of FIG. 95. As further demonstrated by FIGS. 94 and 95, shuttles according to embodiments of the present invention may be hollow like shuttle 940 or may be solid like shuttle 950. A hollow shuttle or partially hollow, such as shuttle 940, allows the suture to be knotted and the knot may be maintained within the shuttle while keeping the suture affixed to the shuttle. The shuttle may be fixed to the suture through various means such as by knotting or tying of the suture, by bonding, using a glue/adhesive, by heat staking, by over-molding, or a combination of these processes. In some embodiments the shuttle may be movable, at least temporarily, along the suture.

Figure 96:
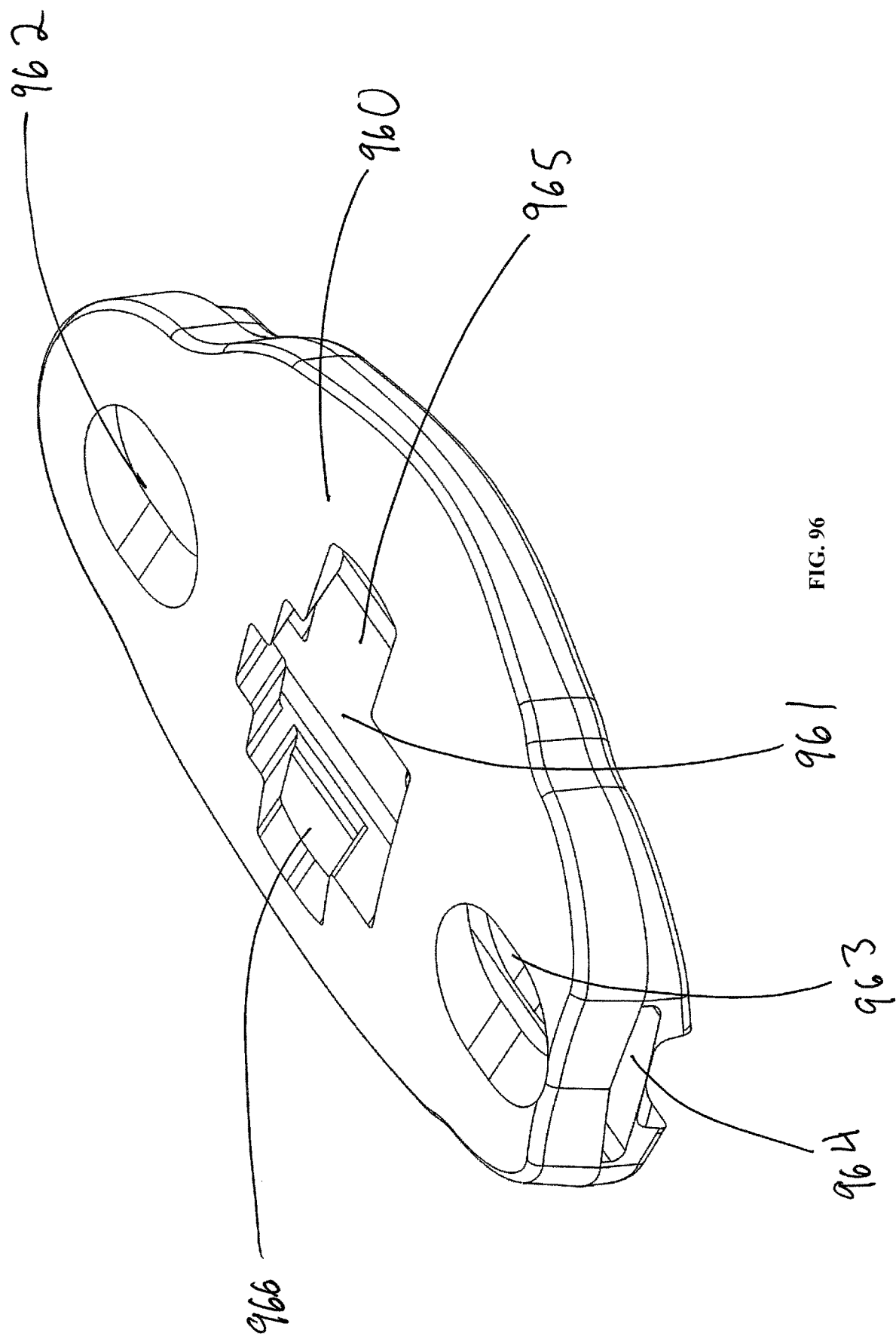
FIG. 96 depicts a perspective view of the central core of an intra-arterial foot in accordance with embodiments of the present invention.

FIG. 96 depicts a perspective view of the central core of an intra-arterial foot in accordance with embodiments of the present invention. Central core 960 may be coupled with a wing according to various embodiments of the present invention. Core 960 includes various apertures engageable for delivery of the core to a vessel and for coupling the core to a vessel via sutures. Core 960 has a central opening 961. Opening 961 does not extend through the bottom side of core 960. Opening 961 allows the foot to be anchored to an anchor assembly as will be further discussed. Opening 961 may be shaped to correspond to the base of an anchor such that the base of the anchor fits in core 960 in a lock and key configuration (i.e. the shape of the anchor base may correspond to at least a portion of the opening. Core 960 also includes openings 962 and 963, which receive the needle, suture, and shuttle provided by embodiments of the present invention. Each of openings 961-963 may be tapered or angled in accordance with various embodiments of the present invention. The angular aspect of opening 961 allows core 960 to be maintained at a particular orientation on the base of an anchor. Core 960 also includes a channel 964 extending through the core.

Figure 97:
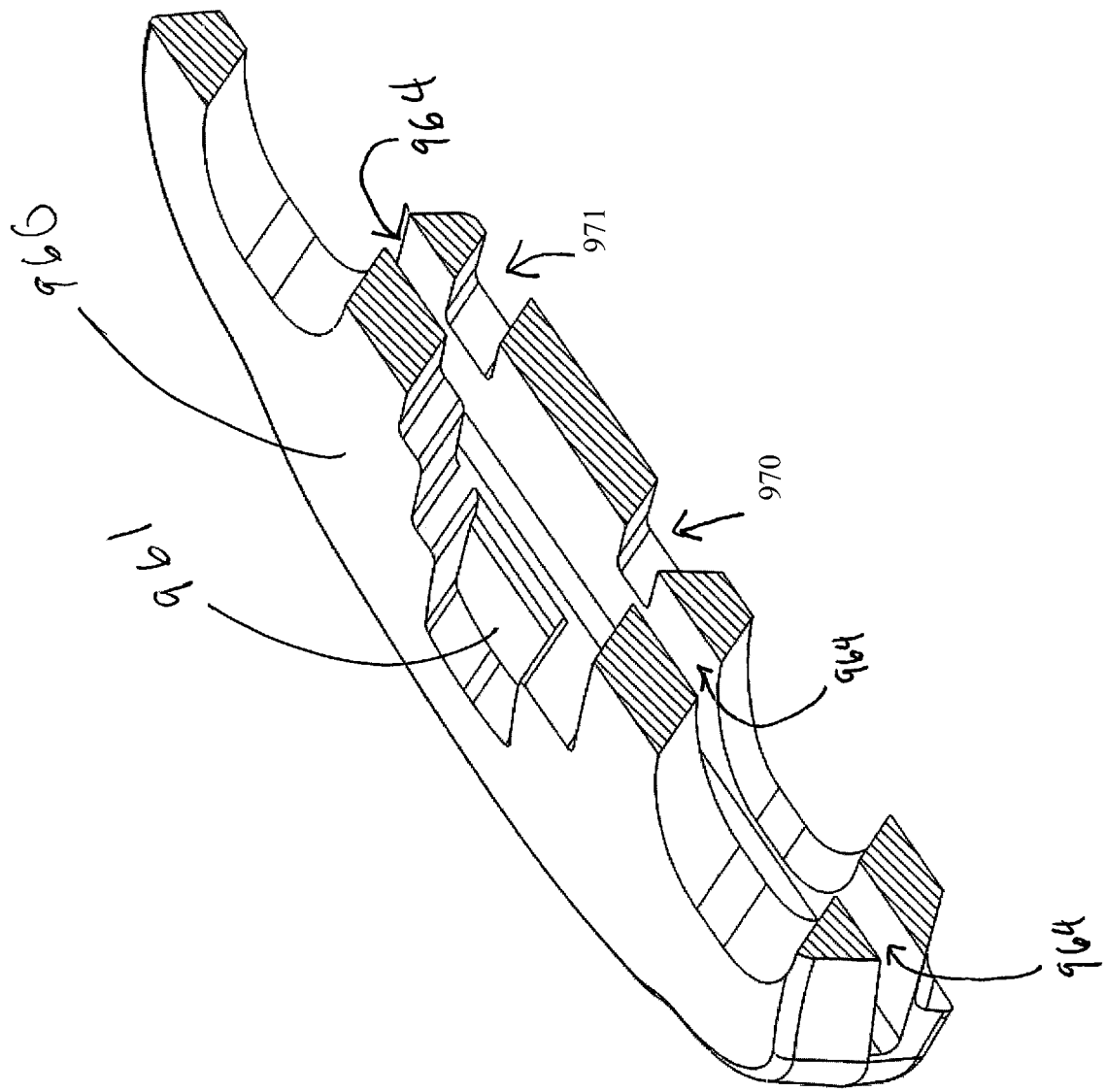
FIG. 97 shows a cross-sectional view of the central core depicted in FIG. 96.

FIG. 97 shows a cross-sectional view of the central core depicted in FIG. 96. As shown in FIG. 97 channel 964 may extend an entire span of core 960. As further demonstrated in FIG. 96, core 960 may include openings 970 and 971, which may be aligned with parts of opening 961.

Figure 98:
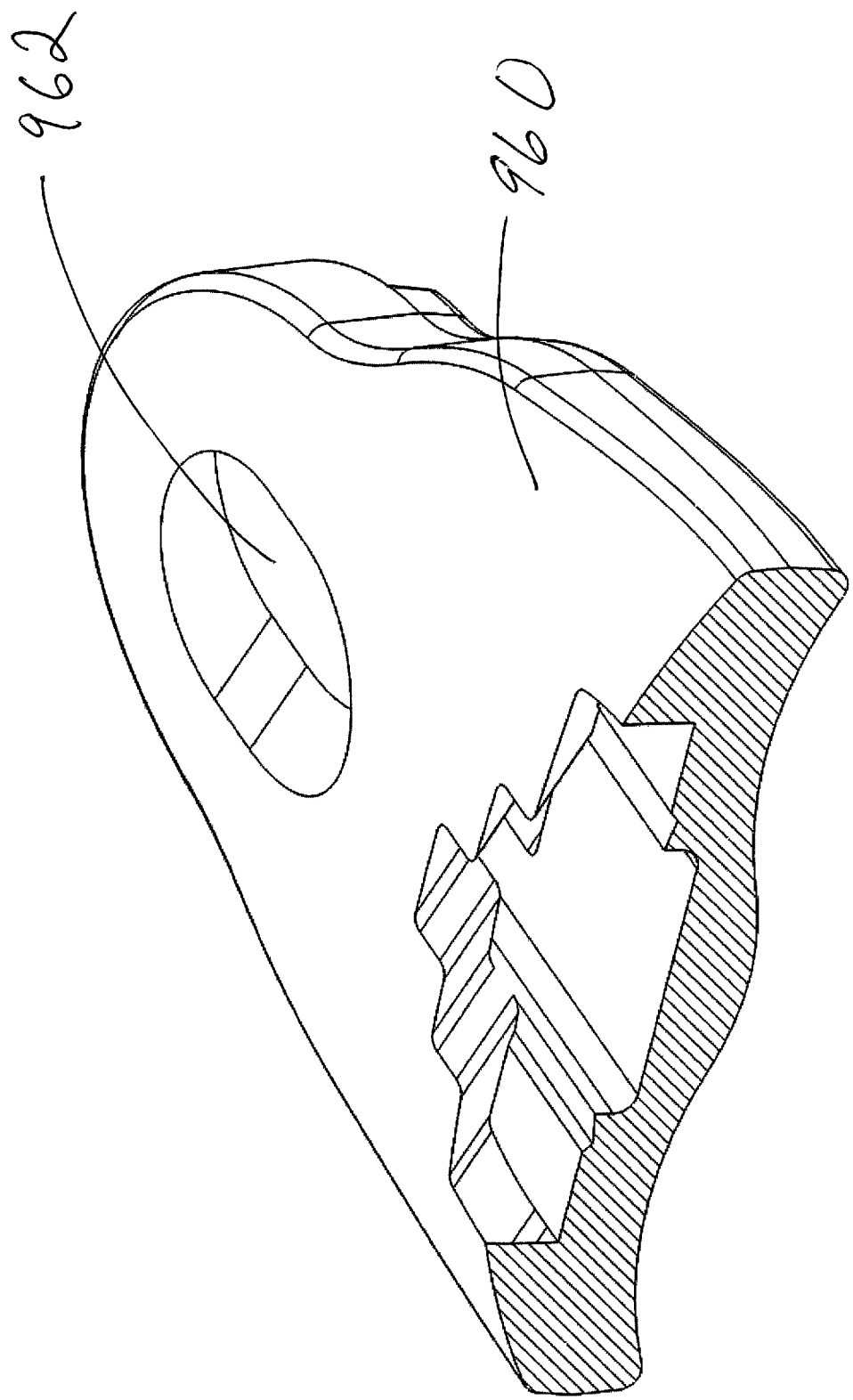
FIG. 98 shows another cross-sectional view of the central core depicted in FIG. 96.

FIG. 98 shows another cross-sectional view of the central core depicted in FIG. 96. As shown in FIG. 98, the region on core 960 directly below the center of opening 961 is solid such that a portion of the opening does not penetrate the entire depth of core 960.

Figure 99:
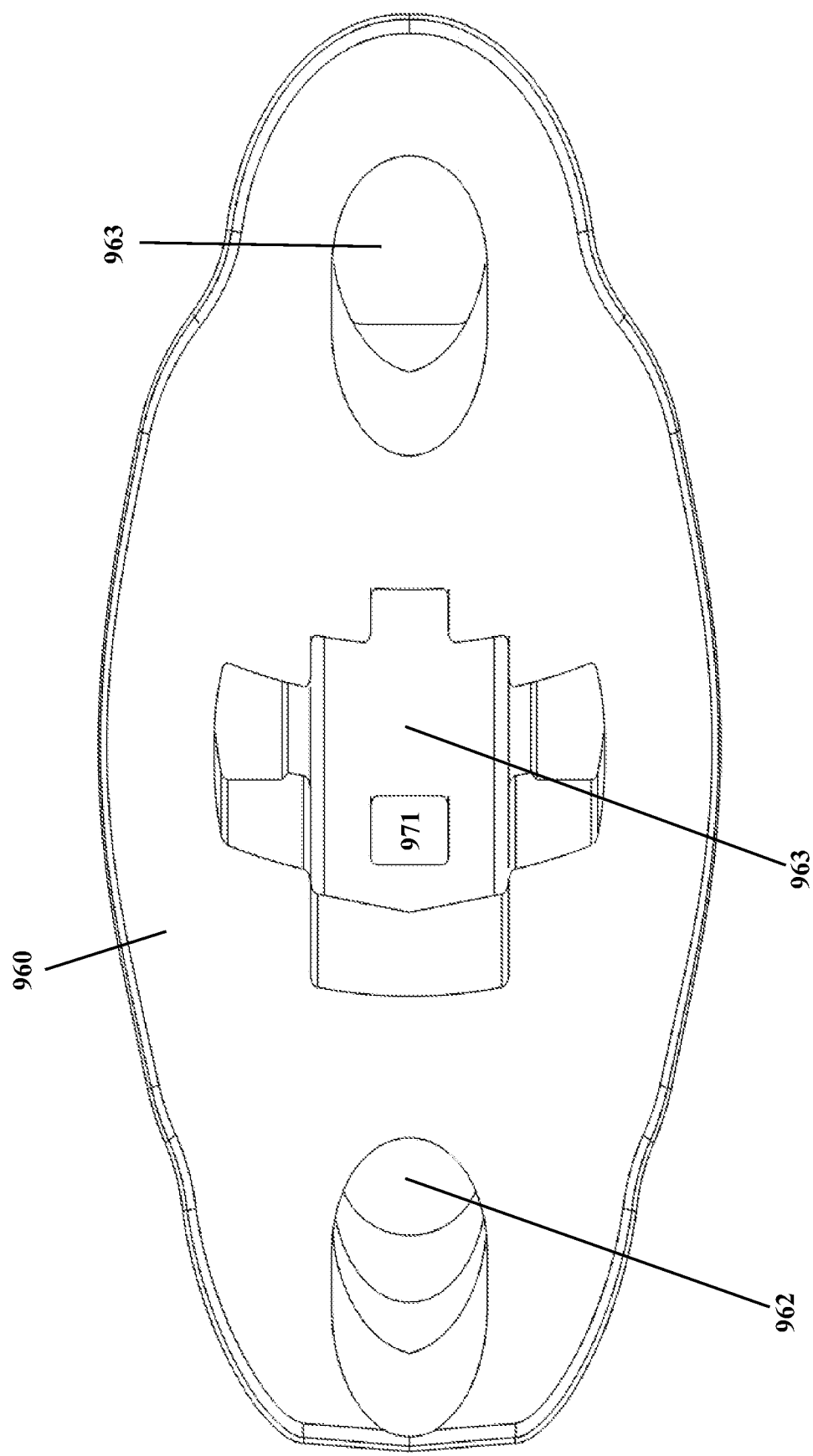
FIG. 99 illustrates a top view of the central core depicted in FIG. 96.

FIG. 99 illustrates a top view of the central core depicted in FIG. 96. While a central region of opening 961 may not penetrate the entire depth of core 960, other opening such as opening 971 may provide a channel aligned with opening 961 such that the channel penetrates the entire depth of core 960. FIG. 99 further demonstrates an exemplary shape of core 960 in accordance with various embodiments of the present invention.

Figure 100:
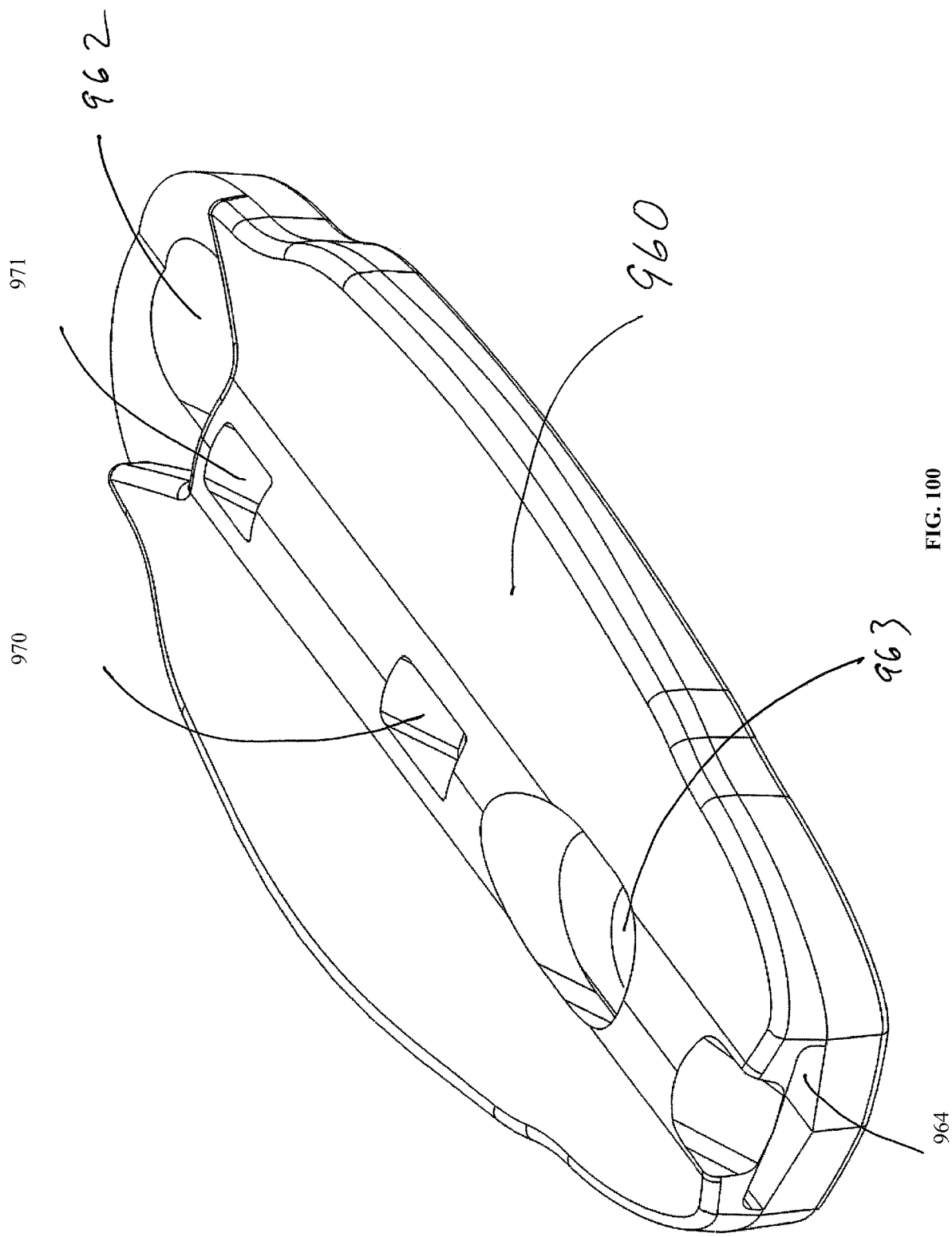
FIG. 100 illustrates a bottom perspective view of the central core depicted in FIG. 96.

FIG. 100 illustrates a bottom perspective view of the central core depicted in FIG. 96. FIG. 100 shows openings 962 and 963 as penetrating the entire depth of core 960. As described above, these openings receive the shuttle portion of suture assemblies via the insertion of needles into the openings.

Figure 101:
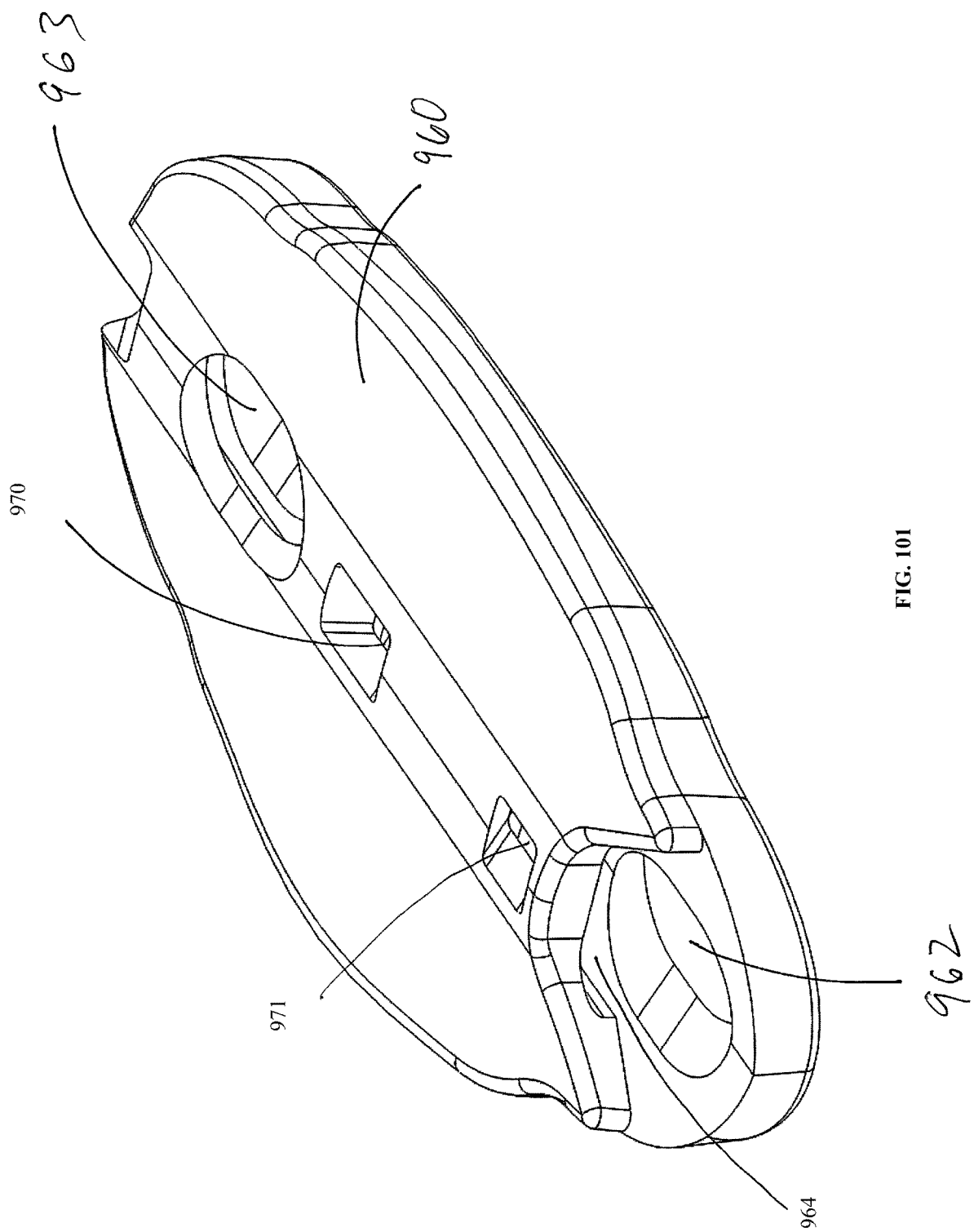
FIG. 101 provides a view of FIG. 100 from the opposite end of the central core.

FIG. 101 provides a view of FIG. 100 from the opposite end of the central core. Channel 964 shown on one side of core 960 in FIG. 100 is shown to extend to the other side of core 960 in FIG. 101.

Figure 102:
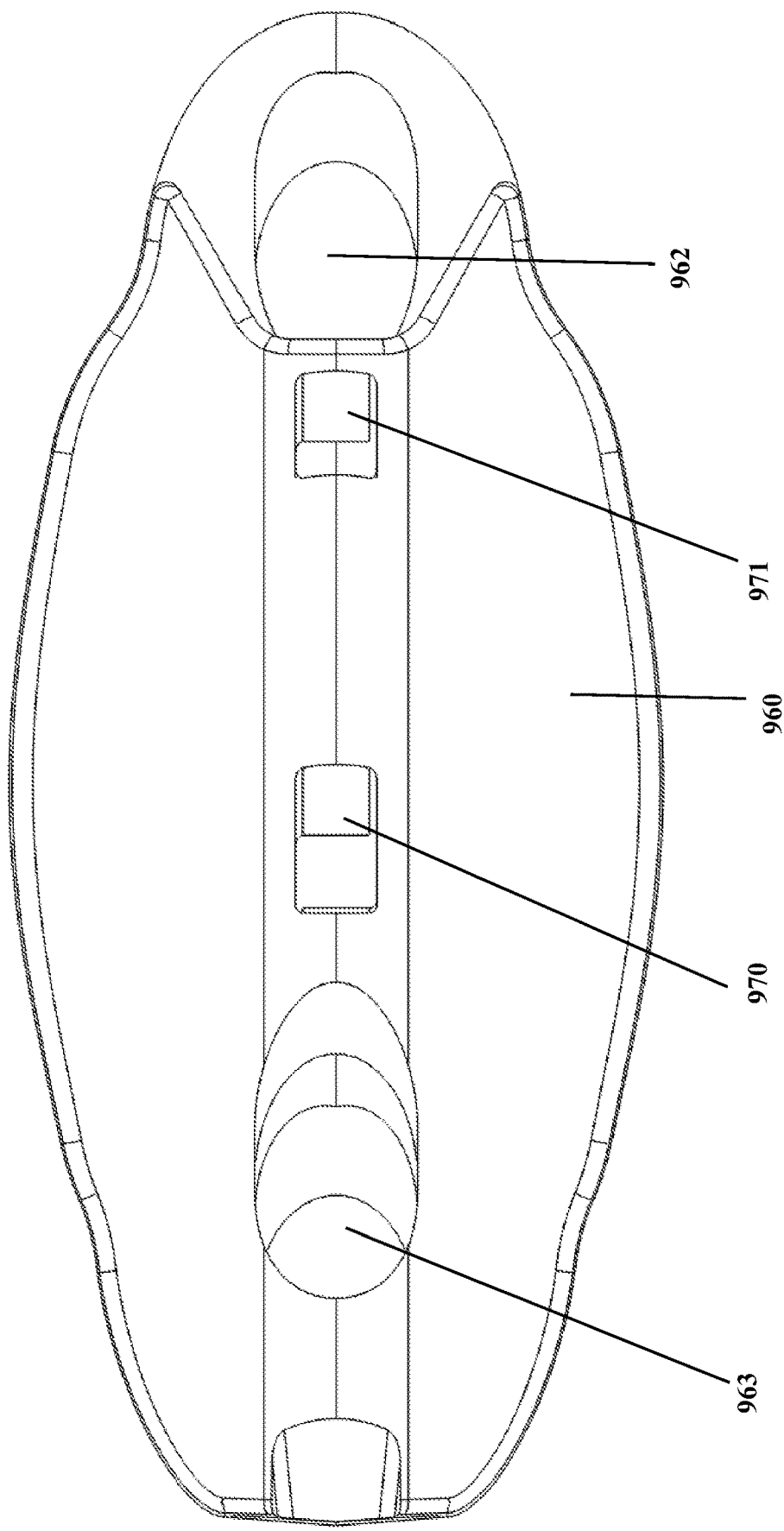
FIG. 102 shows a bottom the central core of FIG. 96.

FIG. 102 shows a bottom view the central core of FIG. 96. The perimeter of the core 960 is illustrated as having a distinct geometry on the bottom of core 960 that differs from the geometry on the top of core 960.

Figure 103:
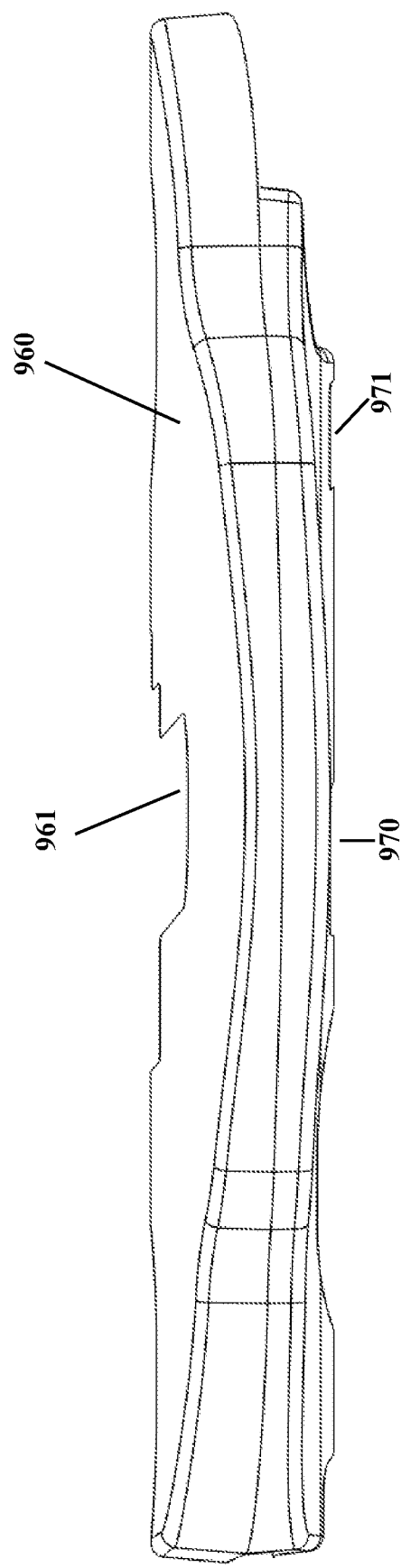
FIG. 103 shows a side view of the central core of FIG. 96.

FIG. 103 shows a side view of the central core of FIG. 96. The top surface of core 960 may not be planar as demonstrated in FIG. 103. Additionally, the entry/exit point of openings 970 and 971 may be offset from opening 961 such that a channel extending from one of openings 971 or 970 to opening 961 is angular with respect to core 960.

Figure 104:
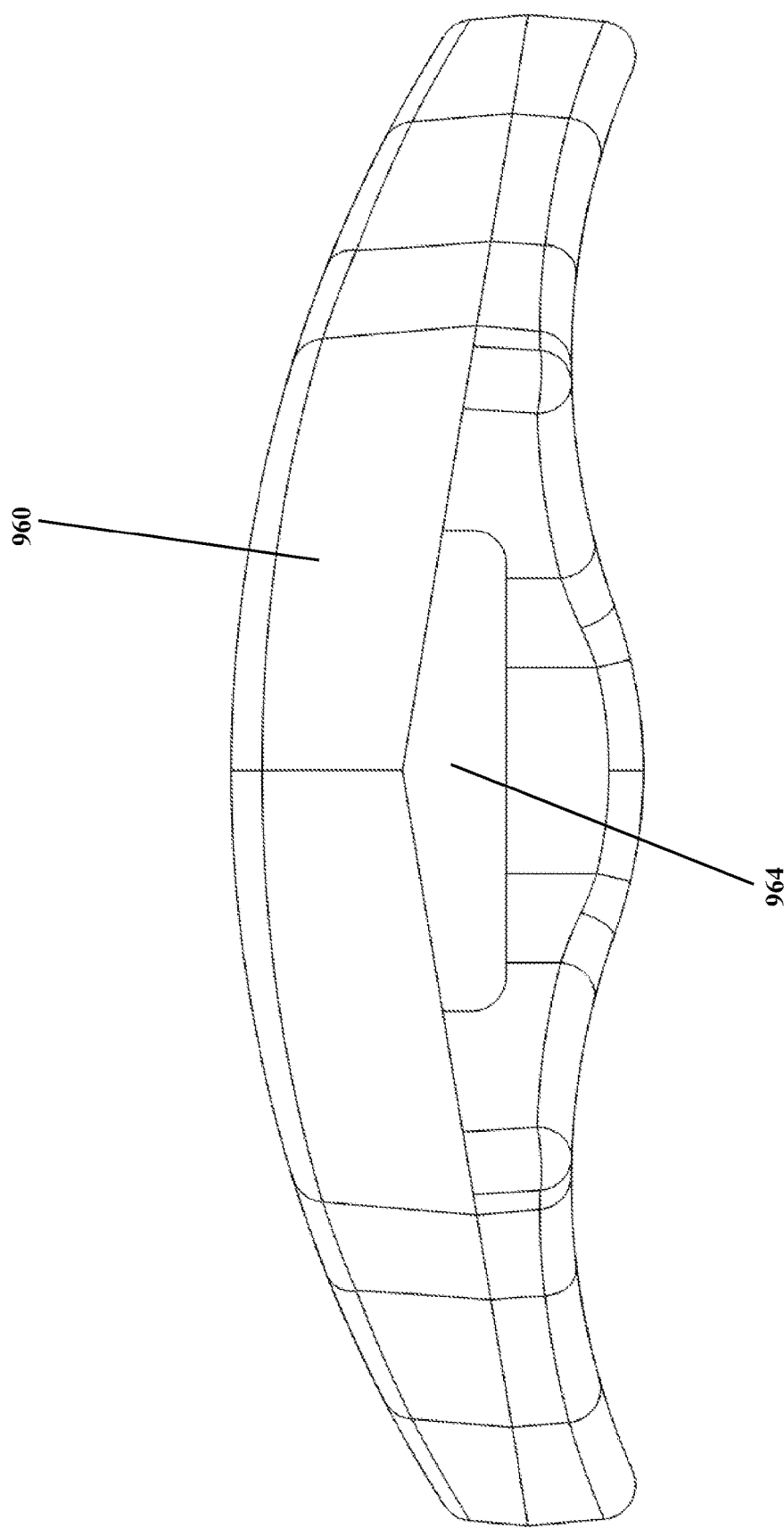
FIGS. 104 and 105 illustrate end views the central core of FIG. 96.
Figure 105:
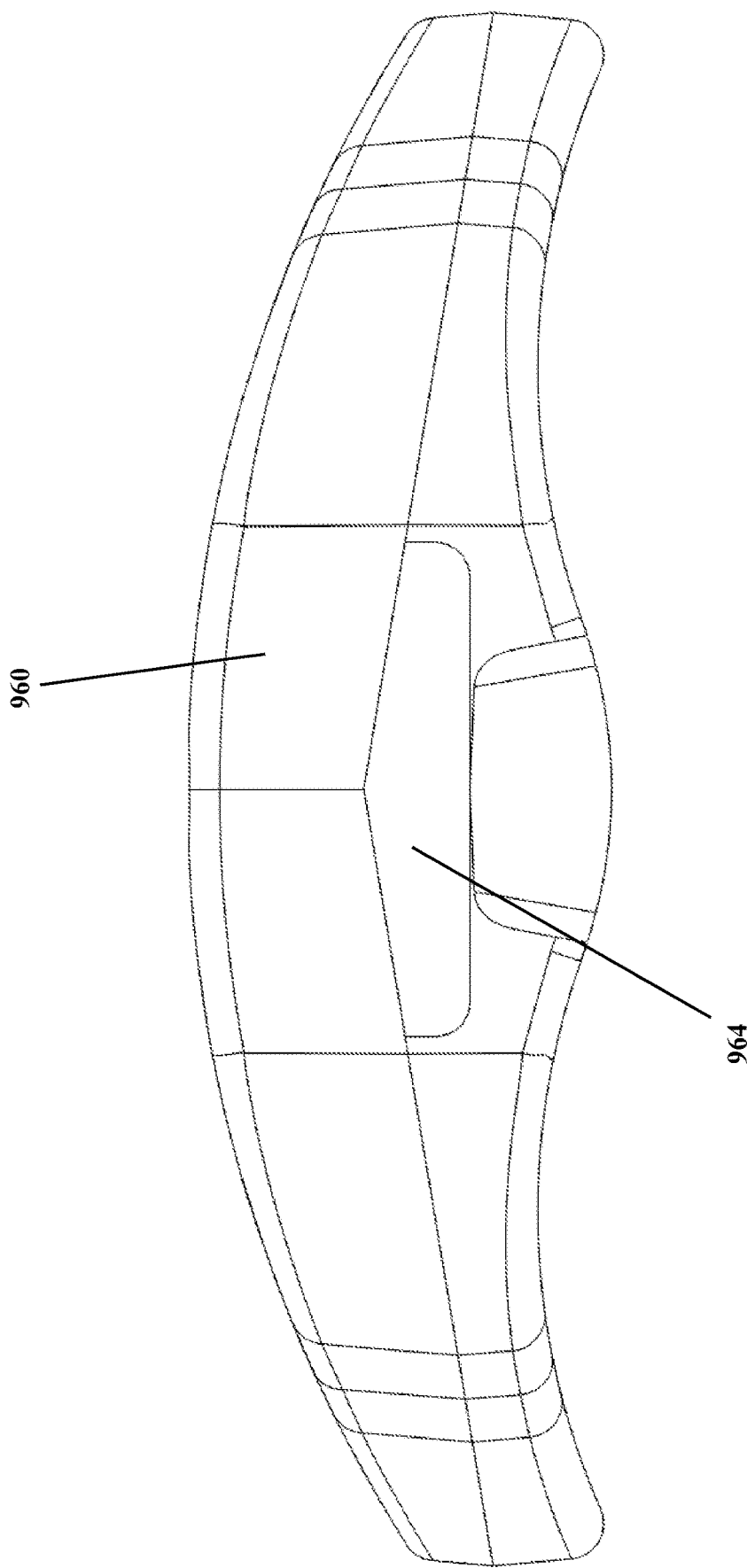

FIGS. 104 and 105 illustrate end views the central core of FIG. 96 with channel 964 extending from one end to the other end. As discussed with previous embodiments, in some embodiments the core may have an arcuate upper surface to conform to an intra-arterial surface.

Figure 106:
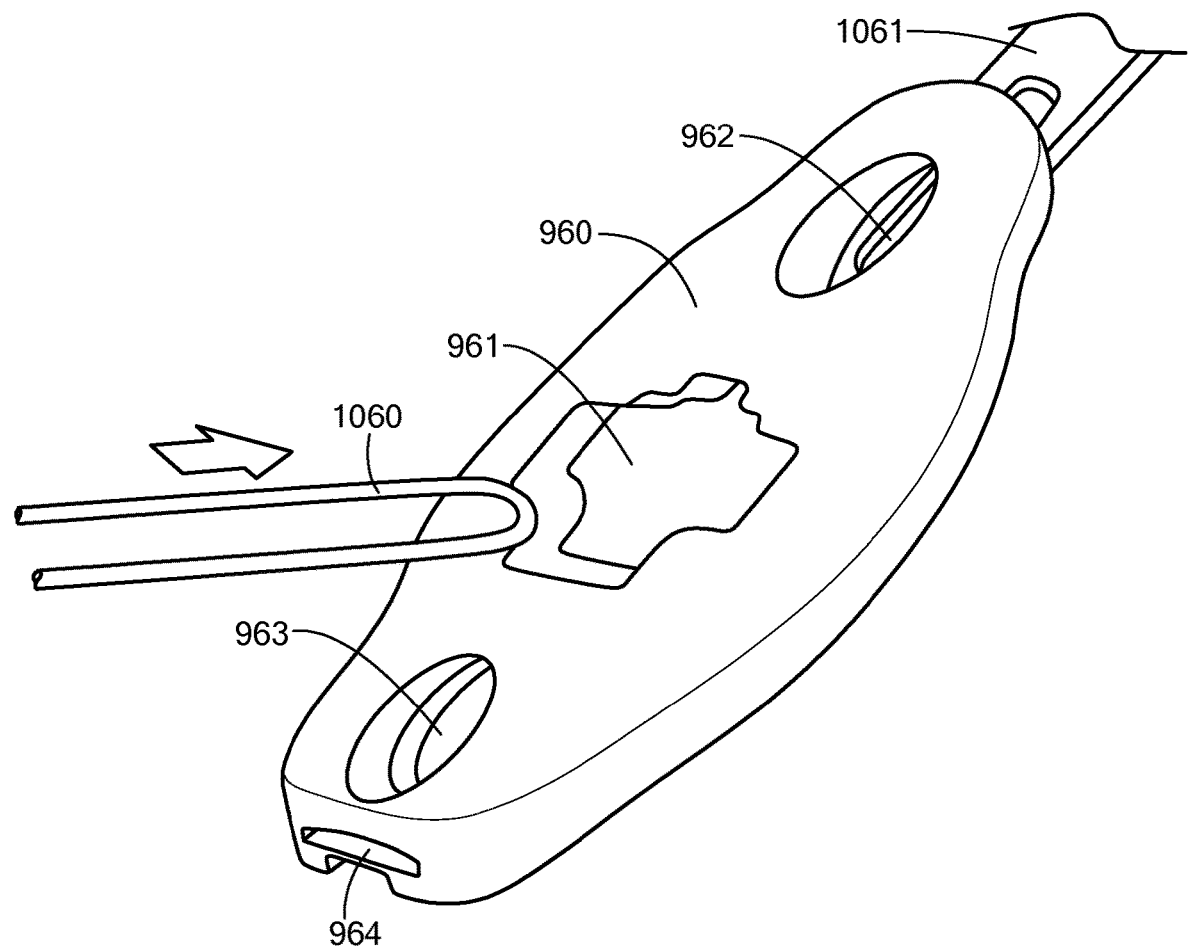
FIG. 106 illustrates a central core prior to insertion of a ribbon wire engageable with a ribbon in accordance with embodiments of the present invention.

FIG. 106 illustrates a central core prior to insertion of a ribbon wire engageable with a ribbon in accordance with embodiments of the present invention. In accordance with some embodiments of the present invention, a single ribbon 1061 may be engaged with a central core 960 of an intra-arterial foot. The ribbon, which may be used to affix one or more sutures to central core 960 in a prescribed manner, such as the manner illustrated by sutures 104 in FIG. 1, is engageable with ribbon wire 1060. Engaging ribbon wire 1060 with ribbon 1061 requires inserting ribbon wire 1060 into opening 961 before inserting ribbon 1060 completely in channel 964.

Figure 107:
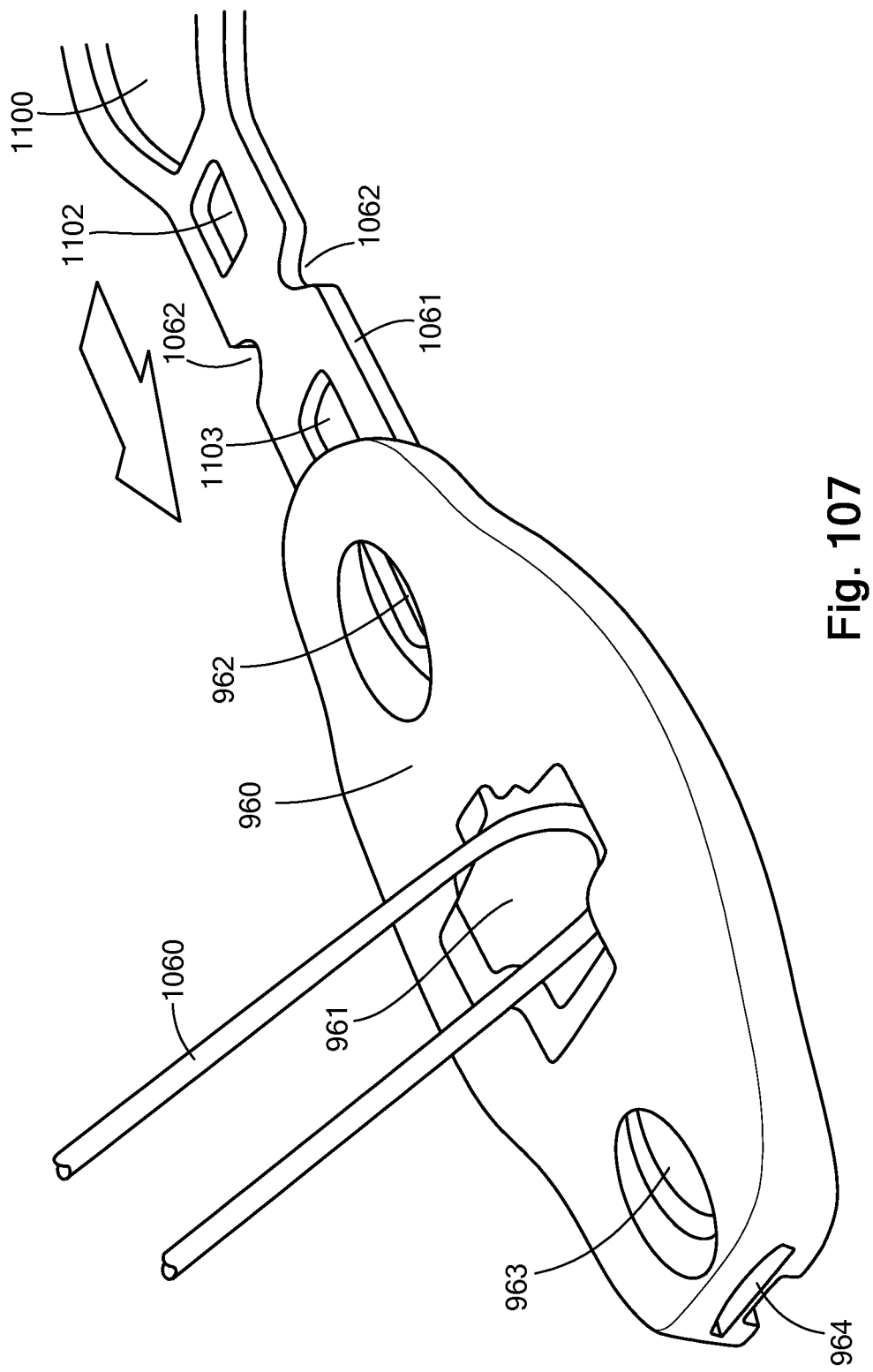
FIG. 107 illustrates the central core of FIG. 106 after insertion of the ribbon wire.

FIG. 107 illustrates the central core of FIG. 106 after insertion of the ribbon wire into opening 961 in preparation to receive ribbon 1061 through the loop formed by wire 1060. Ribbon 1060 includes grooves 1062 configured to engage and maintain engagement with ribbon wire 1060.

Figure 108:
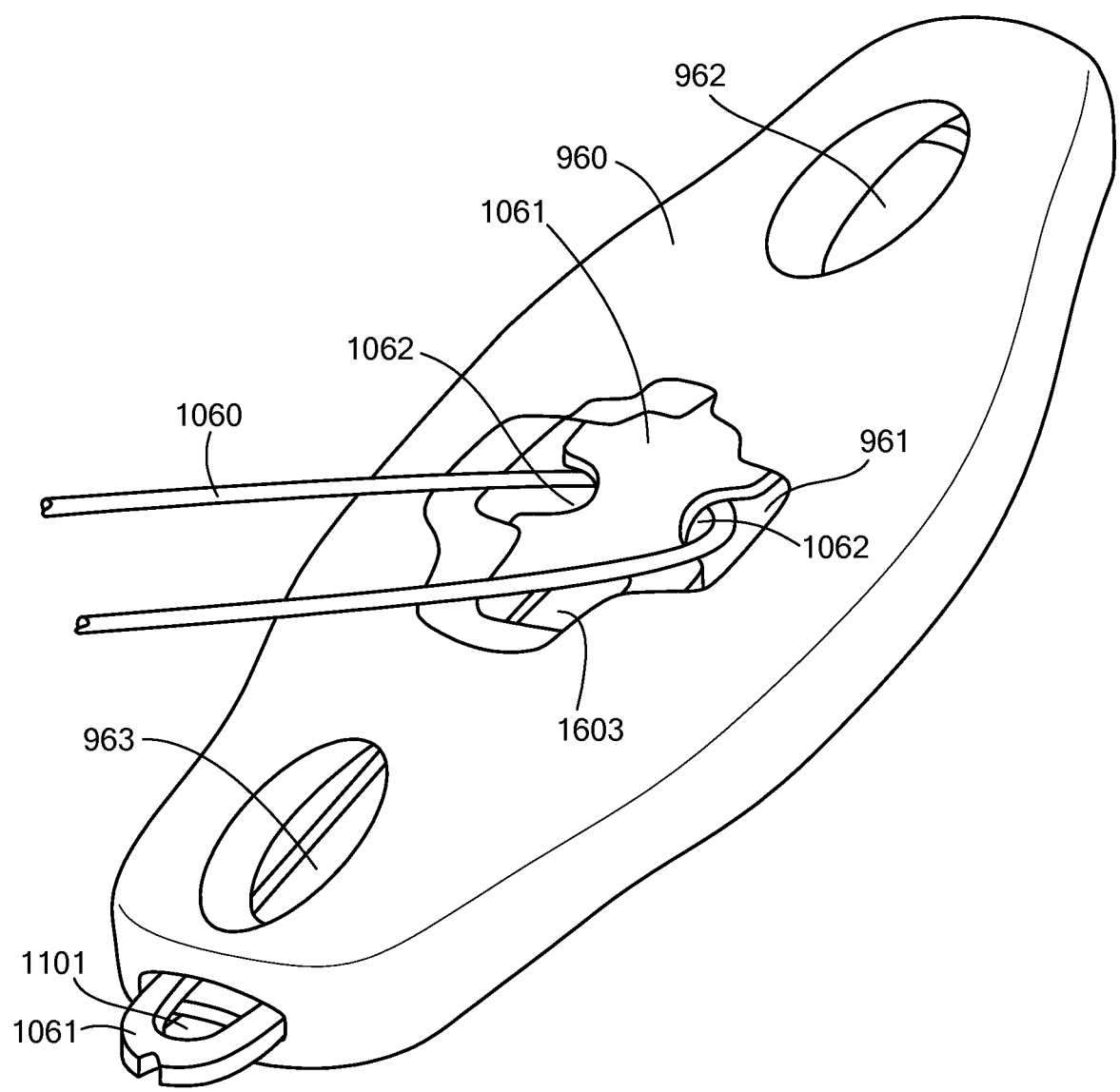
FIG. 108 illustrates the central core of FIG. 106 after the ribbon wire engages the ribbon inserted into the central core.

FIG. 108 illustrates the central core of FIG. 106 after the ribbon wire engages the ribbon inserted into the central core. As shown in FIG. 106 wire 1060 engages grooves 1062 of ribbon 1061 according to various embodiments of the present invention. Additionally openings 963 and 962 are aligned with openings 1101 and 1100 of ribbon 1060. The alignment of the openings on ribbon 1060 and core 960 allows penetration of needle assemblies and suture assemblies according to various embodiments of the present invention.

Figure 109:
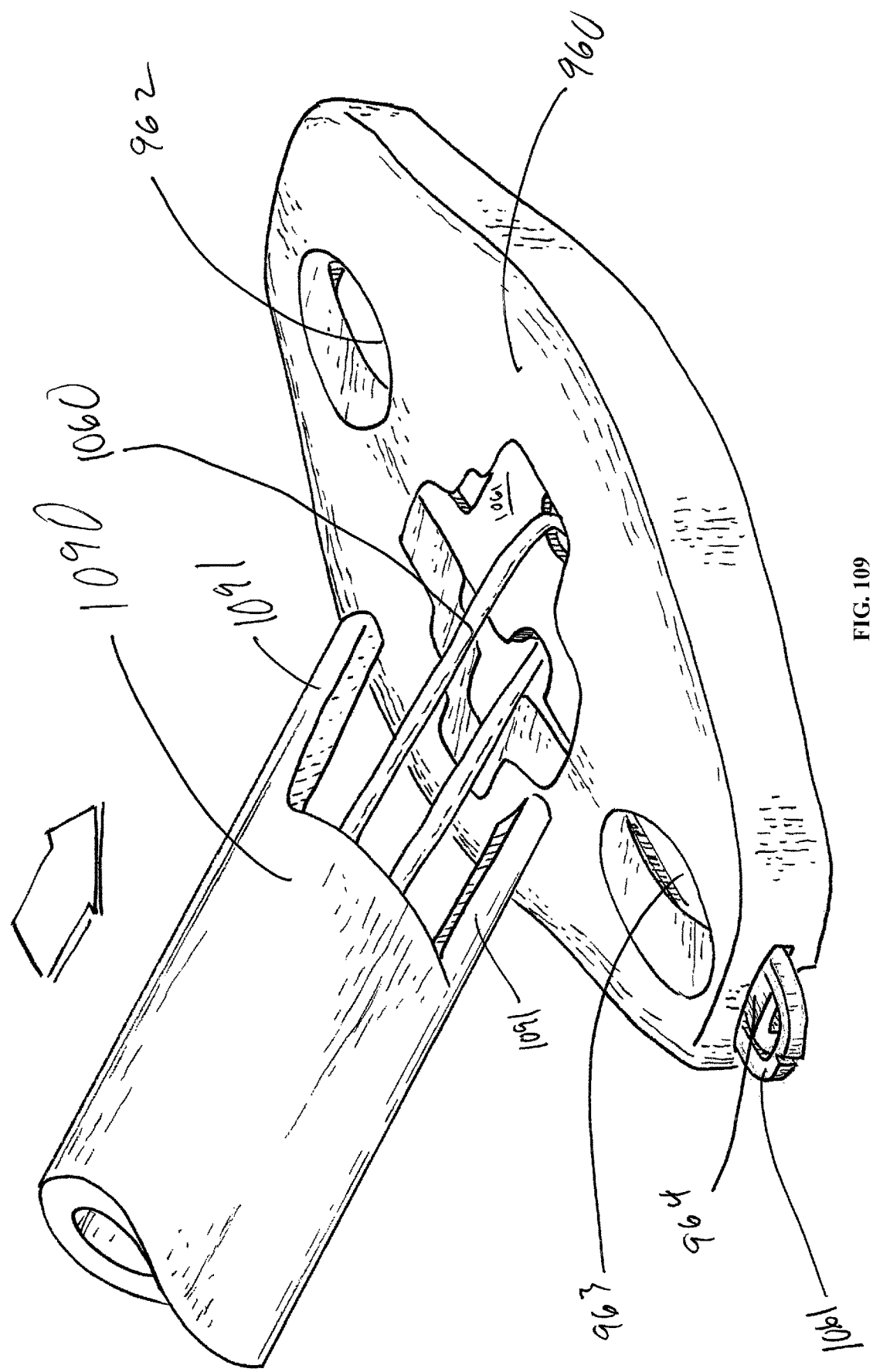
FIG. 109 illustrates the central core of FIG. 106 prior to insertion of an anchor assembly.

FIG. 109 illustrates' the central core of FIG. 106 prior to insertion of an anchor assembly. The anchor assembly 1090 may be moved axially, the assembly travelling parallel to the ribbon wire. Anchor assembly may include prongs 1091 geometrically shaped to fit in a keyed portion of opening 961.

Figure 110:
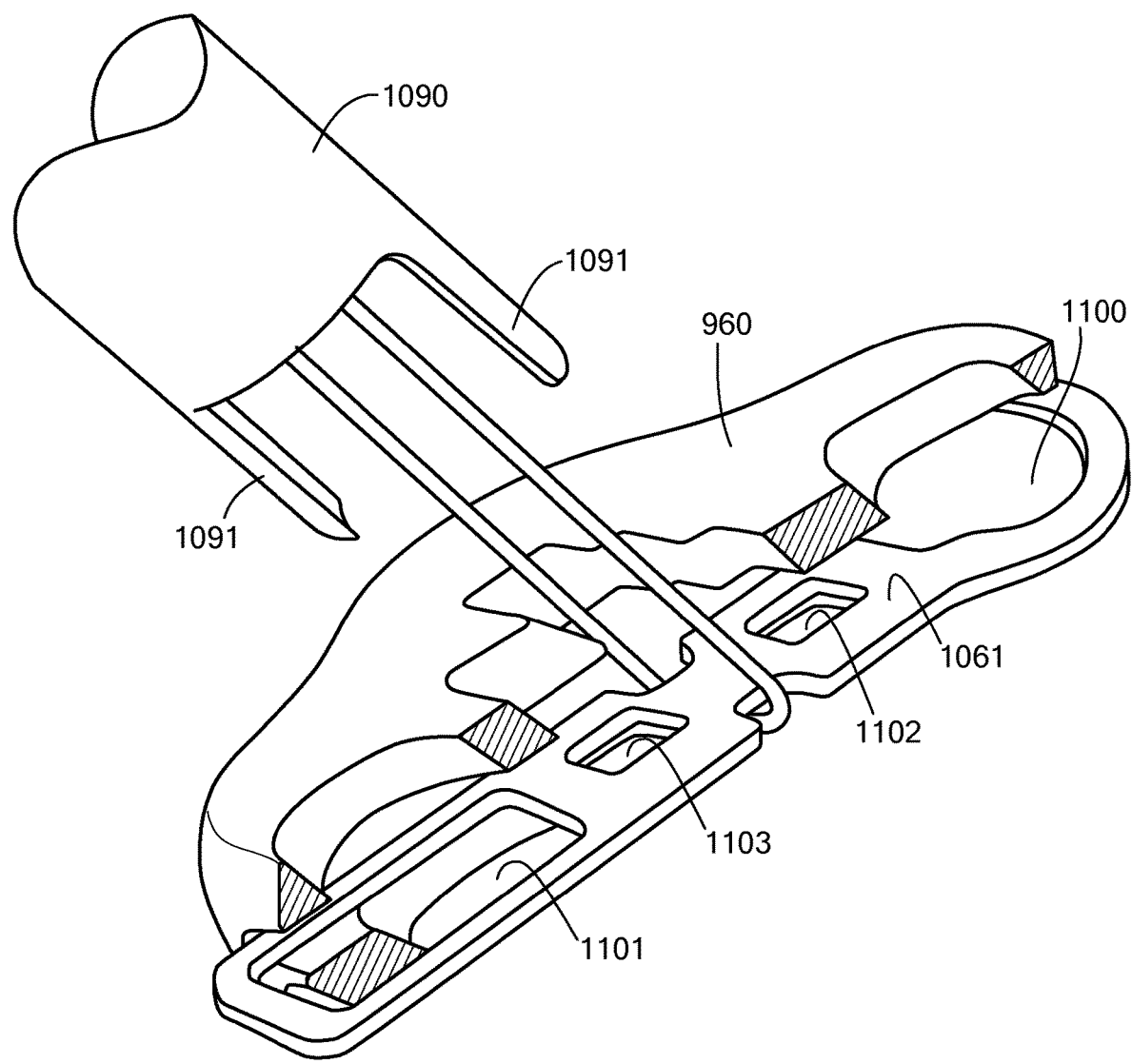
FIG. 110 shows a cross-sectional view of FIG. 109.

FIG. 110 shows a cross-sectional view of FIG. 109. As shown in FIG. 109, ribbon 1061 may include a plurality of apertures, engageable with various components of the delivery device and securing members, such as the suture assemblies. Openings 1100 and 1101 are aligned with openings 962 and 963 in core 960.

Figure 111:
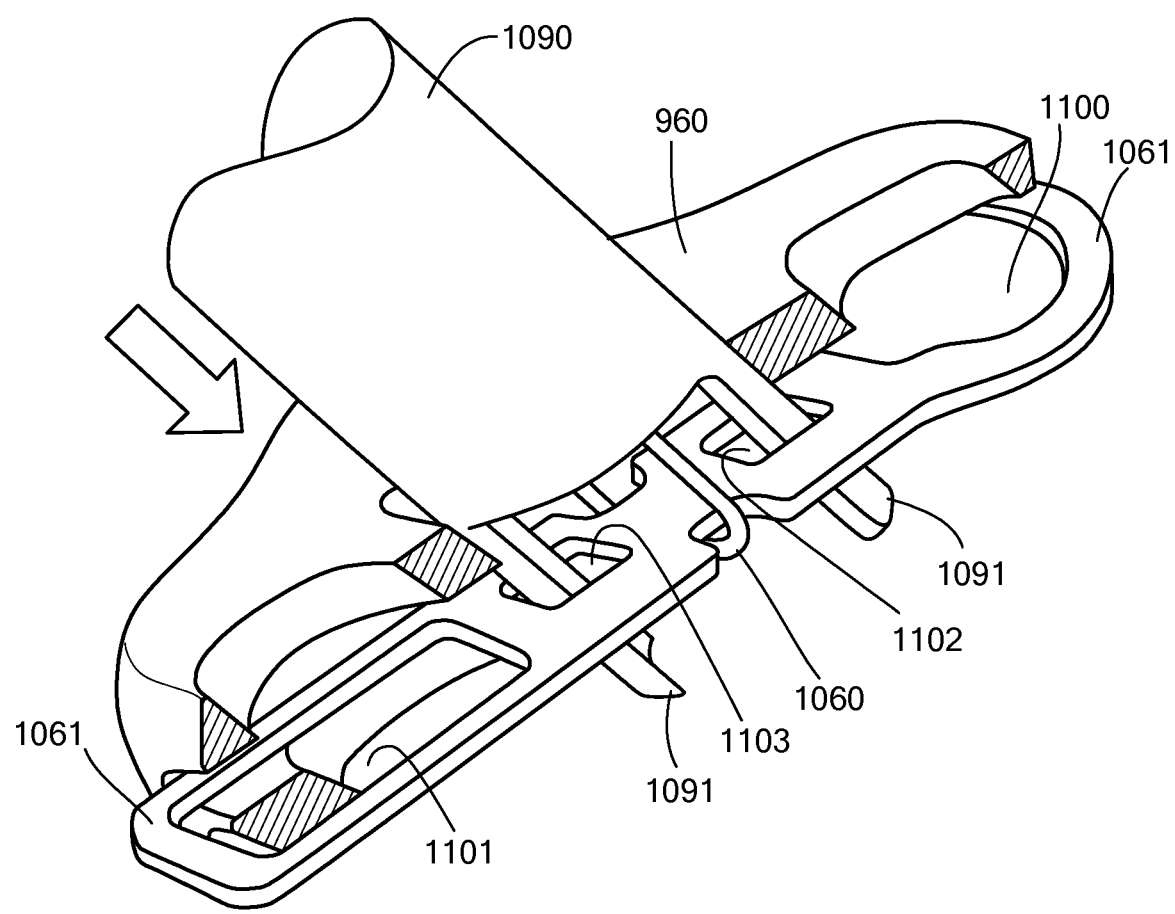
FIG. 111 illustrates a cross-sectional view of the central core shown in FIG. 106 with the ribbon inserted into the core and with the ribbon wire and anchor engaging the ribbon wire.

FIG. 111 illustrates a cross-sectional view of the central core shown in FIG. 106 with the ribbon inserted into the core and with the ribbon wire and anchor engaging the ribbon wire. The prongs of the anchor assembly 1091 traverse openings 1102 and 1103 of ribbon 1061 as well as openings 970 and 971 in core 960, thereby helping to maintain the core of the intra-arterial foot anchored to the anchor assembly for movably deploying the foot from a sheath through an arteriotomy and into the interior of an artery or vessel.

Figure 112:
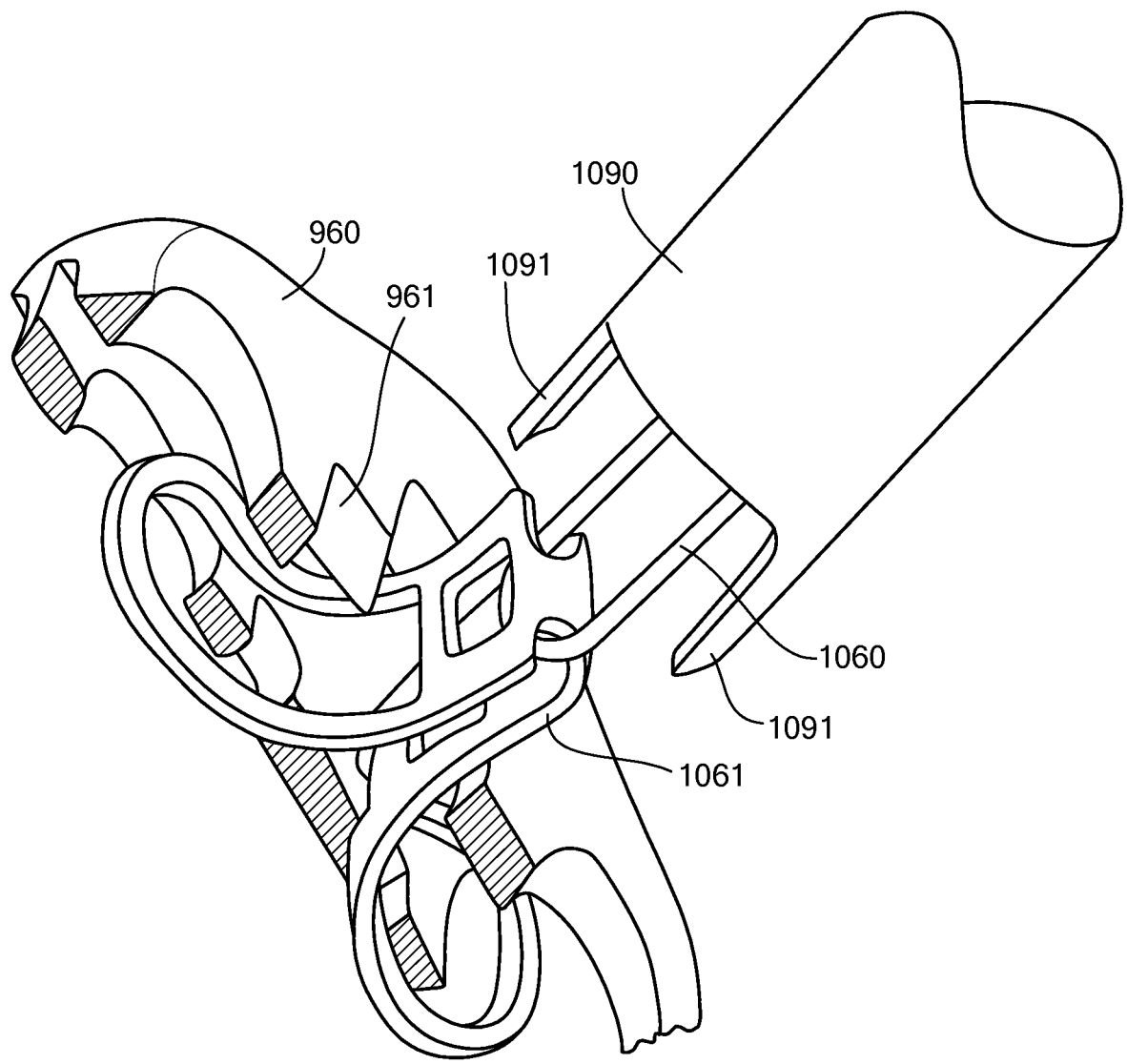
FIG. 112 illustrates a cross-sectional view of the central core shown in FIG. 106 during removal of a ribbon from the central core via the ribbon wire.

FIG. 112 illustrates a cross-sectional view of the central core shown in FIG. 106 during removal of a ribbon from the central core via the ribbon wire. In the context of an operation, once sutures are deployed and extend through apertures 1101 and 1100 of ribbon 1061 and apertures 963 and 962 of core 960 and core 960 is positioned as desired, anchor assembly 1090 and ribbon wire 1060 may be retracted. The retraction of these components may occur independently of one another. The retraction of ribbon wire 1060 will cause ribbon 1061 to be drawn out of core 960 through central opening 961. As shown in FIG. 112, ribbon 1061 may be made sufficiently flexible, via material and/or geometric properties, to achieve such a withdrawal. As apertures 1101 and 1100 are withdrawn from core 960 they will pull any suture extending there through towards the center of the core 960, whereby the sutures may become affixed within channel 964 of core 960.

Figure 113:
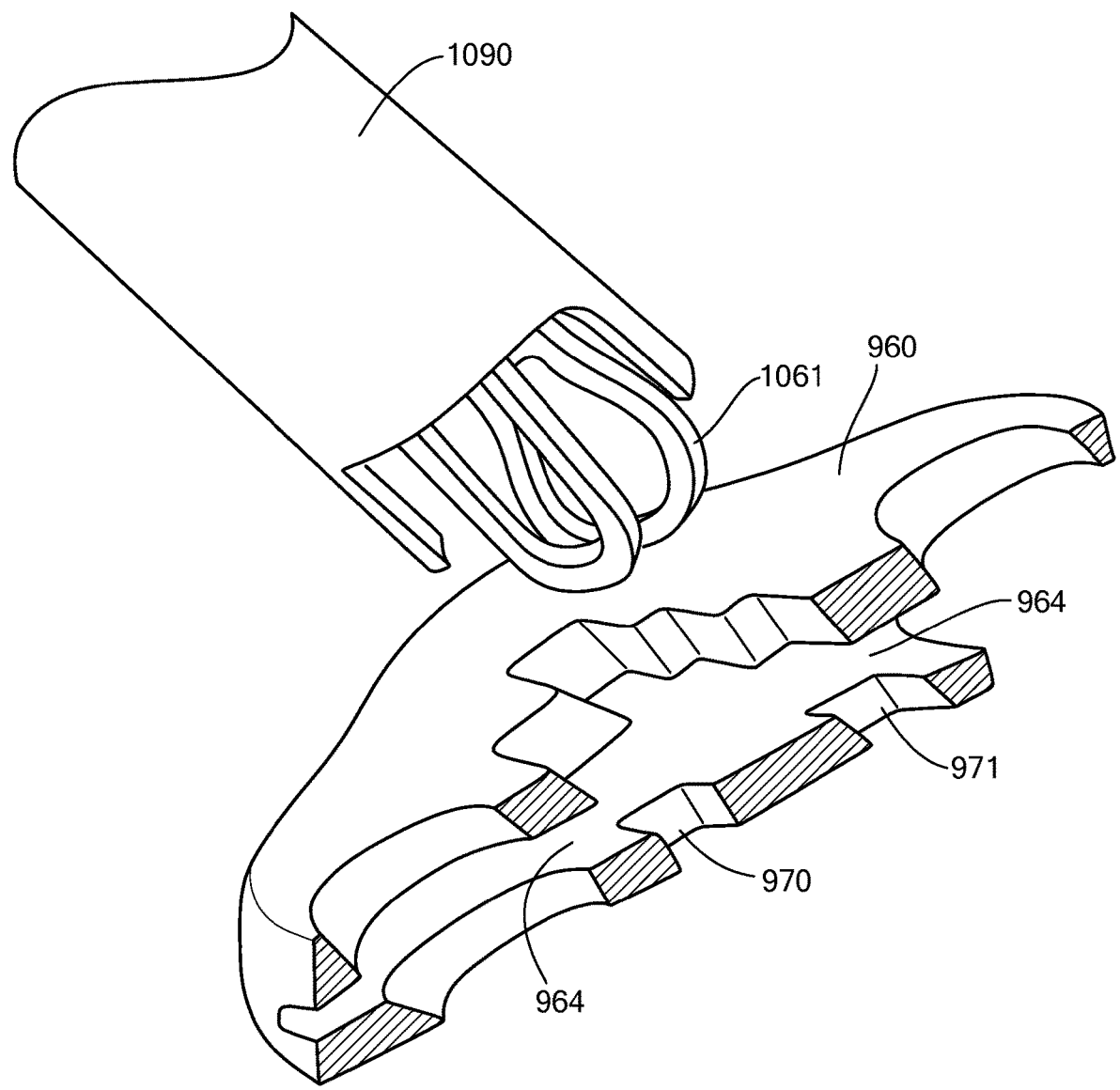
FIG. 113 illustrates a cross-sectional view of the central core shown in FIG. 106 after the ribbon has been removed from the core via the ribbon wire.

FIG. 113 illustrates a cross-sectional view of the central core shown in FIG. 106 after the ribbon has been removed from the core via the ribbon wire. As the ribbon wire is retracted further, the ribbon 1061 may be completely removed from core 960 through opening 961. The sutures may be cut in accordance with some embodiments in order to allow complete withdrawal of the ribbon from core 960. However, as discussed further below, the ribbon may be configured to release the sutures extending through the apertures of the ribbons without cutting the sutures.

With reference to FIGS. 114-118, after suture 104 is positioned within channel 111, in a manner described hereinabove, capture and release ribbon component 313 will disengage and release suture 104. In some embodiment, the disengagement of suture 104 from capture and release ribbons 313 may be a cutting action. In other embodiments, the disengagement of suture 104 involves a release mechanism 317 wherein the suture loop is knocked off from ribbon component 313. In particular, the disengagement and release of sutures 104 will occur at an exit hole on a potion of intra-arterial foot 102. Following release of suture 104, capture and release ribbon components 313 will retract completely from closure device 200.

Figure 114:
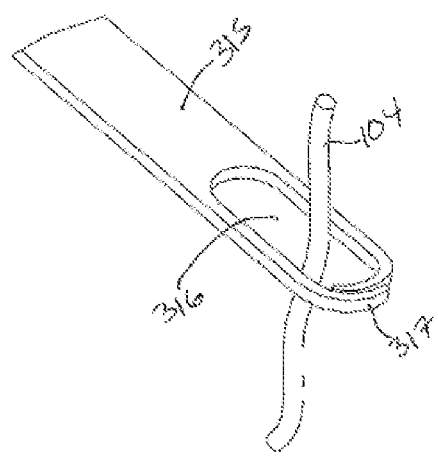
FIGS. 114-117 are perspective views of various embodiments of the capture and release ribbon component, in accordance with various embodiments of the present disclosure.
Figure 115:
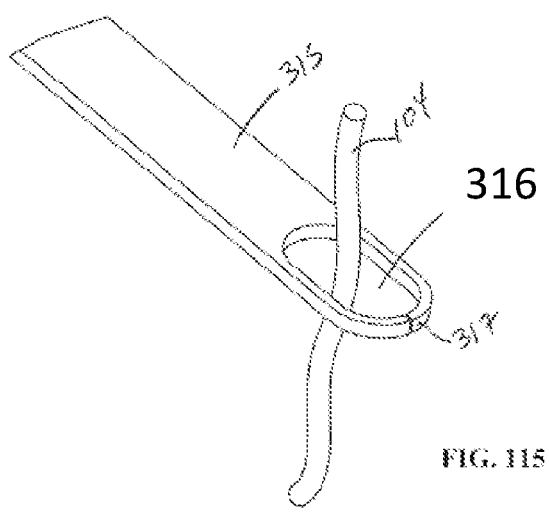
Figure 116:
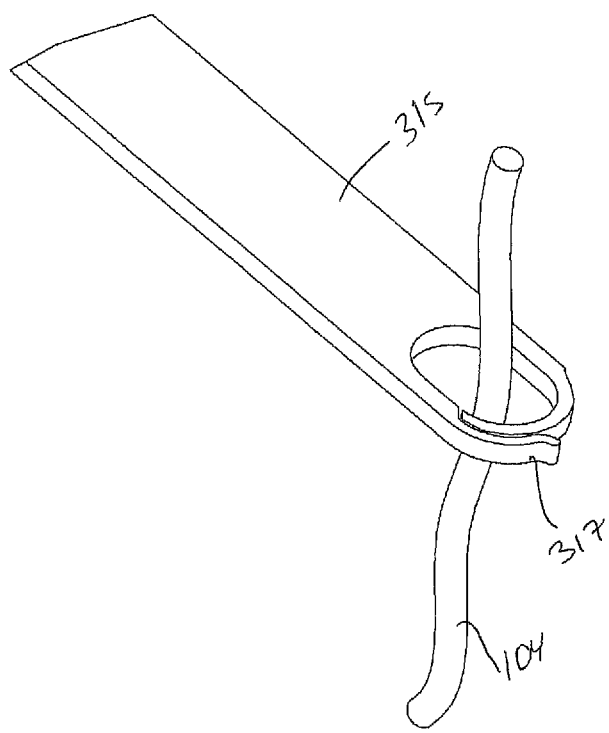
Figure 117:
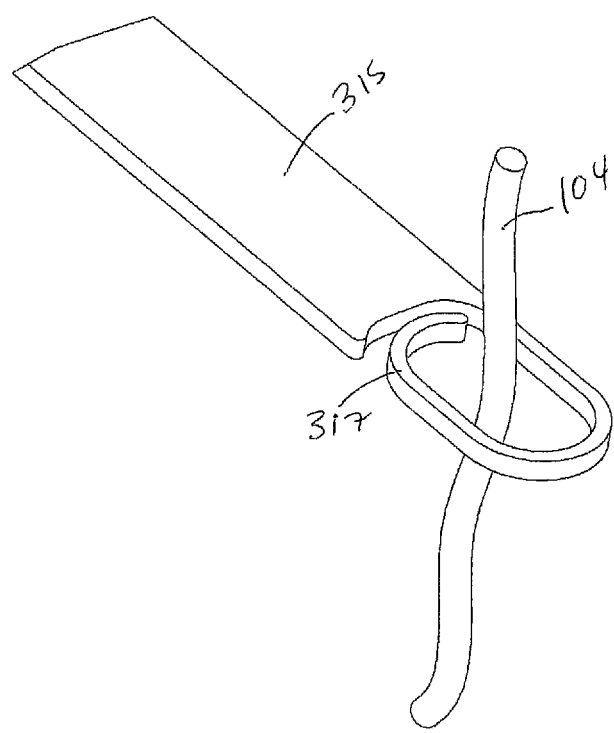
Figure 118:
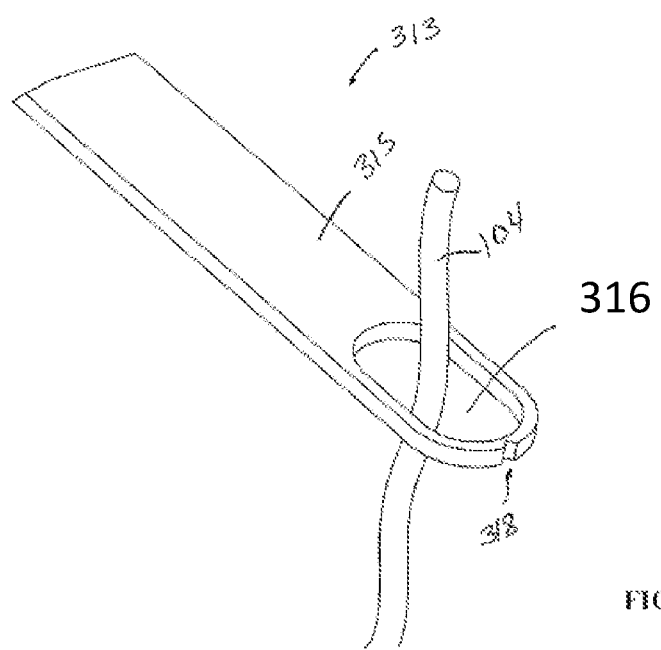
FIG. 118 is a perspective view of a capture and release ribbon component, in accordance with embodiments of the present invention.

With continued reference to FIGS. 114-118, various embodiments of the release mechanism 317 of ribbon components 313, in accordance with the present disclosure, are illustrated. Release mechanism 317 may be, for example, a cut detail, which allows ribbon 313 open and/or un-link from the captured suture 104. In one particular embodiment, capture ribbon 313 includes a laser cut nitinol ribbon with a fold out tab folding on itself and extendable in the longitudinal direction (FIGS. 114, 116 and 117).

Figure 119:
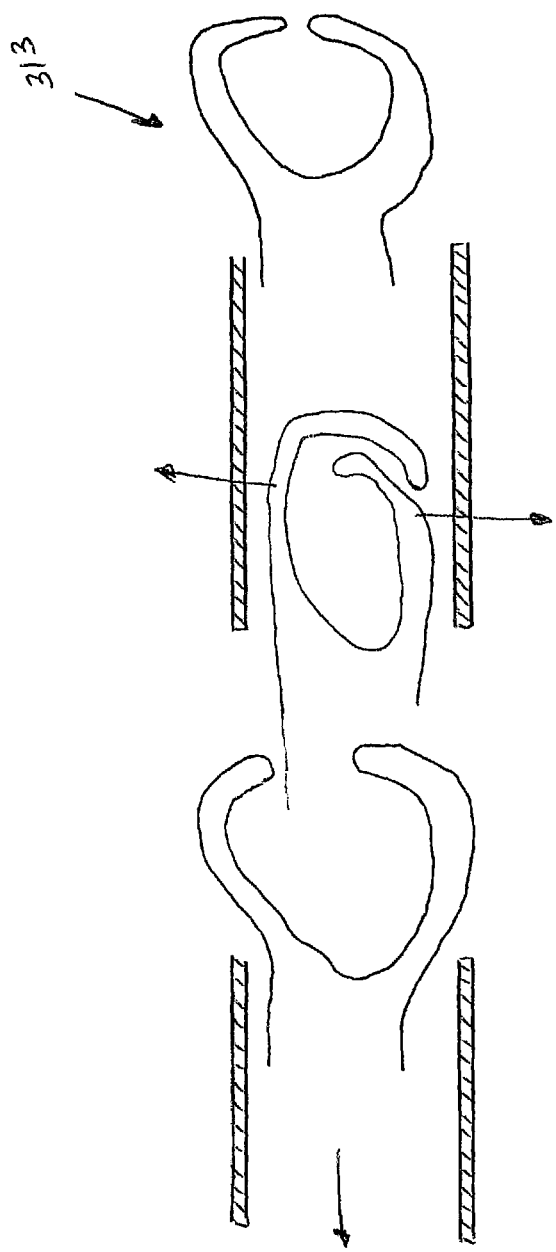
FIG. 119 is a cross-sectional view of the capture and release ribbon component of FIGS. 114-117 positioned within a sleeve, in accordance with embodiments of the present invention.

With reference for FIG. 119, ribbon component 313 is illustrated within a sleeve having a cut-out portion. The cut-out portion is adapted for allowing release mechanism 317 to release suture 104 in the event that the suture is not release by the methods described hereinabove. In particular, when the ribbon component pulls the suture, the load on the release mechanism 317 will cause the release mechanism to deploy open thus releasing the suture. The cut-out portion on the sleeve, as illustrated by the figure, will ensure that the suture is released when the suture attempts to pass through the sleeve, since the suture will apply an increased load on the mechanism 317 until the mechanism releases the suture. The sleeve is no longer retaining the capture ribbon loop.

Capture and release ribbon component 313 is a flexible member for permitting movement in and retraction from intra-arterial foot 102. In one embodiment, capture and release ribbon components 313 may be manufactured from a flexible but non-compliant plastic material, such as, for example, Polyether ether ketone (PEEK) or a metal such as, for example, nitinol or stainless steel.

While FIGS. 1-119 illustratively describe exemplary components of the exemplary closure system, according to specific embodiments of the present invention, it is to be understood that a person ordinarily skilled in the art can readily modify the demonstrated system consistent with the above descriptions. For example, although the closure system 100 is described herein as application to the an artery, it is the intent of the present disclosure that the closure system described herein will also apply to other applications, such as, for example, NOTES SILS and the closure of many surgically induced openings. It should therefore be recognized that the present disclosure is not limited to the specific embodiments illustrated herein above, but rather extends in utility to many other modification, variation, application, and embodiment, and accordingly, all such modifications, variations, applications, and embodiments are to be regarded within the scope of the present disclosure.

4. Uses and Procedures

As described generally above, a provided device is useful for closing a perforation (i.e., a hole, puncture, tear, rip, or cut) in any hollow vessel associated with a mammalian surgical procedure. One of ordinary skill in the art will appreciate that provided device is useful for closing a perforation in any lumen of a mammal, including the gastrointestinal tract (e.g., the stomach, intestines, colon, etc.), the heart, the peritoneal cavity, or a blood vessel.

In some embodiments, a provided device is useful for closing a perforation (i.e., a hole, puncture, tear, rip, or cut) in any hollow vessel associated with a human surgical procedure. In some embodiments, a provided device is suitable for closing a perforation in a veterinary surgical procedure. In certain embodiments, a veterinary surgical procedure is an equine surgical procedure.

In one embodiment, the closure system is adapted for percutaneous closure of an arteriotomy following endovascular/intra-arterial procedures. Although the closure system is described as one directed to the closure of an arteriotomy of the common femoral artery or vein, the closure system described herein is equally applicable to closure of openings in any membrane, wall, septum or vessel. Similarly, although the closure system of the present disclosure is for large hole arteriotomy (in the size range of approximately 10 to approximately 30 French units), closure system 100 is equally application to smaller hole ranges (e.g. approximately 5 to 10 French units). One particular application of the presently described closure system is of the closure of remote openings during minimal invasive surgery, such as, for example, Natural Orifice Transluminal Endoscopic Surgery (NOTES), closure of the visceral surface being crossed and the closure of patent foramen ovale.

One of ordinary skill in the art will appreciate that a variety of surgical procedures result in a perforation in a lumen of the patient. In some embodiments, the surgical procedure is SILS (single incision laparoscopic surgery, also known as "belly-button surgery"), NOTES, or laparoscopic surgery.

In some embodiments, the present invention is directed to a closure system and method of percutaneous closure of an arteriotomy following an endovascular/intra-arterial procedures.

A method of closing an arteriotomy is also described. The method includes advancing a closure system into a lumen of an artery, the closure system including a foot, at least one suture, at least one bolster attached to a proximal end of the at least one suture, and a needle/shuttle attached to a distal end of the at least one suture; deploying a flexible portion of the foot within the lumen of the artery; driving the needle through the foot to a posterior surface of the foot; and applying a tensile force on the at least one suture, the at least one bolster is secured against a adventitial surface of the artery in response to the tensile force and the foot is secured against a luminal surface of the artery in response to the tensile force. At least one of the foot, the suture, the bolster and the needle are bio-degradable. The method further includes anchoring the needle/shuttle against the posterior surface of the foot in response to the tensile force. In addition, the method further includes aligning, by the intra-arterial foot, at least two wound edges of an arteriotomy. In one embodiment, the foot is secured against a luminal surface of the artery in response to the tensile force. In addition, the foot forms a seal with a portion of the arteriotomy.

We claim:

1. A device for closing an arteriotomy, the device comprising:
    an intra-arterial foot component; and
    an extra-arterial bolster,
    wherein
        the intra-arterial foot component is a tamponade for controlling bleeding,
        the intra-arterial foot component comprises a central core and a flexible sealing wing separate from the central core and located between the central core and the extra-arterial bolster,
        a top surface of said central core is in contact with said flexible sealing wing, and
        the central core is underneath said flexible sealing wing from the perspective of the extra-arterial bolster when the intra-arterial foot component is in a sealing position,
        a longitudinal dimension of the flexible sealing wing exceeds a longitudinal dimension of the central core, and a transverse dimension of the flexible sealing wing exceeds a transverse dimension of the central core such that the flexible sealing wing is shaped to form a seal with a portion of the arteriotomy when the intra-arterial foot component is in the sealing position, and
        the central core is convex from the perspective of the flexible sealing wing such that a gap is formed between outer areas of the central core and the flexible sealing wing.

2. The device of claim 1, wherein the transverse dimension of the central core is less than a diameter of the arteriotomy.

3. The device of claim 1, wherein the transverse dimension of the flexible sealing wing is greater than a diameter of the arteriotomy.

4. The device of claim 1, wherein the intra-arterial foot component comprises a bioabsorbable material.

5. The device of claim 4, wherein the bioabsorbable material is selected from the group consisting of polyglycolic acid (PGA), polyglycolic/lactic acid (PGLA), polyurethane (PUR), polydioxanone (PDO) and any combination thereof.

6. The device of claim 1, wherein the intra-arterial foot component comprises a radiopaque material.

7. The device of claim 6, wherein the radiopaque material is selected from the group consisting of radiopaque metal alloy, barium sulfate, magnesium alloy, and any combination thereof.

8. The device of claim 1, wherein the intra-arterial foot component is porous.

9. The device of claim 1, wherein the central core has a circular configuration.

10. The device of claim 1, wherein the flexible sealing wing has a circular configuration.

11. The device of claim 1, wherein the central core has uniform thickness.

12. The device of claim 1, wherein the central core has varying thickness.

13. The device of claim 1, wherein the flexible sealing wing includes a plurality of patterned holes, slots and/or midsections.

14. The device of claim 1, wherein the flexible sealing wing has flexibility in both lateral and longitudinal planes.

15. The device of claim 1, wherein the flexible sealing wing allows elastic deformation and provides sufficient strength, stiffness or rigidity to the central core to allow correct positioning.

16. The device of claim 1, wherein more than 90% of the intra-arterial foot component is absorbed within 300 days.

17. The device of claim 1, wherein the central core and the flexible sealing wing have a same composition.

* * * * *